United States Patent
Geng

(10) Patent No.: US 11,104,719 B2
(45) Date of Patent: *Aug. 31, 2021

(54) RECOMBINANT CLUSTERIN AND USE THEREOF IN THE TREATMENT AND PREVENTION OF DISEASE

(71) Applicant: BOARD OF REGENTS OF THE UNIVERSITY OF TEXAS SYSTEM, Austin, TX (US)

(72) Inventor: Yong-Jian Geng, Houston, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/597,400

(22) Filed: Oct. 9, 2019

(65) Prior Publication Data

US 2020/0102369 A1 Apr. 2, 2020

Related U.S. Application Data

(63) Continuation of application No. 14/957,030, filed on Dec. 2, 2015, now Pat. No. 10,464,994.

(60) Provisional application No. 62/087,364, filed on Dec. 4, 2014.

(51) Int. Cl.
| | | |
|---|---|---|
| *C07K 14/775* | (2006.01) | |
| *A61P 9/10* | (2006.01) | |
| *A61K 9/00* | (2006.01) | |
| *A61K 9/19* | (2006.01) | |
| *A61K 38/00* | (2006.01) | |

(52) U.S. Cl.
CPC .............. *C07K 14/775* (2013.01); *A61P 9/10* (2018.01); *A61K 9/0019* (2013.01); *A61K 9/19* (2013.01); *A61K 38/00* (2013.01); *C07K 2319/00* (2013.01); *C07K 2319/21* (2013.01); *C07K 2319/50* (2013.01)

(58) Field of Classification Search
CPC .............. C07K 14/775; C07K 2319/00; C07K 2319/50; C07K 2319/21; A61P 9/10; A61P 3/10; A61P 9/12; A61P 9/04; A61P 9/00; A61P 3/06; A61P 25/32; A61K 9/19; A61K 9/0019; A61K 38/00
See application file for complete search history.

(56) References Cited

U.S. PATENT DOCUMENTS

| 7,524,490 B2 | 4/2009 | Geng |
| 10,464,994 B2 | 11/2019 | Geng |
| 2009/0210956 A1 | 8/2009 | Geng |

FOREIGN PATENT DOCUMENTS

| CN | 101384254 A | 3/2009 |
| WO | WO 2007/093183 | 8/2007 |

OTHER PUBLICATIONS

Ghosh et al., Plasma sialic acid index of apolipoprotein J (SIJ): a new alcohol intake marker. Alcohol. 2001;25(3):173-179 (Year: 2001).*
Yang et al., Chinese Medical Journal 128(18):2530-2534, Sep. 2015 (Year: 2015).*
Zhang et al. Science, vol. 258: 468-471, Oct. 1992 (Year: 1992).*
NIH pamphlet, National Institute on Alcohol Abuse and Alcoholism, pamphlet Retrieved online from: www.niaaa.nih.gov/publications/brochures-and-fact-sheets/alcohol-use-disorder-comparison-between-dsm; Retrieved on Mar. 26, 2021. (Year: 2020).*
"Epitope Tag Removal", Sigma-Aldrich data sheet, URL: <https://web.archive.org/web/20081030074250/http://www.sigmaaldrich.com/life-science/proteomics/recombinant-proteinexpression/purification-detection/epitope-tag-removal.html>, retrieved on Mar. 15, 2017, published online Oct. 30, 2008.
International Search Report and Written Opinion issued in International Application No. PCT/US2015/063441, dated May 25, 2016.
Invitation to Pay Additional Fees issued in International Application No. PCT/US2015/063441, mailed Mar. 14, 2016.
Leskov et al., "Synthesis and functional analyses of nuclear clusterin, a cell death protein", *Journal of Biological Chemistry*, 278(13): 11590-11600, 2003.
Park et al., "The physiological roles of apolipoprotein J/clusterin in metabolic and cardiovascular diseases", *Reviews in Endocrine and Metabolic Disorders*, 15(1): 45-53, 2013.
Prochnow et al., "Non-Secreted Clusterin Isoforms Are Translated in Rare Amounts from Distinct Human mRNA Variants and Do Not Affect Bax-Mediated Apoptosis or the NF-$\kappa$B Signaling Pathway", *PLoS One*, 8(9):e75303, 2013.
Wei et al., "Roles of clusterin in progression, chemoresistance and metastasis of human ovarian cancer", *Int J Cancer*, 125: 791-806, 2009.
Office Communication issued in corresponding Chinese Application No. 201580074616.6, dated Dec. 3, 2020.

* cited by examiner

*Primary Examiner* — Kimberly Ballard
*Assistant Examiner* — Stacey N MacFarlane
(74) *Attorney, Agent, or Firm* — Parker Highlander PLLC

(57) ABSTRACT

Recombinant clusterin polypeptides and compositions comprising the same are provided. In some aspects, recombinant clusterin or nucleic acids encoding the same may be used for treating and preventing an abnormality of morphology and function in a mammal with disease (e.g., cardiovascular diseases or alcoholism).

21 Claims, 32 Drawing Sheets
Specification includes a Sequence Listing.

CluAg-a (Clusterin) – SEQ ID NO: 1

MMKTLLLFVGLLLTWESGQVLGDQTVSDNELQEMSNQGSKYVNKEIQNAVNGVKQIKTLIEKTNEERKTLLSNLEEAKKKKEDALN
ETRESETKLKELPGVCNETMMALWEECKPCLKQTCMKFYARVCRSGSGLVGRQLEEFLNQSSPFYFWMNGDRIDSLLENDRQQTH
MLDVMQDHFSRASSIIDELFQDRFFTREPQDTYHYLPFSLPHRRPHFFFPKSRIVRSLMPFSPYEPLNFHAMFQPFLEMIHEAQQA
MDIHFHSPAFQHPPTEFIREGDDDRTVCREIRHNSTGCLRMKDQCDKCREILSVDCSTNNPSQAKLRRELDESLQVAERLTRKYNEL
LKSYQWKMLNTSSLLEQLNEQFNWVSRLANLTQGEDQYYLRVTTVASHTSDSDVPSGVTEVVVKLFDSDPITVTVPVEVSRKNPKF
METVAEKALQEYRKKHREE

CluAg-b (Clusterin-ΔTMD) – SEQ ID NO: 2

TWESGQVLGDQTVSDNELQEMSNQGSKYVNKEIQNAVNGVKQIKTLIEKTNEERKTLLSNLEEAKKKKEDALNETRESETKLKELPG
VCNETMMALWEECKPCLKQTCMKFYARVCRSGSGLVGRQLEEFLNQSSPFYFWMNGDRIDSLLENDRQQTHMLDVMQDHFSR
ASSIIDELFQDRFFTREPQDTYHYLPFSLPHRRPHFFFPKSRIVRSLMPFSPYEPLNFHAMFQPFLEMIHEAQQAMDIHFHSPAFQHP
PTEFIREGDDDRTVCREIRHNSTGCLRMKDQCDKCREILSVDCSTNNPSQAKLRRELDESLQVAERLTRKYNELLKSYQWKMLNTSS
LLEQLNEQFNWVSRLANLTQGEDQYYLRVTTVASHTSDSDVPSGVTEVVVKLFDSDPITVTVPVEVSRKNPKFMETVAEKALQEYR
KKHREE

CluAg-c (Clusterin-ΔTMD-ΔNLS) – SEQ ID NO: 3

TWESGQVLGDQTVSDNELQEMSNQGSKYVNKEIQNAVNGVKQIKTLIEKTNEERKTLLSNEDALNETRESETKLKELPGVCNETM
MALWEECKPCLKQTCMKFYARVCRSGSGLVGRQLEEFLNQSSPFYFWMNGDRIDSLLENDRQQTHMLDVMQDHFSRASSIIDEL
FQDRFFTREPQDTYHYLPFSLPHRRPHFFFPKSRIVRSLMPFSPYEPLNFHAMFQPFLEMIHEAQQAMDIHFHSPAFQHPPTEFIRE
GDDDRTVCREIRHNSTGCLRMKDQCDKCREILSVDCSTNNPSQAKLRRELDESLQVAERLTRKYNELLKSYQWKMLNTSSLLEQLNE
QFNWVSRLANLTQGEDQYYLRVTTVASHTSDSDVPSGVTEVVVKLFDSDPITVTVPVEVSRKNPKFMETVAEKALQEYRKKHREE

FIG. 2A

CluAg-Ia (HisTR-Clusterin) – SEQ ID NO: 4

HHHHHHLVPRGSMMKTLLLFVGLLLTWESGQVLGDQTVSDNELQEMSNQGSKYVNKEIQNAVNGVKQIKTLIEKTNEERKTLLSN
LEAKKKKEDALNETRESETKLKELPGVCNETMMALWEECKPCLKQTCMKFYARVCRSGSGLVGRQLEEFLNQSSPFYFWMNGDR
IDSLLENDRQQTHMLDVMQDHFSRASSIIDELFQDRFFTREPQDTYHYLPFSLPHRRPHFFFPKSRIVRSLMPFSPYEPLNFHAMFQ
PFLEMIHEAQQAMDIHFHSPAFQHPPTEFIREGDDDRTVCREIRHNSTGCLRMKDQCDKCREILSVDCSTNNPSQAKLRRELDESL
QVAERLTRKYNELLKSYQWKMLNTSSLLEQLNEQFNWVSRLANLTQGEDQYYLRVTTVASHTSDSDVPSGVTEVVVKLFDSDPITV
TVPVEVSRKNPKFMETVAEKALQEYRKKHREE

CluAg-Ib (HisTR-Clusterin-ΔTMD) – SEQ ID NO: 5

HHHHHHLVPRGSTWESGQVLGDQTVSDNELQEMSNQGSKYVNKEIQNAVNGVKQIKTLIEKTNEERKTLLSNLEAKKKKEDALN
ETRESETKLKELPGVCNETMMALWEECKPCLKQTCMKFYARVCRSGSGLVGRQLEEFLNQSSPFYFWMNGDRIDSLLENDRQQTH
MLDVMQDHFSRASSIIDELFQDRFFTREPQDTYHYLPFSLPHRRPHFFFPKSRIVRSLMPFSPYEPLNFHAMFQPFLEMIHEAQQA
MDIHFHSPAFQHPPTEFIREGDDDRTVCREIRHNSTGCLRMKDQCDKCREILSVDCSTNNPSQAKLRRELDESLQVAERLTRKYNEL
LKSYQWKMLNTSSLLEQLNEQFNWVSRLANLTQGEDQYYLRVTTVASHTSDSDVPSGVTEVVVKLFDSDPITVTVPVEVSRKNPKF
METVAEKALQEYRKKHREE

CluAg-Ic (HisTR-Clusterin-ΔTMD-ΔNLS) – SEQ ID NO: 6

HHHHHHLVPRGSTWESGQVLGDQTVSDNELQEMSNQGSKYVNKEIQNAVNGVKQIKTLIEKTNEERKTLLSNEDALNETRESETK
LKELPGVCNETMMALWEECKPCLKQTCMKFYARVCRSGSGLVGRQLEEFLNQSSPFYFWMNGDRIDSLLENDRQQTHMLDVMQ
DHFSRASSIIDELFQDRFFTREPQDTYHYLPFSLPHRRPHFFFPKSRIVRSLMPFSPYEPLNFHAMFQPFLEMIHEAQQAMDIHFHSP
AFQHPPTEFIREGDDDRTVCREIRHNSTGCLRMKDQCDKCREILSVDCSTNNPSQAKLRRELDESLQVAERLTRKYNELLKSYQWK
MLNTSSLLEQLNEQFNWVSRLANLTQGEDQYYLRVTTVASHTSDSDVPSGVTEVVVKLFDSDPITVTVPVEVSRKNPKFMETVAEK
ALQEYRKKHREE

FIG. 2B

CluAg-IIa (Clusterin-TRHis) – SEQ ID NO: 7

MMKTLLFVGLLLTWESGQVLGDQTVSDNELQEMSNQGSKYVNKEIQNAVNGVKQIKTLIEKTNEERKTLLSNLEEAKKKEDALN
ETRESETKLKELPGVCNETMMALWEECKPCLKQTCMKFYARVCRSGSGLVGRQLEEFLNQSSPFYFWMNGDRIDSLLENDRQQTH
MLDVMQDHFSRASSIIDELFQDRFFTREPQDTYHYLPFSLPHRRPHFFFPKSRIVRSLMPFSPYEPLNFHAMFQPFLEMIHEAQQA
MDIHFHSPAFQHPPTEFIREGDDDRTVCREIRHNSTGCLRMKDQCDKCREILSVDCSTNNPSQAKLRRELDESLQVAERLTRKYNEL
LKSYQWKMLNTSSLLEQLNEQFNWVSRLANLTQGEDQYYLRVTTVASHTSDSDVPSGVTEVVVKLFDSDPITVTVPVEVSRKNPKF
METVAEKALQEYRKKHREELVPRGSHHHHHH

CluAg-IIb (Clusterin-ΔTMD-TRHis) – SEQ ID NO: 8

TWESGQVLGDQTVSDNELQEMSNQGSKYVNKEIQNAVNGVKQIKTLIEKTNEERKTLLSNLEEAKKKEDALNETRESETKLKELPG
VCNETMMALWEECKPCLKQTCMKFYARVCRSGSGLVGRQLEEFLNQSSPFYFWMNGDRIDSLLENDRQQTHMLDVMQDHFSR
ASSIIDELFQDRFFTREPQDTYHYLPFSLPHRRPHFFFPKSRIVRSLMPFSPYEPLNFHAMFQPFLEMIHEAQQAMDIHFHSPAFQHP
PTEFIREGDDDRTVCREIRHNSTGCLRMKDQCDKCREILSVDCSTNNPSQAKLRRELDESLQVAERLTRKYNELLKSYQWKMLNTSS
LLEQLNEQFNWVSRLANLTQGEDQYYLRVTTVASHTSDSDVPSGVTEVVVKLFDSDPITVTVPVEVSRKNPKFMETVAEKALQEYR
KKHREELVPRGSHHHHHH

CluAg-IIc (Clusterin-ΔTMD-ΔNLS-TRHis) – SEQ ID NO: 9

MMKTTWESGQVLGDQTVSDNELQEMSNQGSKYVNKEIQNAVNGVKQIKTLIEKTNEERKTLLSNEDALNETRESETKLKELPGVC
NETMMALWEECKPCLKQTCMKFYARVCRSGSGLVGRQLEEFLNQSSPFYFWMNGDRIDSLLENDRQQTHMLDVMQDHFSRAS
SIIDELFQDRFFTREPQDTYHYLPFSLPHRRPHFFFPKSRIVRSLMPFSPYEPLNFHAMFQPFLEMIHEAQQAMDIHFHSPAFQHPPT
EFIREGDDDRTVCREIRHNSTGCLRMKDQCDKCREILSVDCSTNNPSQAKLRRELDESLQVAERLTRKYNELLKSYQWKMLNTSSLLE
QLNEQFNWVSRLANLTQGEDQYYLRVTTVASHTSDSDVPSGVTEVVVKLFDSDPITVTVPVEVSRKNPKFMETVAEKALQEYRKKH
REELVPRGSHHHHHH

FIG. 2C

CluAg-IIIa (HisEK-Clusterin) – SEQ ID NO: 10

HHHHHHDDDDKMMKTLLFVGLLLTWESGQVLGDQTVSDNELQEMSNQGSKYVNKEIQNAVNGVKQIKTLIEKTNEERKTLLSN
LEEAKKKKEDALNETRESETKLKELPGVCNETMMALWEECKPCLKQTCMKFYARVCRSGSGLVGRQLEEFLNQSSPFYFWMNGDR
IDSLLENDRQQTHMLDVMQDHFSRASSIIDELFQDRFFTREPQDTYHYLPFSLPHRRPHFFFPKSRIVRSLMPFSPYEPLNFHAMFQ
PFLEMIHEAQQAMDIHFHSPAFQHPPTEFIREGDDDRTVCREIRHNSTGCLRMKDQCDKCREILSVDCSTNNPSQAKLRRELDESL
QVAERLTRKYNELLKSYQWKMLNTSSLLEQLNEQFNWVSRLANLTQGEDQYYLRVTTVASHTSDSDVPSGVTEVVVKLFDSDPITV
TVPVEVSRKNPKFMETVAEKALQEYRKKHREE

CluAg-IIIb (HisEK-Clusterin-ΔTMD) – SEQ ID NO: 11

HHHHHHDDDDKTWESGQVLGDQTVSDNELQEMSNQGSKYVNKEIQNAVNGVKQIKTLIEKTNEERKTLLSNLEEAKKKKEDALN
ETRESETKLKELPGVCNETMMALWEECKPCLKQTCMKFYARVCRSGSGLVGRQLEEFLNQSSPFYFWMNGDRIDSLLENDRQQTH
MLDVMQDHFSRASSIIDELFQDRFFTREPQDTYHYLPFSLPHRRPHFFFPKSRIVRSLMPFSPYEPLNFHAMFQPFLEMIHEAQQA
MDIHFHSPAFQHPPTEFIREGDDDRTVCREIRHNSTGCLRMKDQCDKCREILSVDCSTNNPSQAKLRRELDESLQVAERLTRKYNEL
LKSYQWKMLNTSSLLEQLNEQFNWVSRLANLTQGEDQYYLRVTTVASHTSDSDVPSGVTEVVVKLFDSDPITVTVPVEVSRKNPKF
METVAEKALQEYRKKHREE

CluAg-IIIc (HisEK-Clusterin-ΔNLS-ΔTMD) – SEQ ID NO: 12

HHHHHHDDDDKTWESGQVLGDQTVSDNELQEMSNQGSKYVNKEIQNAVNGVKQIKTLIEKTNEERKTLLSNEDALNETRESETKL
KELPGVCNETMMALWEECKPCLKQTCMKFYARVCRSGSGLVGRQLEEFLNQSSPFYFWMNGDRIDSLLENDRQQTHMLDVMQ
DHFSRASSIIDELFQDRFFTREPQDTYHYLPFSLPHRRPHFFFPKSRIVRSLMPFSPYEPLNFHAMFQPFLEMIHEAQQAMDIHFHSP
AFQHPPTEFIREGDDDRTVCREIRHNSTGCLRMKDQCDKCREILSVDCSTNNPSQAKLRRELDESLQVAERLTRKYNELLKSYQWK
MLNTSSLLEQLNEQFNWVSRLANLTQGEDQYYLRVTTVASHTSDSDVPSGVTEVVVKLFDSDPITVTVPVEVSRKNPKFMETVAEK
ALQEYRKKHREE

FIG. 2D

CluAg-IVa (Clusterin-EKHis) – SEQ ID NO: 13

MMKTLLLFVGLLLTWESGQVLGDQTVSDNELQEMSNQGSKYVNKEIQNAVNGVKQIKTLIEKTNEERKTLLSNLEEAKKKKEDALN
ETRESETKLKELPGVCNETMMALWEECKPCLKQTCMKFYARVCRSGSGLVGRQLEEFLNQSSPFYFWMNGDRIDSLLENDRQQTH
MLDVMQDHFSRASSIIDELFQDRFFTREPQDTYHYLPFSLPHRRPHFFFPKSRIVRSLMPFSPYEPLNFHAMFQPFLEMIHEAQQA
MDIHFHSPAFQHPPTEFIREGDDDRTVCREIRHNSTGCLRMKDQCDKCREILSVDCSTNNPSQAKLRRELDESLQVAERLTRKYNEL
LKSYQWKMLNTSSLLEQLNEQFNWVSRLANLTQGEDQYYLRVTTVASHTSDSDVPSGVTEVVVKLFDSDPITVTVPVEVSRKNPKF
METVAEKALQEYRKKHREELDDDDKHHHHHH

CluAg-IVb (Clusterin-ΔTMD-EKHis) – SEQ ID NO: 14

TWESGQVLGDQTVSDNELQEMSNQGSKYVNKEIQNAVNGVKQIKTLIEKTNEERKTLLSNLEEAKKKKEDALNETRESETKLKELPG
VCNETMMALWEECKPCLKQTCMKFYARVCRSGSGLVGRQLEEFLNQSSPFYFWMNGDRIDSLLENDRQQTHMLDVMQDHFSR
ASSIIDELFQDRFFTREPQDTYHYLPFSLPHRRPHFFFPKSRIVRSLMPFSPYEPLNFHAMFQPFLEMIHEAQQAMDIHFHSPAFQHP
PTEFIREGDDDRTVCREIRHNSTGCLRMKDQCDKCREILSVDCSTNNPSQAKLRRELDESLQVAERLTRKYNELLKSYQWKMLNTSS
LLEQLNEQFNWVSRLANLTQGEDQYYLRVTTVASHTSDSDVPSGVTEVVVKLFDSDPITVTVPVEVSRKNPKFMETVAEKALQEYR
KKHREELDDDDKHHHHHH

CluAg-IVc (Clusterin-ΔTMD-ΔNLS-EKHis) – SEQ ID NO: 15

TWESGQVLGDQTVSDNELQEMSNQGSKYVNKEIQNAVNGVKQIKTLIEKTNEERKTLLSNEDALNETRESETKLKELPGVCNETM
MALWEECKPCLKQTCMKFYARVCRSGSGLVGRQLEEFLNQSSPFYFWMNGDRIDSLLENDRQQTHMLDVMQDHFSRASSIIDEL
FQDRFFTREPQDTYHYLPFSLPHRRPHFFFPKSRIVRSLMPFSPYEPLNFHAMFQPFLEMIHEAQQAMDIHFHSPAFQHPPTEFIRE
GDDDRTVCREIRHNSTGCLRMKDQCDKCREILSVDCSTNNPSQAKLRRELDESLQVAERLTRKYNELLKSYQWKMLNTSSLLEQLNE
QFNWVSRLANLTQGEDQYYLRVTTVASHTSDSDVPSGVTEVVVKLFDSDPITVTVPVEVSRKNPKFMETVAEKALQEYRKKHREEL
DDDDKHHHHHH

FIG. 2E

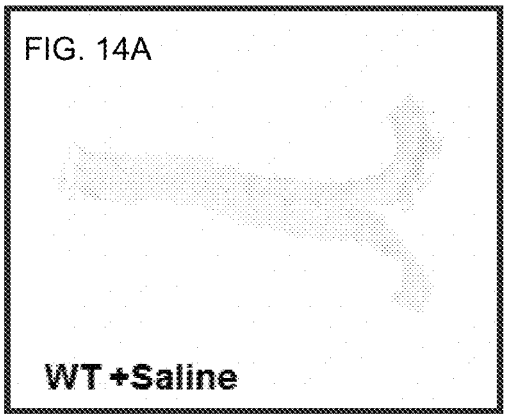
FIG. 14A WT+Saline
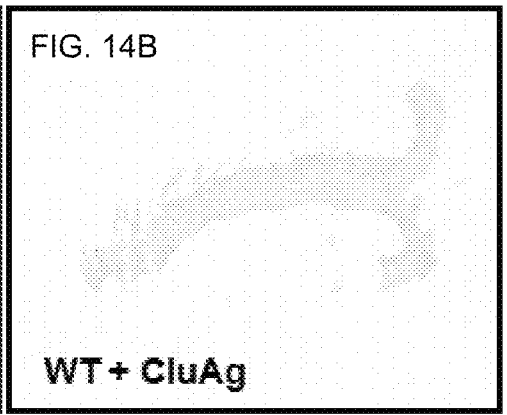
FIG. 14B WT + CluAg
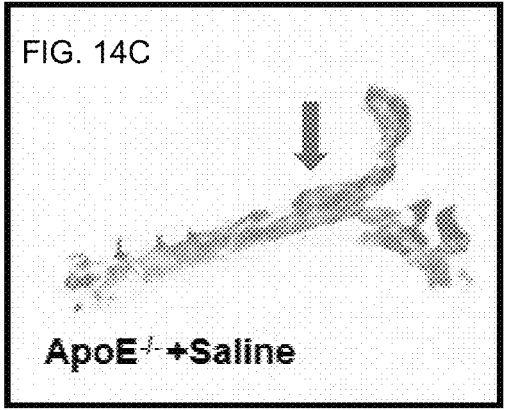
FIG. 14C ApoE-/- +Saline
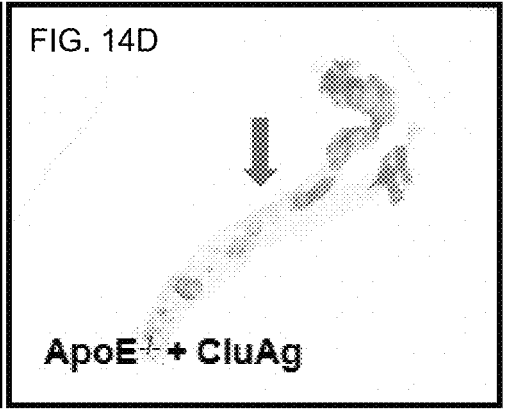
FIG. 14D ApoE-/- + CluAg

SEQUENCE LISTING

<160> NUMBER OF SEQ ID NOS: 28

<210> SEQ ID NO 1

<211> LENGTH: 449
<212> TYPE: PRT
<213> ORGANISM: Artificial Sequence
<220> FEATURE:
<223> OTHER INFORMATION: Synthetic peptide

<400> SEQUENCE: 1

```
Met Met Lys Thr Leu Leu Phe Val Gly Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380
```

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
            405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
            435                 440                 445

Glu

<210> SEQ ID NO 2
<211> LENGTH: 436
<212> TYPE: PRT
<213> ORGANISM: Artificial Sequence
<220> FEATURE:
<223> OTHER INFORMATION: Synthetic peptide

<400> SEQUENCE: 2

Thr Trp Glu Ser Gly Gln Val Leu Gly Asp Gln Thr Val Ser Asp Asn
1               5                   10                  15

Glu Leu Gln Glu Met Ser Asn Gln Gly Ser Lys Tyr Val Asn Lys Glu
            20                  25                  30

Ile Gln Asn Ala Val Asn Gly Val Lys Gln Ile Lys Thr Leu Ile Glu
        35                  40                  45

Lys Thr Asn Glu Glu Arg Lys Thr Leu Leu Ser Asn Leu Glu Glu Ala
50                  55                  60

Lys Lys Lys Lys Glu Asp Ala Leu Asn Glu Thr Arg Glu Ser Glu Thr
65                  70                  75                  80

Lys Leu Lys Glu Leu Pro Gly Val Cys Asn Glu Thr Met Met Ala Leu
            85                  90                  95

Trp Glu Glu Cys Lys Pro Cys Leu Lys Gln Thr Cys Met Lys Phe Tyr
        100                 105                 110

Ala Arg Val Cys Arg Ser Gly Ser Gly Leu Val Gly Arg Gln Leu Glu
        115                 120                 125

Glu Phe Leu Asn Gln Ser Ser Pro Phe Tyr Phe Trp Met Asn Gly Asp
    130                 135                 140

Arg Ile Asp Ser Leu Leu Glu Asn Asp Arg Gln Gln Thr His Met Leu
145                 150                 155                 160

Asp Val Met Gln Asp His Phe Ser Arg Ala Ser Ser Ile Ile Asp Glu
            165                 170                 175

Leu Phe Gln Asp Arg Phe Phe Thr Arg Glu Pro Gln Asp Thr Tyr His
            180                 185                 190

Tyr Leu Pro Phe Ser Leu Pro His Arg Arg Pro His Phe Phe Phe Pro
        195                 200                 205

Lys Ser Arg Ile Val Arg Ser Leu Met Pro Phe Ser Pro Tyr Glu Pro
210                 215                 220

Leu Asn Phe His Ala Met Phe Gln Pro Phe Leu Glu Met Ile His Glu
225                 230                 235                 240

Ala Gln Gln Ala Met Asp Ile His Phe His Ser Pro Ala Phe Gln His
            245                 250                 255

Pro Pro Thr Glu Phe Ile Arg Glu Gly Asp Asp Asp Arg Thr Val Cys
            260                 265                 270

Arg Glu Ile Arg His Asn Ser Thr Gly Cys Leu Arg Met Lys Asp Gln
        275                 280                 285

```
Cys Asp Lys Cys Arg Glu Ile Leu Ser Val Asp Cys Ser Thr Asn Asn
    290                 295                 300
Pro Ser Gln Ala Lys Leu Arg Arg Glu Leu Asp Glu Ser Leu Gln Val
305                 310                 315                 320
Ala Glu Arg Leu Thr Arg Lys Tyr Asn Glu Leu Leu Lys Ser Tyr Gln
                325                 330                 335
Trp Lys Met Leu Asn Thr Ser Ser Leu Leu Glu Gln Leu Asn Glu Gln
            340                 345                 350
Phe Asn Trp Val Ser Arg Leu Ala Asn Leu Thr Gln Gly Glu Asp Gln
        355                 360                 365
Tyr Tyr Leu Arg Val Thr Thr Val Ala Ser His Thr Ser Asp Ser Asp
    370                 375                 380
Val Pro Ser Gly Val Thr Glu Val Val Lys Leu Phe Asp Ser Asp
385                 390                 395                 400
Pro Ile Thr Val Thr Val Pro Val Glu Val Ser Arg Lys Asn Pro Lys
                405                 410                 415
Phe Met Glu Thr Val Ala Glu Lys Ala Leu Gln Glu Tyr Arg Lys Lys
            420                 425                 430
His Arg Glu Glu
        435

<210> SEQ ID NO 3
<211> LENGTH: 428
<212> TYPE: PRT
<213> ORGANISM: Artificial Sequence
<220> FEATURE:
<223> OTHER INFORMATION: Synthetic peptide

<400> SEQUENCE: 3

Thr Trp Glu Ser Gly Gln Val Leu Gly Asp Gln Thr Val Ser Asp Asn
1               5                   10                  15
Glu Leu Gln Glu Met Ser Asn Gln Gly Ser Lys Tyr Val Asn Lys Glu
                20                  25                  30
Ile Gln Asn Ala Val Asn Gly Val Lys Gln Ile Lys Thr Leu Ile Glu
            35                  40                  45
Lys Thr Asn Glu Glu Arg Lys Thr Leu Leu Ser Asn Glu Asp Ala Leu
    50                  55                  60
Asn Glu Thr Arg Glu Ser Glu Thr Lys Leu Lys Glu Leu Pro Gly Val
65                  70                  75                  80
Cys Asn Glu Thr Met Met Ala Leu Trp Glu Glu Cys Lys Pro Cys Leu
                85                  90                  95
Lys Gln Thr Cys Met Lys Phe Tyr Ala Arg Val Cys Arg Ser Gly Ser
            100                 105                 110
Gly Leu Val Gly Arg Gln Leu Glu Glu Phe Leu Asn Gln Ser Ser Pro
        115                 120                 125
Phe Tyr Phe Trp Met Asn Gly Asp Arg Ile Asp Ser Leu Leu Glu Asn
    130                 135                 140
Asp Arg Gln Gln Thr His Met Leu Asp Val Met Gln Asp His Phe Ser
145                 150                 155                 160
Arg Ala Ser Ser Ile Ile Asp Glu Leu Phe Gln Asp Arg Phe Phe Thr
                165                 170                 175
Arg Glu Pro Gln Asp Thr Tyr His Tyr Leu Pro Phe Ser Leu Pro His
            180                 185                 190
Arg Arg Pro His Phe Phe Phe Pro Lys Ser Arg Ile Val Arg Ser Leu
        195                 200                 205
```

-continued

```
Met Pro Phe Ser Pro Tyr Glu Pro Leu Asn Phe His Ala Met Phe Gln
    210                 215                 220

Pro Phe Leu Glu Met Ile His Glu Ala Gln Gln Ala Met Asp Ile His
225                 230                 235                 240

Phe His Ser Pro Ala Phe Gln His Pro Pro Thr Glu Phe Ile Arg Glu
                245                 250                 255

Gly Asp Asp Arg Thr Val Cys Arg Glu Ile Arg His Asn Ser Thr
                260                 265                 270

Gly Cys Leu Arg Met Lys Asp Gln Cys Asp Lys Cys Arg Glu Ile Leu
                275                 280                 285

Ser Val Asp Cys Ser Thr Asn Asn Pro Ser Gln Ala Lys Leu Arg Arg
290                 295                 300

Glu Leu Asp Glu Ser Leu Gln Val Ala Glu Arg Leu Thr Arg Lys Tyr
305                 310                 315                 320

Asn Glu Leu Leu Lys Ser Tyr Gln Trp Lys Met Leu Asn Thr Ser Ser
                325                 330                 335

Leu Leu Glu Gln Leu Asn Glu Gln Phe Asn Trp Val Ser Arg Leu Ala
                340                 345                 350

Asn Leu Thr Gln Gly Glu Asp Gln Tyr Tyr Leu Arg Val Thr Thr Val
                355                 360                 365

Ala Ser His Thr Ser Asp Ser Asp Val Pro Ser Gly Val Thr Glu Val
                370                 375                 380

Val Val Lys Leu Phe Asp Ser Asp Pro Ile Thr Val Thr Val Pro Val
385                 390                 395                 400

Glu Val Ser Arg Lys Asn Pro Lys Phe Met Glu Thr Val Ala Glu Lys
                405                 410                 415

Ala Leu Gln Glu Tyr Arg Lys Lys His Arg Glu Glu
                420                 425

<210> SEQ ID NO 4
<211> LENGTH: 461
<212> TYPE: PRT
<213> ORGANISM: Artificial Sequence
<220> FEATURE:
<223> OTHER INFORMATION: Synthetic peptide

<400> SEQUENCE: 4

His His His His His Leu Val Pro Arg Gly Ser Met Met Lys Thr
1               5                   10                  15

Leu Leu Leu Phe Val Gly Leu Leu Leu Thr Trp Glu Ser Gly Gln Val
                20                  25                  30

Leu Gly Asp Gln Thr Val Ser Asp Asn Glu Leu Gln Glu Met Ser Asn
                35                  40                  45

Gln Gly Ser Lys Tyr Val Asn Lys Glu Ile Gln Asn Ala Val Asn Gly
            50                  55                  60

Val Lys Gln Ile Lys Thr Leu Ile Glu Lys Thr Asn Glu Glu Arg Lys
65                  70                  75                  80

Thr Leu Leu Ser Asn Leu Glu Glu Ala Lys Lys Lys Lys Glu Asp Ala
                85                  90                  95

Leu Asn Glu Thr Arg Glu Ser Glu Thr Lys Leu Lys Glu Leu Pro Gly
                100                 105                 110

Val Cys Asn Glu Thr Met Met Ala Leu Trp Glu Glu Cys Lys Pro Cys
                115                 120                 125

Leu Lys Gln Thr Cys Met Lys Phe Tyr Ala Arg Val Cys Arg Ser Gly
                130                 135                 140
```

Ser Gly Leu Val Gly Arg Gln Leu Glu Glu Phe Leu Asn Gln Ser Ser
145                 150                 155                 160

Pro Phe Tyr Phe Trp Met Asn Gly Asp Arg Ile Asp Ser Leu Leu Glu
            165                 170                 175

Asn Asp Arg Gln Gln Thr His Met Leu Asp Val Met Gln Asp His Phe
        180                 185                 190

Ser Arg Ala Ser Ser Ile Ile Asp Glu Leu Phe Gln Asp Arg Phe Phe
    195                 200                 205

Thr Arg Glu Pro Gln Asp Thr Tyr His Tyr Leu Pro Phe Ser Leu Pro
210                 215                 220

His Arg Arg Pro His Phe Phe Pro Lys Ser Arg Ile Val Arg Ser
225                 230                 235                 240

Leu Met Pro Phe Ser Pro Tyr Glu Pro Leu Asn Phe His Ala Met Phe
            245                 250                 255

Gln Pro Phe Leu Glu Met Ile His Glu Ala Gln Ala Met Asp Ile
        260                 265                 270

His Phe His Ser Pro Ala Phe Gln His Pro Pro Thr Glu Phe Ile Arg
    275                 280                 285

Glu Gly Asp Asp Asp Arg Thr Val Cys Arg Glu Ile Arg His Asn Ser
290                 295                 300

Thr Gly Cys Leu Arg Met Lys Asp Gln Cys Asp Lys Cys Arg Glu Ile
305                 310                 315                 320

Leu Ser Val Asp Cys Ser Thr Asn Asn Pro Ser Gln Ala Lys Leu Arg
            325                 330                 335

Arg Glu Leu Asp Glu Ser Leu Gln Val Ala Glu Arg Leu Thr Arg Lys
        340                 345                 350

Tyr Asn Glu Leu Leu Lys Ser Tyr Gln Trp Lys Met Leu Asn Thr Ser
    355                 360                 365

Ser Leu Leu Glu Gln Leu Asn Glu Gln Phe Asn Trp Val Ser Arg Leu
370                 375                 380

Ala Asn Leu Thr Gln Gly Glu Asp Gln Tyr Tyr Leu Arg Val Thr Thr
385                 390                 395                 400

Val Ala Ser His Thr Ser Asp Ser Asp Val Pro Ser Gly Val Thr Glu
            405                 410                 415

Val Val Val Lys Leu Phe Asp Ser Asp Pro Ile Thr Val Thr Val Pro
        420                 425                 430

Val Glu Val Ser Arg Lys Asn Pro Lys Phe Met Glu Thr Val Ala Glu
    435                 440                 445

Lys Ala Leu Gln Glu Tyr Arg Lys Lys His Arg Glu Glu
450                 455                 460

<210> SEQ ID NO 5
<211> LENGTH: 448
<212> TYPE: PRT
<213> ORGANISM: Artificial Sequence
<220> FEATURE:
<223> OTHER INFORMATION: Synthetic peptide

<400> SEQUENCE: 5

His His His His His His Leu Val Pro Arg Gly Ser Thr Trp Glu Ser
1               5                   10                  15

Gly Gln Val Leu Gly Asp Gln Thr Val Ser Asp Asn Glu Leu Gln Glu
            20                  25                  30

Met Ser Asn Gln Gly Ser Lys Tyr Val Asn Lys Glu Ile Gln Asn Ala
        35                  40                  45

Val Asn Gly Val Lys Gln Ile Lys Thr Leu Ile Glu Lys Thr Asn Glu
 50                  55                  60

Glu Arg Lys Thr Leu Leu Ser Asn Leu Glu Glu Ala Lys Lys Lys
 65                  70                  75                  80

Glu Asp Ala Leu Asn Glu Thr Arg Glu Ser Glu Thr Lys Leu Lys Glu
                 85                  90                  95

Leu Pro Gly Val Cys Asn Glu Thr Met Met Ala Leu Trp Glu Glu Cys
            100                 105                 110

Lys Pro Cys Leu Lys Gln Thr Cys Met Lys Phe Tyr Ala Arg Val Cys
        115                 120                 125

Arg Ser Gly Ser Gly Leu Val Gly Arg Gln Leu Glu Glu Phe Leu Asn
130                 135                 140

Gln Ser Ser Pro Phe Tyr Phe Trp Met Asn Gly Asp Arg Ile Asp Ser
145                 150                 155                 160

Leu Leu Glu Asn Asp Arg Gln Gln Thr His Met Leu Asp Val Met Gln
                165                 170                 175

Asp His Phe Ser Arg Ala Ser Ser Ile Ile Asp Glu Leu Phe Gln Asp
            180                 185                 190

Arg Phe Phe Thr Arg Glu Pro Gln Asp Thr Tyr His Tyr Leu Pro Phe
        195                 200                 205

Ser Leu Pro His Arg Arg Pro His Phe Phe Phe Pro Lys Ser Arg Ile
210                 215                 220

Val Arg Ser Leu Met Pro Phe Ser Pro Tyr Glu Pro Leu Asn Phe His
225                 230                 235                 240

Ala Met Phe Gln Pro Phe Leu Glu Met Ile His Glu Ala Gln Gln Ala
                245                 250                 255

Met Asp Ile His Phe His Ser Pro Ala Phe Gln His Pro Thr Glu
            260                 265                 270

Phe Ile Arg Glu Gly Asp Asp Arg Thr Val Cys Arg Glu Ile Arg
        275                 280                 285

His Asn Ser Thr Gly Cys Leu Arg Met Lys Asp Gln Cys Asp Lys Cys
290                 295                 300

Arg Glu Ile Leu Ser Val Asp Cys Ser Thr Asn Asn Pro Ser Gln Ala
305                 310                 315                 320

Lys Leu Arg Arg Glu Leu Asp Glu Ser Leu Gln Val Ala Glu Arg Leu
                325                 330                 335

Thr Arg Lys Tyr Asn Glu Leu Leu Lys Ser Tyr Gln Trp Lys Met Leu
            340                 345                 350

Asn Thr Ser Ser Leu Leu Glu Gln Leu Asn Glu Gln Phe Asn Trp Val
        355                 360                 365

Ser Arg Leu Ala Asn Leu Thr Gln Gly Glu Asp Gln Tyr Tyr Leu Arg
370                 375                 380

Val Thr Thr Val Ala Ser His Thr Ser Asp Ser Asp Val Pro Ser Gly
385                 390                 395                 400

Val Thr Glu Val Val Lys Leu Phe Asp Ser Asp Pro Ile Thr Val
                405                 410                 415

Thr Val Pro Val Glu Val Ser Arg Lys Asn Pro Lys Phe Met Glu Thr
            420                 425                 430

Val Ala Glu Lys Ala Leu Gln Glu Tyr Arg Lys Lys His Arg Glu Glu
        435                 440                 445

<210> SEQ ID NO 6
<211> LENGTH: 440
<212> TYPE: PRT

<213> ORGANISM: Artificial Sequence
<220> FEATURE:
<223> OTHER INFORMATION: Synthetic peptide

<400> SEQUENCE: 6

```
His His His His His His Leu Val Pro Arg Gly Ser Thr Trp Glu Ser
1               5                   10                  15

Gly Gln Val Leu Gly Asp Gln Thr Val Ser Asp Asn Glu Leu Gln Glu
            20                  25                  30

Met Ser Asn Gln Gly Ser Lys Tyr Val Asn Lys Glu Ile Gln Asn Ala
        35                  40                  45

Val Asn Gly Val Lys Gln Ile Lys Thr Leu Ile Glu Lys Thr Asn Glu
50                  55                  60

Glu Arg Lys Thr Leu Leu Ser Asn Glu Asp Ala Leu Asn Glu Thr Arg
65                  70                  75                  80

Glu Ser Glu Thr Lys Leu Lys Glu Leu Pro Gly Val Cys Asn Glu Thr
                85                  90                  95

Met Met Ala Leu Trp Glu Glu Cys Lys Pro Cys Leu Lys Gln Thr Cys
            100                 105                 110

Met Lys Phe Tyr Ala Arg Val Cys Arg Ser Gly Ser Gly Leu Val Gly
        115                 120                 125

Arg Gln Leu Glu Glu Phe Leu Asn Gln Ser Ser Pro Phe Tyr Phe Trp
130                 135                 140

Met Asn Gly Asp Arg Ile Asp Ser Leu Leu Glu Asn Asp Arg Gln Gln
145                 150                 155                 160

Thr His Met Leu Asp Val Met Gln Asp His Phe Ser Arg Ala Ser Ser
                165                 170                 175

Ile Ile Asp Glu Leu Phe Gln Asp Arg Phe Phe Thr Arg Glu Pro Gln
            180                 185                 190

Asp Thr Tyr His Tyr Leu Pro Phe Ser Leu Pro His Arg Arg Pro His
        195                 200                 205

Phe Phe Phe Pro Lys Ser Arg Ile Val Arg Ser Leu Met Pro Phe Ser
210                 215                 220

Pro Tyr Glu Pro Leu Asn Phe His Ala Met Phe Gln Pro Phe Leu Glu
225                 230                 235                 240

Met Ile His Glu Ala Gln Gln Ala Met Asp Ile His Phe His Ser Pro
                245                 250                 255

Ala Phe Gln His Pro Pro Thr Glu Phe Ile Arg Glu Gly Asp Asp Asp
            260                 265                 270

Arg Thr Val Cys Arg Glu Ile Arg His Asn Ser Thr Gly Cys Leu Arg
        275                 280                 285

Met Lys Asp Gln Cys Asp Lys Cys Arg Glu Ile Leu Ser Val Asp Cys
290                 295                 300

Ser Thr Asn Asn Pro Ser Gln Ala Lys Leu Arg Arg Glu Leu Asp Glu
305                 310                 315                 320

Ser Leu Gln Val Ala Glu Arg Leu Thr Arg Lys Tyr Asn Glu Leu Leu
                325                 330                 335

Lys Ser Tyr Gln Trp Lys Met Leu Asn Thr Ser Ser Leu Leu Glu Gln
            340                 345                 350

Leu Asn Glu Gln Phe Asn Trp Val Ser Arg Leu Ala Asn Leu Thr Gln
        355                 360                 365

Gly Glu Asp Gln Tyr Tyr Leu Arg Val Thr Thr Val Ala Ser His Thr
370                 375                 380

Ser Asp Ser Asp Val Pro Ser Gly Val Thr Glu Val Val Val Lys Leu
```

```
                385                 390                 395                 400
        Phe Asp Ser Asp Pro Ile Thr Val Thr Val Pro Val Glu Val Ser Arg
                        405                 410                 415

Lys Asn Pro Lys Phe Met Glu Thr Val Ala Glu Lys Ala Leu Gln Glu
                        420                 425                 430

Tyr Arg Lys Lys His Arg Glu Glu
                        435                 440

<210> SEQ ID NO 7
<211> LENGTH: 461
<212> TYPE: PRT
<213> ORGANISM: Artificial Sequence
<220> FEATURE:
<223> OTHER INFORMATION: Synthetic peptide

<400> SEQUENCE: 7

Met Met Lys Thr Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
```

```
            305                 310                 315                 320
Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
                340                 345                 350

Leu Asn Thr Ser Ser Leu Leu Glu Gln Leu Asn Glu Gln Phe Asn Trp
                355                 360                 365

Val Ser Arg Leu Ala Asn Leu Thr Gln Gly Glu Asp Gln Tyr Tyr Leu
                370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
                405                 410                 415

Val Thr Val Pro Val Glu Val Ser Arg Lys Asn Pro Lys Phe Met Glu
                420                 425                 430

Thr Val Ala Glu Lys Ala Leu Gln Glu Tyr Arg Lys Lys His Arg Glu
                435                 440                 445

Glu Leu Val Pro Arg Gly Ser His His His His His His
            450                 455                 460

<210> SEQ ID NO 8
<211> LENGTH: 448
<212> TYPE: PRT
<213> ORGANISM: Artificial Sequence
<220> FEATURE:
<223> OTHER INFORMATION: Synthetic peptide

<400> SEQUENCE: 8

Thr Trp Glu Ser Gly Gln Val Leu Gly Asp Gln Thr Val Ser Asp Asn
1               5                   10                  15

Glu Leu Gln Glu Met Ser Asn Gln Gly Ser Lys Tyr Val Asn Lys Glu
                20                  25                  30

Ile Gln Asn Ala Val Asn Gly Val Lys Gln Ile Lys Thr Leu Ile Glu
            35                  40                  45

Lys Thr Asn Glu Glu Arg Lys Thr Leu Leu Ser Asn Leu Glu Glu Ala
50                  55                  60

Lys Lys Lys Lys Glu Asp Ala Leu Asn Glu Thr Arg Glu Ser Glu Thr
65                  70                  75                  80

Lys Leu Lys Glu Leu Pro Gly Val Cys Asn Glu Thr Met Met Ala Leu
                85                  90                  95

Trp Glu Glu Cys Lys Pro Cys Leu Lys Gln Thr Cys Met Lys Phe Tyr
                100                 105                 110

Ala Arg Val Cys Arg Ser Gly Ser Gly Leu Val Gly Arg Gln Leu Glu
            115                 120                 125

Glu Phe Leu Asn Gln Ser Ser Pro Phe Tyr Phe Trp Met Asn Gly Asp
            130                 135                 140

Arg Ile Asp Ser Leu Leu Glu Asn Asp Arg Gln Gln Thr His Met Leu
145                 150                 155                 160

Asp Val Met Gln Asp His Phe Ser Arg Ala Ser Ser Ile Ile Asp Glu
                165                 170                 175

Leu Phe Gln Asp Arg Phe Phe Thr Arg Glu Pro Gln Asp Thr Tyr His
                180                 185                 190

Tyr Leu Pro Phe Ser Leu Pro His Arg Arg Pro His Phe Phe Pro
            195                 200                 205

Lys Ser Arg Ile Val Arg Ser Leu Met Pro Phe Ser Pro Tyr Glu Pro
```

```
                210                 215                 220
Leu Asn Phe His Ala Met Phe Gln Pro Phe Leu Glu Met Ile His Glu
225                 230                 235                 240

Ala Gln Gln Ala Met Asp Ile His Phe His Ser Pro Ala Phe Gln His
                245                 250                 255

Pro Pro Thr Glu Phe Ile Arg Glu Gly Asp Asp Arg Thr Val Cys
            260                 265                 270

Arg Glu Ile Arg His Asn Ser Thr Gly Cys Leu Arg Met Lys Asp Gln
                275                 280                 285

Cys Asp Lys Cys Arg Glu Ile Leu Ser Val Asp Cys Ser Thr Asn Asn
    290                 295                 300

Pro Ser Gln Ala Lys Leu Arg Arg Glu Leu Asp Glu Ser Leu Gln Val
305                 310                 315                 320

Ala Glu Arg Leu Thr Arg Lys Tyr Asn Glu Leu Leu Lys Ser Tyr Gln
                325                 330                 335

Trp Lys Met Leu Asn Thr Ser Ser Leu Leu Glu Gln Leu Asn Glu Gln
                340                 345                 350

Phe Asn Trp Val Ser Arg Leu Ala Asn Leu Thr Gln Gly Glu Asp Gln
            355                 360                 365

Tyr Tyr Leu Arg Val Thr Thr Val Ala Ser His Thr Ser Asp Ser Asp
370                 375                 380

Val Pro Ser Gly Val Thr Glu Val Val Val Lys Leu Phe Asp Ser Asp
385                 390                 395                 400

Pro Ile Thr Val Thr Val Pro Val Glu Val Ser Arg Lys Asn Pro Lys
                405                 410                 415

Phe Met Glu Thr Val Ala Glu Lys Ala Leu Gln Glu Tyr Arg Lys Lys
            420                 425                 430

His Arg Glu Glu Leu Val Pro Arg Gly Ser His His His His His His
                435                 440                 445

<210> SEQ ID NO 9
<211> LENGTH: 444
<212> TYPE: PRT
<213> ORGANISM: Artificial Sequence
<220> FEATURE:
<223> OTHER INFORMATION: Synthetic peptide

<400> SEQUENCE: 9

Met Met Lys Thr Thr Trp Glu Ser Gly Gln Val Leu Gly Asp Gln Thr
1               5                   10                  15

Val Ser Asp Asn Glu Leu Gln Glu Met Ser Asn Gln Gly Ser Lys Tyr
                20                  25                  30

Val Asn Lys Glu Ile Gln Asn Ala Val Asn Gly Val Lys Gln Ile Lys
            35                  40                  45

Thr Leu Ile Glu Lys Thr Asn Glu Glu Arg Lys Thr Leu Leu Ser Asn
50                  55                  60

Glu Asp Ala Leu Asn Glu Thr Arg Glu Ser Glu Thr Lys Leu Lys Glu
65                  70                  75                  80

Leu Pro Gly Val Cys Asn Glu Thr Met Met Ala Leu Trp Glu Cys
                85                  90                  95

Lys Pro Cys Leu Lys Gln Thr Cys Met Lys Phe Tyr Ala Arg Val Cys
            100                 105                 110

Arg Ser Gly Ser Gly Leu Val Gly Arg Gln Leu Glu Glu Phe Leu Asn
        115                 120                 125

Gln Ser Ser Pro Phe Tyr Phe Trp Met Asn Gly Asp Arg Ile Asp Ser
```

```
                130                 135                 140
Leu Leu Glu Asn Asp Arg Gln Gln Thr His Met Leu Asp Val Met Gln
145                 150                 155                 160

Asp His Phe Ser Arg Ala Ser Ser Ile Ile Asp Glu Leu Phe Gln Asp
                165                 170                 175

Arg Phe Phe Thr Arg Glu Pro Gln Asp Thr Tyr His Tyr Leu Pro Phe
                180                 185                 190

Ser Leu Pro His Arg Arg Pro His Phe Phe Pro Lys Ser Arg Ile
                195                 200                 205

Val Arg Ser Leu Met Pro Phe Ser Pro Tyr Glu Pro Leu Asn Phe His
210                 215                 220

Ala Met Phe Gln Pro Phe Leu Glu Met Ile His Glu Ala Gln Gln Ala
225                 230                 235                 240

Met Asp Ile His Phe His Ser Pro Ala Phe Gln His Pro Pro Thr Glu
                245                 250                 255

Phe Ile Arg Glu Gly Asp Asp Arg Thr Val Cys Arg Glu Ile Arg
                260                 265                 270

His Asn Ser Thr Gly Cys Leu Arg Met Lys Asp Gln Cys Asp Lys Cys
                275                 280                 285

Arg Glu Ile Leu Ser Val Asp Cys Ser Thr Asn Asn Pro Ser Gln Ala
                290                 295                 300

Lys Leu Arg Arg Glu Leu Asp Glu Ser Leu Gln Val Ala Glu Arg Leu
305                 310                 315                 320

Thr Arg Lys Tyr Asn Glu Leu Leu Lys Ser Tyr Gln Trp Lys Met Leu
                325                 330                 335

Asn Thr Ser Ser Leu Leu Glu Gln Leu Asn Glu Gln Phe Asn Trp Val
                340                 345                 350

Ser Arg Leu Ala Asn Leu Thr Gln Gly Glu Asp Gln Tyr Tyr Leu Arg
                355                 360                 365

Val Thr Thr Val Ala Ser His Thr Ser Asp Ser Asp Val Pro Ser Gly
370                 375                 380

Val Thr Glu Val Val Lys Leu Phe Asp Ser Asp Pro Ile Thr Val
385                 390                 395                 400

Thr Val Pro Val Glu Val Ser Arg Lys Asn Pro Lys Phe Met Glu Thr
                405                 410                 415

Val Ala Glu Lys Ala Leu Gln Glu Tyr Arg Lys Lys His Arg Glu Glu
                420                 425                 430

Leu Val Pro Arg Gly Ser His His His His His
                435                 440

<210> SEQ ID NO 10
<211> LENGTH: 460
<212> TYPE: PRT
<213> ORGANISM: Artificial Sequence
<220> FEATURE:
<223> OTHER INFORMATION: Synthetic peptide

<400> SEQUENCE: 10

His His His His His His Asp Asp Asp Lys Met Met Lys Thr Leu
1               5                   10                  15

Leu Leu Phe Val Gly Leu Leu Leu Thr Trp Glu Ser Gly Gln Val Leu
                20                  25                  30

Gly Asp Gln Thr Val Ser Asp Asn Glu Leu Gln Glu Met Ser Asn Gln
                35                  40                  45

Gly Ser Lys Tyr Val Asn Lys Glu Ile Gln Asn Ala Val Asn Gly Val
```

```
            50                  55                  60
Lys Gln Ile Lys Thr Leu Ile Glu Lys Thr Asn Glu Glu Arg Lys Thr
 65                  70                  75                  80

Leu Leu Ser Asn Leu Glu Glu Ala Lys Lys Lys Glu Asp Ala Leu
                 85                  90                  95

Asn Glu Thr Arg Glu Ser Glu Thr Lys Leu Lys Glu Leu Pro Gly Val
            100                 105                 110

Cys Asn Glu Thr Met Met Ala Leu Trp Glu Glu Cys Lys Pro Cys Leu
        115                 120                 125

Lys Gln Thr Cys Met Lys Phe Tyr Ala Arg Val Cys Arg Ser Gly Ser
    130                 135                 140

Gly Leu Val Gly Arg Gln Leu Glu Glu Phe Leu Asn Gln Ser Ser Pro
145                 150                 155                 160

Phe Tyr Phe Trp Met Asn Gly Asp Arg Ile Asp Ser Leu Leu Glu Asn
                165                 170                 175

Asp Arg Gln Gln Thr His Met Leu Asp Val Met Gln Asp His Phe Ser
            180                 185                 190

Arg Ala Ser Ser Ile Ile Asp Glu Leu Phe Gln Asp Arg Phe Phe Thr
        195                 200                 205

Arg Glu Pro Gln Asp Thr Tyr His Tyr Leu Pro Phe Ser Leu Pro His
    210                 215                 220

Arg Arg Pro His Phe Phe Phe Pro Lys Ser Arg Ile Val Arg Ser Leu
225                 230                 235                 240

Met Pro Phe Ser Pro Tyr Glu Pro Leu Asn Phe His Ala Met Phe Gln
                245                 250                 255

Pro Phe Leu Glu Met Ile His Glu Ala Gln Gln Ala Met Asp Ile His
            260                 265                 270

Phe His Ser Pro Ala Phe Gln His Pro Pro Thr Glu Phe Ile Arg Glu
        275                 280                 285

Gly Asp Asp Asp Arg Thr Val Cys Arg Glu Ile Arg His Asn Ser Thr
    290                 295                 300

Gly Cys Leu Arg Met Lys Asp Gln Cys Asp Lys Cys Arg Glu Ile Leu
305                 310                 315                 320

Ser Val Asp Cys Ser Thr Asn Asn Pro Ser Gln Ala Lys Leu Arg Arg
                325                 330                 335

Glu Leu Asp Glu Ser Leu Gln Val Ala Glu Arg Leu Thr Arg Lys Tyr
            340                 345                 350

Asn Glu Leu Leu Lys Ser Tyr Gln Trp Lys Met Leu Asn Thr Ser Ser
        355                 360                 365

Leu Leu Glu Gln Leu Asn Glu Gln Phe Asn Trp Val Ser Arg Leu Ala
    370                 375                 380

Asn Leu Thr Gln Gly Glu Asp Gln Tyr Tyr Leu Arg Val Thr Thr Val
385                 390                 395                 400

Ala Ser His Thr Ser Asp Ser Asp Val Pro Ser Gly Val Thr Glu Val
                405                 410                 415

Val Val Lys Leu Phe Asp Ser Asp Pro Ile Thr Val Thr Val Pro Val
            420                 425                 430

Glu Val Ser Arg Lys Asn Pro Lys Phe Met Glu Thr Val Ala Glu Lys
        435                 440                 445

Ala Leu Gln Glu Tyr Arg Lys Lys His Arg Glu Glu
    450                 455                 460

<210> SEQ ID NO 11
```

```
<211> LENGTH: 447
<212> TYPE: PRT
<213> ORGANISM: Artificial Sequence
<220> FEATURE:
<223> OTHER INFORMATION: Synthetic peptide

<400> SEQUENCE: 11
```

| | | | | | | | | | | | | | | |
|---|---|---|---|---|---|---|---|---|---|---|---|---|---|---|
| His | His | His | His | His | His | Asp | Asp | Asp | Lys | Thr | Trp | Glu | Ser | Gly |
| 1 | | | | 5 | | | | | 10 | | | | | 15 |
| Gln | Val | Leu | Gly | Asp | Gln | Thr | Val | Ser | Asp | Asn | Glu | Leu | Gln | Glu | Met |
| | | | 20 | | | | | 25 | | | | | 30 | | |
| Ser | Asn | Gln | Gly | Ser | Lys | Tyr | Val | Asn | Lys | Glu | Ile | Gln | Asn | Ala | Val |
| | | | 35 | | | | 40 | | | | | 45 | | | |
| Asn | Gly | Val | Lys | Gln | Ile | Lys | Thr | Leu | Ile | Glu | Lys | Thr | Asn | Glu | Glu |
| | 50 | | | | | 55 | | | | | 60 | | | | |
| Arg | Lys | Thr | Leu | Leu | Ser | Asn | Leu | Glu | Glu | Ala | Lys | Lys | Lys | Lys | Glu |
| 65 | | | | | 70 | | | | | 75 | | | | | 80 |
| Asp | Ala | Leu | Asn | Glu | Thr | Arg | Glu | Ser | Glu | Thr | Lys | Leu | Lys | Glu | Leu |
| | | | | 85 | | | | | 90 | | | | | 95 | |
| Pro | Gly | Val | Cys | Asn | Glu | Thr | Met | Met | Ala | Leu | Trp | Glu | Glu | Cys | Lys |
| | | | | 100 | | | | | 105 | | | | | 110 | |
| Pro | Cys | Leu | Lys | Gln | Thr | Cys | Met | Lys | Phe | Tyr | Ala | Arg | Val | Cys | Arg |
| | | | 115 | | | | | 120 | | | | | 125 | | |
| Ser | Gly | Ser | Gly | Leu | Val | Gly | Arg | Gln | Leu | Glu | Glu | Phe | Leu | Asn | Gln |
| | | 130 | | | | | 135 | | | | | 140 | | | |
| Ser | Ser | Pro | Phe | Tyr | Phe | Trp | Met | Asn | Gly | Asp | Arg | Ile | Asp | Ser | Leu |
| 145 | | | | | 150 | | | | | 155 | | | | | 160 |
| Leu | Glu | Asn | Asp | Arg | Gln | Gln | Thr | His | Met | Leu | Asp | Val | Met | Gln | Asp |
| | | | | 165 | | | | | 170 | | | | | 175 | |
| His | Phe | Ser | Arg | Ala | Ser | Ser | Ile | Ile | Asp | Glu | Leu | Phe | Gln | Asp | Arg |
| | | | 180 | | | | | 185 | | | | | 190 | | |
| Phe | Phe | Thr | Arg | Glu | Pro | Gln | Asp | Thr | Tyr | His | Tyr | Leu | Pro | Phe | Ser |
| | | 195 | | | | | 200 | | | | | 205 | | | |
| Leu | Pro | His | Arg | Arg | Pro | His | Phe | Phe | Phe | Pro | Lys | Ser | Arg | Ile | Val |
| | 210 | | | | | 215 | | | | | 220 | | | | |
| Arg | Ser | Leu | Met | Pro | Phe | Ser | Pro | Tyr | Glu | Pro | Leu | Asn | Phe | His | Ala |
| 225 | | | | | 230 | | | | | 235 | | | | | 240 |
| Met | Phe | Gln | Pro | Phe | Leu | Glu | Met | Ile | His | Glu | Ala | Gln | Gln | Ala | Met |
| | | | | 245 | | | | | 250 | | | | | 255 | |
| Asp | Ile | His | Phe | His | Ser | Pro | Ala | Phe | Gln | His | Pro | Pro | Thr | Glu | Phe |
| | | | 260 | | | | | 265 | | | | | 270 | | |
| Ile | Arg | Glu | Gly | Asp | Asp | Arg | Thr | Val | Cys | Arg | Glu | Ile | Arg | His |
| | | 275 | | | | | 280 | | | | | 285 | | | |
| Asn | Ser | Thr | Gly | Cys | Leu | Arg | Met | Lys | Asp | Gln | Cys | Asp | Lys | Cys | Arg |
| | | 290 | | | | | 295 | | | | | 300 | | | |
| Glu | Ile | Leu | Ser | Val | Asp | Cys | Ser | Thr | Asn | Asn | Pro | Ser | Gln | Ala | Lys |
| 305 | | | | | 310 | | | | | 315 | | | | | 320 |
| Leu | Arg | Arg | Glu | Leu | Asp | Glu | Ser | Leu | Gln | Val | Ala | Glu | Arg | Leu | Thr |
| | | | | 325 | | | | | 330 | | | | | 335 | |
| Arg | Lys | Tyr | Asn | Glu | Leu | Leu | Lys | Ser | Tyr | Gln | Trp | Lys | Met | Leu | Asn |
| | | | 340 | | | | | 345 | | | | | 350 | | |
| Thr | Ser | Ser | Leu | Leu | Glu | Gln | Leu | Asn | Glu | Gln | Phe | Asn | Trp | Val | Ser |
| | | 355 | | | | | 360 | | | | | 365 | | | |
| Arg | Leu | Ala | Asn | Leu | Thr | Gln | Gly | Glu | Asp | Gln | Tyr | Tyr | Leu | Arg | Val |
| | 370 | | | | | 375 | | | | | 380 | | | | |

```
Thr Thr Val Ala Ser His Thr Ser Asp Ser Asp Val Pro Ser Gly Val
385                 390                 395                 400

Thr Glu Val Val Val Lys Leu Phe Asp Ser Asp Pro Ile Thr Val Thr
            405                 410                 415

Val Pro Val Glu Val Ser Arg Lys Asn Pro Lys Phe Met Glu Thr Val
        420                 425                 430

Ala Glu Lys Ala Leu Gln Glu Tyr Arg Lys Lys His Arg Glu Glu
    435                 440                 445

<210> SEQ ID NO 12
<211> LENGTH: 439
<212> TYPE: PRT
<213> ORGANISM: Artificial Sequence
<220> FEATURE:
<223> OTHER INFORMATION: Synthetic peptide

<400> SEQUENCE: 12

His His His His His Asp Asp Asp Lys Thr Trp Glu Ser Gly
1               5                   10                  15

Gln Val Leu Gly Asp Gln Thr Val Ser Asp Asn Glu Leu Gln Glu Met
            20                  25                  30

Ser Asn Gln Gly Ser Lys Tyr Val Asn Lys Glu Ile Gln Asn Ala Val
        35                  40                  45

Asn Gly Val Lys Gln Ile Lys Thr Leu Ile Glu Lys Thr Asn Glu Glu
    50                  55                  60

Arg Lys Thr Leu Leu Ser Asn Glu Asp Ala Leu Asn Glu Thr Arg Glu
65                  70                  75                  80

Ser Glu Thr Lys Leu Lys Glu Leu Pro Gly Val Cys Asn Glu Thr Met
            85                  90                  95

Met Ala Leu Trp Glu Glu Cys Lys Pro Cys Leu Lys Gln Thr Cys Met
            100                 105                 110

Lys Phe Tyr Ala Arg Val Cys Arg Ser Gly Ser Gly Leu Val Gly Arg
        115                 120                 125

Gln Leu Glu Glu Phe Leu Asn Gln Ser Ser Pro Phe Tyr Phe Trp Met
    130                 135                 140

Asn Gly Asp Arg Ile Asp Ser Leu Leu Glu Asn Asp Arg Gln Gln Thr
145                 150                 155                 160

His Met Leu Asp Val Met Gln Asp His Phe Ser Arg Ala Ser Ser Ile
            165                 170                 175

Ile Asp Glu Leu Phe Gln Asp Arg Phe Phe Thr Arg Glu Pro Gln Asp
        180                 185                 190

Thr Tyr His Tyr Leu Pro Phe Ser Leu Pro His Arg Arg Pro His Phe
    195                 200                 205

Phe Phe Pro Lys Ser Arg Ile Val Arg Ser Leu Met Pro Phe Ser Pro
210                 215                 220

Tyr Glu Pro Leu Asn Phe His Ala Met Phe Gln Pro Phe Leu Glu Met
225                 230                 235                 240

Ile His Glu Ala Gln Gln Ala Met Asp Ile His Phe His Ser Pro Ala
            245                 250                 255

Phe Gln His Pro Pro Thr Glu Phe Ile Arg Glu Gly Asp Asp Arg
        260                 265                 270

Thr Val Cys Arg Glu Ile Arg His Asn Ser Thr Gly Cys Leu Arg Met
    275                 280                 285

Lys Asp Gln Cys Asp Lys Cys Arg Glu Ile Leu Ser Val Asp Cys Ser
290                 295                 300
```

```
Thr Asn Asn Pro Ser Gln Ala Lys Leu Arg Arg Glu Leu Asp Glu Ser
305                 310                 315                 320

Leu Gln Val Ala Glu Arg Leu Thr Arg Lys Tyr Asn Glu Leu Leu Lys
                325                 330                 335

Ser Tyr Gln Trp Lys Met Leu Asn Thr Ser Ser Leu Leu Glu Gln Leu
            340                 345                 350

Asn Glu Gln Phe Asn Trp Val Ser Arg Leu Ala Asn Leu Thr Gln Gly
        355                 360                 365

Glu Asp Gln Tyr Tyr Leu Arg Val Thr Thr Val Ala Ser His Thr Ser
    370                 375                 380

Asp Ser Asp Val Pro Ser Gly Val Thr Glu Val Val Lys Leu Phe
385                 390                 395                 400

Asp Ser Asp Pro Ile Thr Val Thr Val Pro Val Glu Val Ser Arg Lys
                405                 410                 415

Asn Pro Lys Phe Met Glu Thr Val Ala Glu Lys Ala Leu Gln Glu Tyr
            420                 425                 430

Arg Lys Lys His Arg Glu Glu
        435

<210> SEQ ID NO 13
<211> LENGTH: 461
<212> TYPE: PRT
<213> ORGANISM: Artificial Sequence
<220> FEATURE:
<223> OTHER INFORMATION: Synthetic peptide

<400> SEQUENCE: 13

Met Met Lys Thr Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Phe Pro Lys Ser Arg
    210                 215                 220
```

```
Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
                405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
        435                 440                 445

Glu Leu Asp Asp Asp Asp Lys His His His His His His
    450                 455                 460

<210> SEQ ID NO 14
<211> LENGTH: 448
<212> TYPE: PRT
<213> ORGANISM: Artificial Sequence
<220> FEATURE:
<223> OTHER INFORMATION: Synthetic peptide

<400> SEQUENCE: 14

Thr Trp Glu Ser Gly Gln Val Leu Gly Asp Gln Thr Val Ser Asp Asn
1               5                   10                  15

Glu Leu Gln Glu Met Ser Asn Gln Gly Ser Lys Tyr Val Asn Lys Glu
                20                  25                  30

Ile Gln Asn Ala Val Asn Gly Val Lys Gln Ile Lys Thr Leu Ile Glu
            35                  40                  45

Lys Thr Asn Glu Glu Arg Lys Thr Leu Leu Ser Asn Leu Glu Glu Ala
        50                  55                  60

Lys Lys Lys Lys Glu Asp Ala Leu Asn Glu Thr Arg Glu Ser Glu Thr
65                  70                  75                  80

Lys Leu Lys Glu Leu Pro Gly Val Cys Asn Glu Thr Met Met Ala Leu
                85                  90                  95

Trp Glu Glu Cys Lys Pro Cys Leu Lys Gln Thr Cys Met Lys Phe Tyr
            100                 105                 110

Ala Arg Val Cys Arg Ser Gly Ser Gly Leu Val Gly Arg Gln Leu Glu
        115                 120                 125
```

Glu Phe Leu Asn Gln Ser Ser Pro Phe Tyr Phe Trp Met Asn Gly Asp
            130                 135                 140

Arg Ile Asp Ser Leu Leu Glu Asn Asp Arg Gln Gln Thr His Met Leu
145                 150                 155                 160

Asp Val Met Gln Asp His Phe Ser Arg Ala Ser Ser Ile Ile Asp Glu
                165                 170                 175

Leu Phe Gln Asp Arg Phe Phe Thr Arg Glu Pro Gln Asp Thr Tyr His
            180                 185                 190

Tyr Leu Pro Phe Ser Leu Pro His Arg Arg Pro His Phe Phe Pro
        195                 200                 205

Lys Ser Arg Ile Val Arg Ser Leu Met Pro Phe Ser Pro Tyr Glu Pro
210                 215                 220

Leu Asn Phe His Ala Met Phe Gln Pro Phe Leu Glu Met Ile His Glu
225                 230                 235                 240

Ala Gln Gln Ala Met Asp Ile His Phe His Ser Pro Ala Phe Gln His
                245                 250                 255

Pro Pro Thr Glu Phe Ile Arg Glu Gly Asp Asp Arg Thr Val Cys
        260                 265                 270

Arg Glu Ile Arg His Asn Ser Thr Gly Cys Leu Arg Met Lys Asp Gln
            275                 280                 285

Cys Asp Lys Cys Arg Glu Ile Leu Ser Val Asp Cys Ser Thr Asn Asn
290                 295                 300

Pro Ser Gln Ala Lys Leu Arg Arg Glu Leu Asp Glu Ser Leu Gln Val
305                 310                 315                 320

Ala Glu Arg Leu Thr Arg Lys Tyr Asn Glu Leu Leu Lys Ser Tyr Gln
                325                 330                 335

Trp Lys Met Leu Asn Thr Ser Ser Leu Leu Glu Gln Leu Asn Glu Gln
            340                 345                 350

Phe Asn Trp Val Ser Arg Leu Ala Asn Leu Thr Gln Gly Glu Asp Gln
        355                 360                 365

Tyr Tyr Leu Arg Val Thr Thr Val Ala Ser His Thr Ser Asp Ser Asp
370                 375                 380

Val Pro Ser Gly Val Thr Glu Val Val Lys Leu Phe Asp Ser Asp
385                 390                 395                 400

Pro Ile Thr Val Thr Val Pro Val Glu Val Ser Arg Lys Asn Pro Lys
                405                 410                 415

Phe Met Glu Thr Val Ala Glu Lys Ala Leu Gln Glu Tyr Arg Lys Lys
            420                 425                 430

His Arg Glu Glu Leu Asp Asp Asp Lys His His His His His His
        435                 440                 445

<210> SEQ ID NO 15
<211> LENGTH: 440
<212> TYPE: PRT
<213> ORGANISM: Artificial Sequence
<220> FEATURE:
<223> OTHER INFORMATION: Synthetic peptide

<400> SEQUENCE: 15

Thr Trp Glu Ser Gly Gln Val Leu Gly Asp Gln Thr Val Ser Asp Asn
1               5                   10                  15

Glu Leu Gln Glu Met Ser Asn Gln Gly Ser Lys Tyr Val Asn Lys Glu
            20                  25                  30

Ile Gln Asn Ala Val Asn Gly Val Lys Gln Ile Lys Thr Leu Ile Glu
        35                  40                  45

Lys Thr Asn Glu Glu Arg Lys Thr Leu Leu Ser Asn Glu Asp Ala Leu
 50                  55                  60

Asn Glu Thr Arg Glu Ser Glu Thr Lys Leu Lys Glu Leu Pro Gly Val
 65                  70                  75                  80

Cys Asn Glu Thr Met Met Ala Leu Trp Glu Glu Cys Lys Pro Cys Leu
                 85                  90                  95

Lys Gln Thr Cys Met Lys Phe Tyr Ala Arg Val Cys Arg Ser Gly Ser
             100                 105                 110

Gly Leu Val Gly Arg Gln Leu Glu Glu Phe Leu Asn Gln Ser Ser Pro
         115                 120                 125

Phe Tyr Phe Trp Met Asn Gly Asp Arg Ile Asp Ser Leu Leu Glu Asn
 130                 135                 140

Asp Arg Gln Gln Thr His Met Leu Asp Val Met Gln Asp His Phe Ser
145                 150                 155                 160

Arg Ala Ser Ser Ile Ile Asp Glu Leu Phe Gln Asp Arg Phe Phe Thr
                 165                 170                 175

Arg Glu Pro Gln Asp Thr Tyr His Tyr Leu Pro Phe Ser Leu Pro His
             180                 185                 190

Arg Arg Pro His Phe Phe Pro Lys Ser Arg Ile Val Arg Ser Leu
         195                 200                 205

Met Pro Phe Ser Pro Tyr Glu Pro Leu Asn Phe His Ala Met Phe Gln
 210                 215                 220

Pro Phe Leu Glu Met Ile His Glu Ala Gln Gln Ala Met Asp Ile His
225                 230                 235                 240

Phe His Ser Pro Ala Phe Gln His Pro Pro Thr Glu Phe Ile Arg Glu
                 245                 250                 255

Gly Asp Asp Arg Thr Val Cys Arg Glu Ile Arg His Asn Ser Thr
             260                 265                 270

Gly Cys Leu Arg Met Lys Asp Gln Cys Asp Lys Cys Arg Glu Ile Leu
         275                 280                 285

Ser Val Asp Cys Ser Thr Asn Asn Pro Ser Gln Ala Lys Leu Arg Arg
 290                 295                 300

Glu Leu Asp Glu Ser Leu Gln Val Ala Glu Arg Leu Thr Arg Lys Tyr
305                 310                 315                 320

Asn Glu Leu Leu Lys Ser Tyr Gln Trp Lys Met Leu Asn Thr Ser Ser
                 325                 330                 335

Leu Leu Glu Gln Leu Asn Glu Gln Phe Asn Trp Val Ser Arg Leu Ala
             340                 345                 350

Asn Leu Thr Gln Gly Glu Asp Gln Tyr Tyr Leu Arg Val Thr Thr Val
         355                 360                 365

Ala Ser His Thr Ser Asp Ser Asp Val Pro Ser Gly Val Thr Glu Val
 370                 375                 380

Val Val Lys Leu Phe Asp Ser Asp Pro Ile Thr Val Thr Val Pro Val
385                 390                 395                 400

Glu Val Ser Arg Lys Asn Pro Lys Phe Met Glu Thr Val Ala Glu Lys
                 405                 410                 415

Ala Leu Gln Glu Tyr Arg Lys Lys His Arg Glu Glu Leu Asp Asp Asp
             420                 425                 430

Asp Lys His His His His His His
         435                 440

<210> SEQ ID NO 16
<211> LENGTH: 6

```
<212> TYPE: PRT
<213> ORGANISM: Artificial Sequence
<220> FEATURE:
<223> OTHER INFORMATION: Protease cleavage site

<400> SEQUENCE: 16

Leu Val Pro Arg Gly Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Protease cleavage site

<400> SEQUENCE: 17

Asp Asp Asp Asp Lys
1               5

<210> SEQ ID NO 18
<211> LENGTH: 25
<212> TYPE: DNA
<213> ORGANISM: Artificial Sequence
<220> FEATURE:
<223> OTHER INFORMATION: Synthetic primer

<400> SEQUENCE: 18
cacaatatca aggatatcga cgtga                                      25

<210> SEQ ID NO 19
<211> LENGTH: 25
<212> TYPE: DNA
<213> ORGANISM: Artificial Sequence
<220> FEATURE:
<223> OTHER INFORMATION: Synthetic primer

<400> SEQUENCE: 19
acatcagttc tgttcttcgg gtaca                                      25

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
ttgtatgtgg acttcagtga tgtg                                       24

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
agttcaggtg gtcagcaagg                                            20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 22
tggctatagg atctgggtgc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
atttgctttt gcctgtttgg                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
ttacctacac cccgccagtc                                              20

<210> SEQ ID NO 25
<211> LENGTH: 19
<212> TYPE: DNA
<213> ORGANISM: Artificial Sequence
<220> FEATURE:
<223> OTHER INFORMATION: Synthetic primer

<400> SEQUENCE: 25
tgctggtctg gaagggtcc                                               19

<210> SEQ ID NO 26
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 26
gcccttggtg aaggg                                                   15

<210> SEQ ID NO 27
<211> LENGTH: 8
<212> TYPE: PRT
<213> ORGANISM: Homo sapiens

<400> SEQUENCE: 27

Leu Glu Glu Ala Lys Lys Lys Lys
1               5

<210> SEQ ID NO 28
<211> LENGTH: 9
<212> TYPE: PRT
<213> ORGANISM: Homo sapiens

<400> SEQUENCE: 28

Leu Leu Leu Phe Val Gly Leu Leu Leu
1               5
```

RECOMBINANT CLUSTERIN AND USE THEREOF IN THE TREATMENT AND PREVENTION OF DISEASE

This application is a continuation of U.S. patent application Ser. No. 14/957,030, filed Dec. 2, 2015, which claims the benefit of U.S. Provisional Patent Application No. 62/087,364, filed Dec. 4, 2014, the entirety of each of which is incorporated herein by reference.

INCORPORATION OF SEQUENCE LISTING

The sequence listing that is contained in the file named "UTSHP0306USC1_ST25.txt", which is 61 KB (as measured in Microsoft Windows®) and was created on Oct. 8, 2019, is filed herewith by electronic submission and is incorporated by reference herein.

BACKGROUND OF THE INVENTION

1. Field of the Invention

The present invention generally relates production of recombinant clusterin and the use thereof for prevention and treatment of pathological conditions.

2. Description of Related Art

Hypercholesterolemia represents the most defined risk factor for atherosclerosis, an arterial disease that causes myocardial and cerebral infarctions. Low density lipoprotein (LDL) carries cholesterol from the liver to peripheral tissues, and when elevated in blood, LDL deposits the lipid in the arterial wall, which in turn develops atherosclerotic plaques and increases the risk for thrombogenic events in the arteries. In contrast, high density lipoprotein (HDL) functions as a reverse cholesterol-transporter that removes the lipid from the arterial wall to the liver where cholesterol is metabolized. In essence, LDL is pro-atherogenic while HDL anti-atherogenic (Nicholls et al., 2005; Ansell et al., 2004; von Eckardstein et al., 2005) LDL mainly contains ApoB 100 and HDL apoE and apoA-I. In spite of the success of lowering LDL-cholesterol therapy with statins, raising HDL levels with torcetrapib (an inhibitor of cholesterol ester transfer protein (CETP) has shown little benefit to patients with atherosclerosis (Kastelein et al., 2007; Nissen et al., 2007). The failure of torcetrapib therapy underscores the incompleteness of our fundamental understanding of HDL function. HDL particles are heterogeneous in shape, density, size, composition and have multiple functional properties such as reverse cholesterol transport, as well as anti-oxidant, anti-inflammatory, and anti-thrombotic activities. Indeed, dysfunctional, proinflammatory HDL has been found in several pathological conditions, including atherosclerosis (Smith et al., 2010), diabetes (Hoofnagle et al. 2010) and autoimmune disorders (McMahon et al., 2009; Volkmann et al., 2010). Thus, the development of an anti-atherogenic, anti-apoptotic, and anti-inflammatory agent that enables HDL beneficial action is of clinical significance.

Clusterin is a sulfated, heterodimeric glycoprotein containing two 40 kDa chains joined by a unique five disulfide bond motif 1). It contains several domains, such as amphipathic helix, heparin-binding domain, and lipid-binding domain. This protein was initially identified from ram rete testes fluid and named for its ability to elicit clustering of Sertoli cells supporting sperm maturation and development (NCBI/GenBank Accession No. NM_203339, NM_001831) Thereafter, species homologues have been isolated and cloned by a number of groups working in widely divergent areas, generating various synonyms of clusterin, including testosterone repressed prostate message-2 (TRPM-2), sulfated glycoprotein-2 (SGP-2), apolipoprotein-J (Apo-J), SP-40, 40, complement cytolysis inhibitor (CLI), and dimeric acidic glycoprotein (DAG), gp 80, NA1/NA2, glycoprotein III, etc.

Encoded on a 2-kb mRNA, clusterin is transcribed from a single copy gene located on mouse chromosome 14 and human 8p21 (Fink et al., 1993), and translated as a 51 kD or so protein comprising 427 amino acid sequence (Jordan-Starck et al., 1994). In the blood stream, clusterin circulates mainly with HDL as one of apolipoproteins (Choi-Miura et al., 1992; Stuart et al., 1992) but a small portion of clusterin may exist in LDL (Karlsson et al., 2005). Clusterin expression is induced by stress responses (Wilson et al., 2000). Clusterin binds megalin/LRP-2 receptor, members of LDL receptor family. Increased expression of clusterin occurs in both human (Mackness et al., 1997; Ishikawa et al., 2001; Ishikawa et al., 1998) and experimental animal (Jordan-Starck et al., 1994; Navab et al., 1997) atherosclerotic lesions. Reported functions of clusterin include apoptosis inhibition (Kowolik et al. 2006), complement factor inactivation (Correa-Rotter et al., 1992), lipid recycling and transport (Gelissen et al., 1998), membrane protection, and maintenance of cell-cell or cell-substratum contacts. It can effectively bind to lipids and promote efflux of cholesterol and oxysterols from lipid-laden foam cells, a hall-marker of atherosclerosis (Gelissen et al., 1998). Clusterin has a high-affinity to a wide array of biological ligands. The presence of both hydrophilic and hydrophobic domains enables clusterin to act as a chaperone or a "biological detergent".

Clusterin plays a role in regulation of metabolism and function of various tissues and organs, particularly in the cardiovascular system. HDL with decreased levels of clusterin has been found in association with a high incidence of myocardiac infarction in patients with insulin-resistant metabolic syndromes (Hoofnagle et al., 2010). Administration of an oral clusterin peptide was reported to reduce atherosclerosis in ApoE-null mice (Navab et al., 2005), and intravenous injection of clusterin diminishes rat myocardiac infarction (Van Dijk et al., 2010). Transduction of clusterin can restore the mitochondrial membrane potential and prevent the release of cytochrome-c from mitochondria into cytoplasma in cardiac myoblasts damaged by ethanol (Li et al., 2007). Furthermore, increased clusterin expression in myoblasts enhances the cell capacity of migration and homing through induction of CXCR4, a chemokin-receptor for stromal cell-derived factor (SDF) (Li et al., 2010).

Human clusterin gene located in chromosome 8 (location 8p21-p18) with 17876 bp long contains 10 exons in total. Exon one and exon two are alternative yielding two different transcript isoforms. Other exons (Ansell et al., 2004; von Eckardstein et al., 2005; Kastelein et al., 2007; Nissen et al., 2007; Smith et al., 2010; Hoofnagle et al. 2010; McMahon et al., 2009; Volkmann et al., 2010) are shared with both isoforms. clusterin transcripts contain 3 different translation start sites (ATG), all in-frame. The best characterized protein isoform is produced from transcript isoform 2, where translation starts at the second ATG present in exon 2, right before ER-targeting signal. clusterin protein precursor (NP-976084) consists of 449 amino acids. There is evidence suggesting that two nuclear protein isoforms can be produced from this transcript isoform, one in which translation starts at ATG in exon 3 (417 aa), and another with translation starting from ATG in exon 1 (459 aa). Secreted clusterin is produced from the transcript isoform 2. The initial protein precursor, presecretory psCLU (~60 kDa), becomes heavily glycosylated and cleaved in the ER, and the resulting alpha and beta peptide chains are held together by 5 disulfide bonds in the mature secreted heterodimer protein form, sCLU (~75-80 kDa).

Under stimulation by ionic radiation and oxidative stress, the nuclear clusterin is first translated as a non-glycosylated protein precursor, pnCLU (~49 kDa), that is then translocated into nucleus. There is evidence of two distinct sized nuclear clusterin proteins (~50 kDa and ~60 kDa) (Pajak et al., 2007), that could result from translation started either at ATG present in exon 3 or in exon 1, respectively. Secreted clusterin is cytoprotective but nuclear clusterin cytotoxic. The controversy of clusterin functions mainly results from the not well-established role of the two different protein isoforms with distinct subcellular localization and somewhat opposing functionalities. Some known functions include involvement in apoptosis through complexing with Ku70 autoantigen (nCLU, proapoptotic) or interfering with Bax-activation (sCLU, antiapoptotic) (Araki et al., 2005; Klokov et al., 2004; Leskov et al., 2003; Yang et al., 2000). Clusterin has also been linked to spermatogenesis, epithelial cell differentiation, TGF-beta signaling through Smad2/Smad3 (Shin et al., 2008; Ahn et al., 2008; Lee et al., 1992), complement activation (Dietzsch et al., 1992; O'Bryan et al., 1990). Secreted native clusterin contains the sequence domains of nuclear clusterin critical for nuclear translocation and binding to nuclear death signaling proteins such as Ku70.

Despite the various roles in cellular regulation ascribed to clusterin, there remains a need for the development of recombinant clusterin and clusterin analogs as potential therapeutics. Embodiments of this invention disclose technology of producing recombinant clusterin with a high homology to the secreted form of native clusterin with a protective function, and compositions of recombinant clusterin that can be used for prevention and treatment of diseases in a mammal.

SUMMARY OF THE INVENTION

In a first embodiment, a recombinant polypeptide is provided that comprises a mammalian clusterin coding sequence. In various aspects, the clusterin coding sequence may have a deletion of a nuclear localization signal and/or transmembrane domain (TMD). In some aspects, the polypeptide may be a fusion protein comprising the clusterin coding sequence and a heterologous polypeptide sequence. For example, the polypeptide may further comprise a tag sequence. In further aspects, the polypeptide may comprise a protease cleavage site (e.g., a thrombin cleavage site (Leu-Val-Pro-Arg-Gly-Ser; SEQ ID NO: 16) or enteropeptidase cleavage site (Asp-Asp-Asp-Asp-Lys; SEQ ID NO: 17)). For example, protease cleavage site can be positioned between the tag sequence and the clusterin coding sequence. In various aspects, the tag sequence may be a polyhistidine tag. In some aspects, the tag sequence may be positioned N-terminally relative to the Clusterin coding sequence, while in other aspects the tag sequence may be positioned C-terminally relative to the Clusterin coding sequence.

In a further embodiment, a composition is provided that comprises a clusterin polypeptide of the present embodiments in a pharmaceutically acceptable carrier. In various aspects, the composition may be frozen or lyophilized.

In yet a further embodiment, an isolated polynucleotide molecule is provided that comprises a nucleic acid sequence encoding a clusterin polypeptide of the present embodiments. In some aspects, the nucleic acid sequence encoding the polypeptide may be operably linked to a promoter. In certain aspects, the promoter may be a promoter functional in mammalian, bacterial or insect cells. In some aspects, the polynucleotide molecule may be part of an expression vector, such as, a plasmid, an episomal expression vector or a viral expression vector.

In a further embodiment, a host cell is provided that comprises a polynucleotide molecule encoding a clusterin polypeptide of the present embodiments. In some aspect, the host cell may be a bacterial cell, an insect cell, or a mammalian cell. In some specific aspects, the host cell is a human cell, such as a pluripotent cell, a cardiac cell, and endothelial cell, or a cardiac or endothelial precursor cell.

In yet a further embodiment, a method of manufacture a recombinant clusterin polypeptide is provided that comprises (a) expressing a polynucleotide molecule encoding a clusterin polypeptide of the present embodiments in a cell; and (b) purifying the polypeptide from the cell. In various aspects, the polypeptide may comprise a purification tag, and purifying the polypeptide may comprise use of a matrix having an affinity for the purification tag. In some aspects, the purification tag may be a polyhistidine tag, and purifying the polypeptide may comprise purifying the polypeptide using a metal affinity column. In certain aspects, the purification tag may further comprise a protease cleavage site positioned between the tag sequence and the clusterin coding sequence, and purifying the polypeptide may comprise contacting the polypeptide with a protease that cleaves at the cleavage site.

In certain aspects, methods of the embodiments concern construction and/or transfection of a nucleotide encoding clusterin into cells of a mammalian cell or a non-mammalian cell causes sufficient expression of clusterin polypeptides. In certain embodiments, the step of causing the expression of an amount of a nucleotide encoding clusterin includes transfecting cells of the tissue with a DNA sequence encoding the entire clusterin polypeptide sequence, or a biologically active portion of the clusterin sequence, operably linked to a promoter and capable of being expressed in the cells to provide an amount of clusterin sufficient to be identified, concentrated, extracted, and purified.

In still a further embodiment, a method of treating or preventing a cardiovascular disease in a subject is provided that comprises administering an effective amount of a clusterin composition comprising (a) a recombinant clusterin polypeptide, (b) a polynucleotide (e.g., an expression vector) encoding a clusterin polypeptide, and/or (c) cells expressing exogenous clusterin polypeptide of the present embodiments. In some aspects, the cardiovascular disease may be hypertension, hyperlipidemia, hypercholesterolemia, hyperglycemia, hypertension, atherosclerosis and atherosclerosis-associated ischemic heart failure, stenosis, calcification of cardiovascular tissues, stroke, myocardial infarction or cerebral infarction. In some aspects, the cardiovascular disease is hyperlipidemia, hypercholesterolemia or atherosclerosis. In still further aspects, the cardiovascular disease may be diabetes. In various aspects, an effective amount of a clusterin composition may be an amount effective to reduce blood cholesterol, reduce blood glucose, reduce blood triglyceride, increase efflux of intracellular cholesterol, and/or increase vascular or cardiac cell survival. In some aspects an effective amount of a clusterin composition provides enhancement or promotion of cell survival and growth against cytotoxic or cytostatic factors, including but not limited to, oxysterols, oxidized lipoproteins, and proinflammatory cytokines.

In accordance with certain embodiments, a method of treating or preventing atherosclerosis, or a complication thereof in a mammal, is provided. For the purposes of this disclosure, the term "preventing" atherosclerosis has its usual meaning in the art and includes "deterring" and "reducing the risk of" atherosclerosis. This method comprises carrying out an above-described method wherein the tissue is a cardiac or vascular or brain region comprising an atherosclerotic lesion, or an area that is at risk of forming an atherosclerotic lesion, and wherein the contacting of cells in the tissue with clusterin polypeptides deters or prevents apoptotic cell death sufficiently to prevent, or reduce the risk of, formation of an atherosclerotic lesion. In some embodiments, the contacting of cells in the tissue with clusterin polypeptides deters or prevents tissue injury or degeneration sufficiently to prevent, or reduce the risk of, rupture of an atherosclerotic lesion.

In certain aspects, the atherosclerotic lesion comprises calcification in a vessel or a valve with inflammation, which causes vascular tissue stiffness and cardiac or aortic valve malfunction, comprising stenosis or insufficient closure. In certain of the above-described methods, the amounts of clusterin compositions are effective to deter or prevent calcification and/or protect against inflammatory injury, induced by at least one condition chosen from the group consisting of: hypercholesterolemia, hyperglycemia, hyperphosphatemia, and/or hypertension.

In some aspects, the atherosclerotic lesion or plaque comprises an unstable plaque caused by hyperlipidemia and inflammation, and the amount of clusterin contacting a treatment site are effective to stabilize the plaque (e.g., reduce the risk of rupture of the plaque, thrombus formation, or other complications).

Another embodiment of the present invention provides a method of treating acute vascular syndromes and heart failure in a mammal, which comprises delivery of an amount of clusterin composition into the heart of the mammal to protect and improve heart function.

In yet a further embodiment, a method of treating or preventing alcoholism in a subject is provided that comprises administering an effective amount of a clusterin composition comprising (a) a recombinant clusterin polypeptide, (b) a polynucleotide (e.g., an expression vector) encoding a clusterin polypeptide, and/or (c) cells expressing exogenous clusterin polypeptide of the present embodiments. In some aspects, the effective amount of the clusterin composition is an amount effective to reduce withdrawal symptoms, alcohol intact or markers of liver damage in a subject.

In some aspects, a clusterin composition of the embodiments (e.g., recombinant clusterin polypeptide, a polynucleotide encoding a clusterin polypeptide, and/or cells expressing exogenous clusterin polypeptide) may be administered by intravenous injection or catheter delivery. In some aspects, clusterin compositions are delivered into one or more tissue or organs of a mammal suffering from, or at risk of being subjected to, physical and/or chemical injury. In some embodiments the tissue is heart or vascular or brain tissue. In certain embodiments, the vascular or cardiac tissue is affected with atherosclerosis or heart failure. In other embodiments, the vascular or cardiac tissue is not affected with atherosclerosis, acute vascular syndromes, or heart failure. In some embodiments, the cells are one or more of the cell types: vascular endothelial cells, smooth muscle cells, cardiac myocytes and brain cells.

Thus, in certain aspects, there is provided a method of administering a mammalian cell, such as a stem cell, with enhanced expression of recombinant clusterin, or that have been treated with recombinant clusterin, into a tissue or organ. In some embodiments, the tissue or organ comprises a failing heart or an atherosclerotic blood vessel. In some embodiments, the stem cells are administered by intravenous injection, intra-arterial catheter, or by intramuscular or intratissue injection. In certain embodiments, the stem cells are delivered or injected together with an agent that causes vascular dilation and/or are co-administered with an anti-thrombotic agent. These and other embodiments, features and advantages embodiments of the present invention will be recognized by those of skill in the art from the following detailed description and drawings.

In further aspects, delivering an amount of recombinant clusterin comprises dissolving the polypeptide in a solution or buffer and injecting the clusterin containing solution into blood stream or tissues of a mammal or apply said clusterin solution on the surface of tissues or organs with injury.

As used herein, the terms "clusterin", "Apolipoprotein J", and "Apo J" are used interchangeably.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. In some aspects, most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-2E—Polypeptide sequences and structures of various clusterin polypeptides of the embodiments.

FIGS. 14A-14D—Oil Red O staining of WT and ApoE$^{-/-}$ aortas, evidencing that weekly intravenous injection of human recombinant clusterin analog, CluAg-I, for 3 months reduces plaque sizes in ApoE$^{-/-}$ atherosclerosis-prone mice, but not in age (6-8 months old) and sex (male)-matched normal wild type (WT) control mice. Reduced Oil red 0 staining in ApoE-/- mice treated with CluAg is observed (FIG. 14D).

DESCRIPTION OF ILLUSTRATIVE EMBODIMENTS

Figure 1:
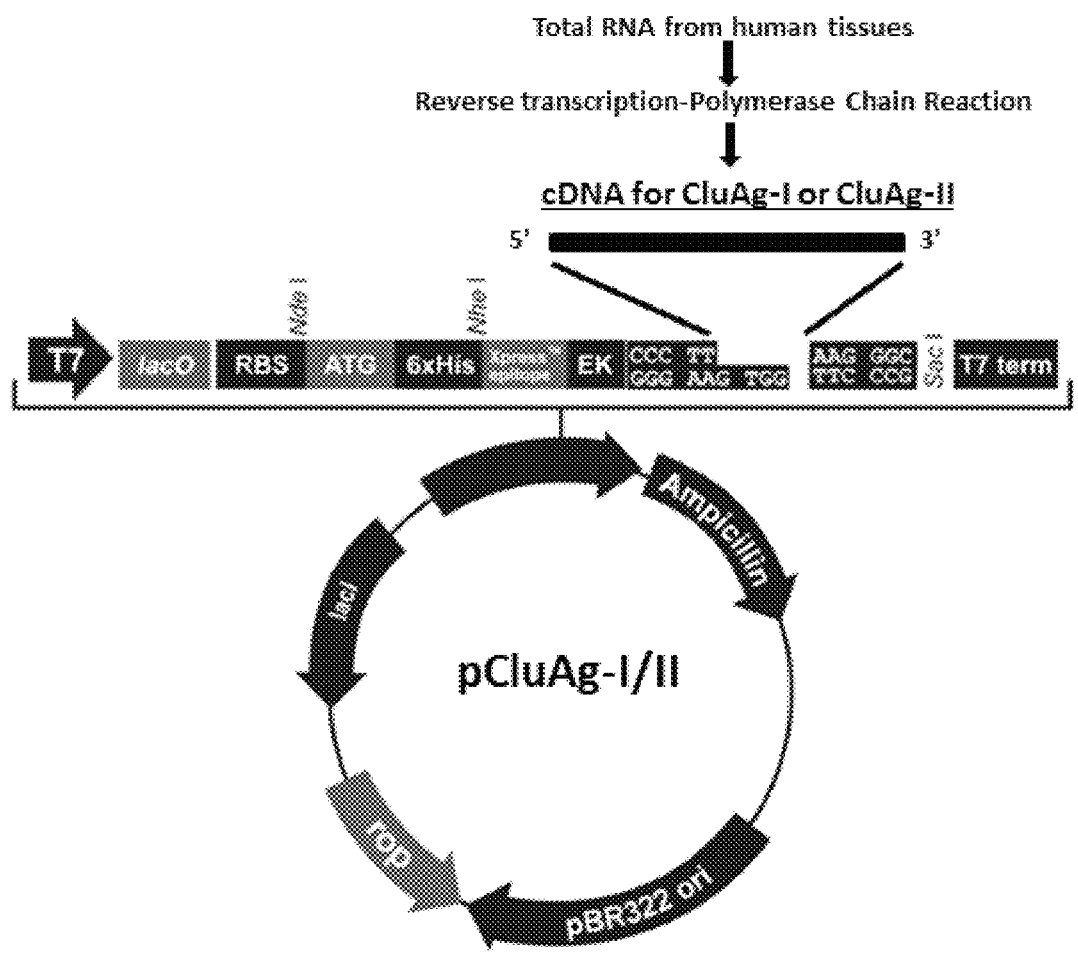
FIG. 1—A schematic representation of the clusterin analog plasmid pCluAg. Representation of clusterin cDNA subcloning and construction of an expression vector with an insert of clusterin analog-encoding cDNA is shown (SEQ ID NO: 26).

Clusterin is a multifunctional protein that may play an important role in regulation of survival, proliferation and differentiation of a diversity of cell types in a mammal. The present disclosure provides recombinant clusterin polypeptides and demonstrates the therapeutic efficacy of such recombinant polypeptides. In particular, data presented herein demonstrates that recombinant clusterin can be effectively synthesized and purified and that the clusterin polypeptide preparations are highly stable. The recombinant polypeptides appear to be essentially non-toxic, when administered to animals. However, in murine models for cardiovascular disease the clusterin polypeptides are able to reduce markers of cardiovascular disease such as hyperglycemia, hypertension and calcification as well as to normalize serum lipid levels. These data indicate that the recombinant clusterin polypeptides of the embodiments (and cells and

I. RECOMBINANT CLUSTERIN POLYPEPTIDES

For the purposes of this disclosure, the terms "clusterin" or "recombinant clusterin" refers to proteins, whose sequence is based on a mammalian clusterin sequence. In preferred aspects a recombinant clusterin polypeptide comprises a deletion of a nuclear localization signal, a transmembrane domain and/or is fused with a heterologous polypeptide sequence (e.g., a purification tag). A skilled artisan will recognize that deletions of the clusterin TMD likewise can disrupt the endoplasmic reticulum (ER)-targeting of recombinant clusterin. The terms "ApoJ" and "Clusterin" as used interchangeably herein. Examples of specific clusterin polypeptides include, without limitation., polypeptides provided as NCBI Acc. No. NM_203339, NM_001831, NM_013492, NM_053021, NM_012679, each of which is incorporated herein by reference. In certain aspects, the recombinant clusterin is about or at least about 90%, 91% 92%, 93%, 94%, 95%, 96%, 97%, 98%, or 99% identical to the clusterin polypeptide sequence of SEQ ID NOs: 1-3. For examples, in some aspects, the recombinant clusterin polypeptide about or at least about 90%, 91% 92%, 93%, 94%, 95%, 96%, 97%, 98%, or 99% identical to SEQ ID NO:1, but comprises a deletion of a nuclear localization signal, ER-targeting sequence and/or a transmembrane domain. In yet further aspects, the recombinant clusterin is about or at least about 90%, 91% 92%, 93%, 94%, 95%, 96%, 97%, 98%, or 99% identical to the clusterin polypeptide sequence of SEQ ID NOs: 4-15.

Clusterin polypeptides and fragments, mutated, truncated or deleted forms of the clusterin and/or clusterin fusion proteins can be prepared for a variety of uses, including but not limited to the generation of antibodies, as reagents in diagnostic assays, as reagents in assays for the identification of other cellular gene products involved in the regulation of clusterin mediated disorders, as reagents in assays for screening for compounds that can be used in the treatment of clusterin mediated disorders, and as pharmaceutical reagents, useful in the treatment of disorders related to clusterin.

Embodiments of the present invention also encompasses proteins that are functionally equivalent to the clusterin encoded by the nucleotide sequences described, as judged by any of a number of criteria, including but not limited to resulting in the biological effect of clusterin, a change in phenotype when the clusterin equivalent is present in an appropriate cell type. Such functionally equivalent clusterin proteins include but are not limited to additions or substitutions of amino acid residues within the amino acid sequence encoded by the clusterin nucleotide sequences described, but which result in a silent change, thus producing a functionally equivalent gene product.

In additional aspects, clusterin polypeptides may be further modified by one or more other amino substitutions while maintaining their biological activity. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in GrB and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the GrB polypeptides described herein may be modified by the substitution of an amino acid, for different, but homologous amino acid with a similar hydrophilicity value. Amino acids with hydrophilicities within +/−1.0, or +/−0.5 points are considered homologous. Furthermore, it is envisioned that clusterin sequences may be modified by amino acid deletions, substitutions, additions or insertions while retaining its biological activity.

In some aspects, a clusterin polypeptide is fused with a heterologous polypeptide sequence. For example, heterologous polypeptide sequences may be included to aid production or purification of a cell targeting construct. Some specific examples of amino acid sequences that may be attached to clusterin include, but are not limited to, purification tags (e.g., a T7, MBP. GST, HA, or polyHis tag), proteolytic cleavage sites, such as a thrombin or furin cleavage site, intracellular localization signals or secretion signals. In some aspects, a clusterin further comprises a cell-penetrating peptide (CPP). As used herein the terms CPP and membrane translocation peptide (MTP) as used interchangeably to refer to peptide sequences that enhance the ability of a protein to be internalized by a cell. Examples for CPPs for use according to the embodiments include, without limitation, peptide segments derived from HIV Tat, herpes virus VP22, the *Drosophila* Antennapedia homeobox gene product, protegrin I, as well as the T1, T2, and INF7 peptides.

Other mutations to the coding sequences described above can be made to generate polypeptides that are better suited for expression, scale up, etc. in the host cells chosen. For example, the triplet code for each amino acid can be modified to conform more closely to the preferential codon usage of the host cell's translational machinery, or, for example, to yield a messenger RNA molecule with a longer half-life. Those skilled in the art would readily know what modifications of the nucleotide sequence would be desirable to conform the nucleotide sequence to preferential codon usage or to make the messenger RNA more stable. Such information would be obtainable, for example, through use of computer programs, through review of available research data on codon usage and messenger RNA stability, and through other means known to those of skill in the art.

Polypeptides corresponding to one or more portions of clusterin, truncated or deleted clusterin as well as fusion proteins in which the full length clusterin or truncated clusterin is fused to an unrelated protein are also within the scope of the invention and can be designed on the basis of the clusterin nucleotide and clusterin amino acid sequences disclosed above. Such fusion proteins include but are not limited to IgFc fusions which stabilize the clusterin polypeptide and prolong half-life in vivo or in in vitro assays; fusions to any amino acid sequence that allows the fusion protein to be anchored to the cell membrane; or fusions to an enzyme, fluorescent protein, or luminescent protein which provide a marker function.

Additionally, the clusterin gene can be subcloned into a recombinant plasmid such that the gene's open reading frame is translationally fused to an amino-terminal tag consisting of multiple (generally about six) histidine residues. Extracts from cells infected or transfected with such constructs are loaded onto $Ni^{2+}$ nitriloacetic acid-agarose columns and histidine-tagged proteins are selectively eluted with imidazole-containing buffers.

While clusterin polypeptides can be chemically synthesized (e.g., see Creighton, 1983), large polypeptides derived from the clusterin and the full length clusterin itself may advantageously be produced by recombinant DNA technology using techniques well known in the art for expressing nucleic acids. Such methods can be used to construct expression vectors containing the clusterin nucleotide sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding Clusterin nucleotide sequences may be chemically synthesized using, for example, synthesizers. See, for example, the techniques described in "Oligonucleotide Synthesis", 1984, Gait, M. J., ed., IRL Press, Oxford, which is incorporated by reference herein in its entirety.

A variety of host-expression vector systems can be utilized to express the clusterin nucleotide sequences of embodiments of the invention. Where clusterin polypeptide is a soluble derivative (e.g., with a deleted TMD), the polypeptide can be recovered from the culture, i.e., from the host cell in cases where clusterin polypeptide is not secreted, and from the culture media in cases where clusterin polypeptide is secreted by the cells. However, the expression systems also encompass engineered host cells that express clusterin or functional equivalents in situ, i.e., anchored in the cell membrane. Purification or enrichment of clusterin from such expression systems can be accomplished using appropriate detergents and lipid micelles and methods well known to those skilled in the art. However, such engineered host cells themselves can be used in situations where it is important not only to retain the structural and functional characteristics of clusterin, but to assess biological activity, e.g., in drug screening assays.

For long-term, high-yield production of recombinant proteins, stable expression is preferred. For example, cell lines which stably express clusterin sequences can be engineered, for example, as described in SEQ ID NOs: 4-15 and in the examples below. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Clusterin gene product. Such engineered cell lines may be particularly useful in screening and evaluation of compounds that affect the endogenous activity of the Clusterin gene product. A number of selection systems can be used, including but not limited to the herpes simplex virus thymidine kinase (Wigler, et al., 1977), hypoxanthine-guanine phosphoribosyltransferase (Szybalska & Szybalski, 1962), and adenine phosphoribosyltransferase (Lowy, et al., 1980) genes can be employed in tk−, hgprt − or aprt − cells, respectively. Also, anti-metabolite resistance can be used as the basis of selection for the following genes: dhfr, which confers resistance to methotrexate (Wigler, et al., 1980; O'Hare, et al., 1981); gpt, which confers resistance to mycophenolic acid (Mulligan & Berg, 1981); neo, which confers resistance to the aminoglycoside G-418 (Colberre-Garapin, et al., 1981); and hygro, which confers resistance to hygromycin (Santerre, et al., 1984).

The expression systems that can be used for purposes of the embodiments include but are not limited to microorganisms such as bacteria (e.g., *E. coli, B. subtilis*) transformed with recombinant bacteriophage DNA, plasmid DNA or cosmid DNA expression vectors containing clusterin nucleotide sequences; yeast (e.g., *Saccharomyces, Pichia*) transformed with recombinant yeast expression vectors containing the clusterin nucleotide sequences; insect cell systems infected with recombinant virus expression vectors (e.g., baculovirus) containing the Clusterin sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Clusterin nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the clusterin gene product being expressed. For example, when a large quantity of such a protein is to be produced, for the generation of pharmaceutical compositions of clusterin protein or for raising antibodies to the clusterin protein, for example, vectors which direct the expression of high levels of fusion protein products that are readily purified may be desirable. Such vectors include, but are not limited, to the *E. coli* expression vector pUR278 (Ruther et al., 1983), in which the clusterin coding sequence may be ligated individually into the vector in frame with the lacZ coding region so that a fusion protein is produced; pIN vectors (Inouye & Inouye, 1985; Van Heeke & Schuster, 1989); and the like. pGEX vectors may also be used to express foreign polypeptides as fusion proteins with glutathione S-transferase (GST). In general; such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign sequences. The virus grows in *Spodoptera frugiperda* cells. The clusterin gene coding sequence may be cloned individually into non-essential regions (for example the polyhedrin gene) of the virus and placed under control of an AcNPV promoter (for example the polyhedrin promoter).

Successful insertion of clusterin coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted polynucleotide is expressed (e.g., see Smith et al., 1983 and U.S. Pat. No. 4,215,051).

In mammalian host cells, a number of viral-based expression systems can be utilized. In cases where an adenovirus is used as an expression vector, the clusterin nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the clusterin gene product in infected hosts (e.g., See Logan & Shenk, 1984). Specific initiation signals may also be important for efficient translation of inserted clusterin nucleotide sequences. These signals include the ATG initiation codon and adjacent sequences. In cases where an entire clusterin gene or cDNA, including its own initiation codon and adjacent sequences, is inserted into the appropriate expression vector, no additional translational control signals may be needed. However, in cases where only a portion of the clusterin coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter, et al., 1987).

In yeast, a number of vectors containing constitutive or inducible promoters may be used. For a review, see Current Protocols in Molecular Biology, 1988; Grant, et al., 1987; Wu & Grossman, 1987; Bitter, 1987; and "The Molecular Biology of the Yeast *Saccharomyces*", 1982.

In cases where plant expression vectors are used, the expression of the coding sequence may be driven by any of a number of promoters. For example, viral promoters such as the 35S RNA and 19S RNA promoters of CaMV (Brisson et al., 1984), or the coat protein promoter of TMV (Takamatsu et al., 1987) may be used; alternatively, plant promoters such as the small subunit of RUBISCO (Coruzzi et al., 1984; Broglie et al., 1984); or heat shock promoters, e.g., soybean hsp17.5-E or hsp17.3-B (Gurley et al., 1986) may be used. These constructs can be introduced into plant cells using Ti plasmids, Ri plasmids, plant virus vectors, direct DNA transformation, microinjection, electroporation, etc. For reviews of such techniques see, for example, Methods for Plant Molecular Biology 1988; and Grierson & Corey, 1988.

In cases where an adenovirus is used as an expression vector, the nucleotide sequence of interest can be ligated to an adenovirus transcription/translation control complex, e.g., the late promoter and tripartite leader sequence. This chimeric gene cam then be inserted in the adenovirus genome by in vitro or in vivo recombination. Insertion in a non-essential region of the viral genome (e.g., region E1 or E3) will result in a recombinant virus that is viable and capable of expressing the gene product of interest in infected hosts (e.g., See Logan & Shenk, 1984). Specific initiation signals such as those described above can also be important for efficient translation of inserted nucleotide sequences of interest.

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, COS, MDCK, 293, 3T3, WI38 and U937 cells.

II. THERAPEUTIC FORMULATION AND ADMINISTRATION

Therapeutics comprising clusterin polypeptides and/or nucleic acids encoding clusterin polypeptides, such as those described in SEQ ID NOs: 4-15 can be administered to a patient at therapeutically effective doses of pharmaceutical preparations used to treat or ameliorate conditions such as, but not limited to, cardiovascular disease may be hypertension, hyperlipidemia, hypercholesterolemia, hyperglycemia, hypertension, atherosclerosis and atherosclerosis-associated ischemic heart failure, stenosis, calcification of cardiovascular tissues, stroke, myocardial infarction or cerebral infarction. In some aspects, the cardiovascular disease is hyperlipidemia, hypercholesterolemia or atherosclerosis. In still further aspects, the cardiovascular disease may be diabetes. In various aspects, an effective amount of a clusterin composition may be an amount effective to reduce blood cholesterol, reduce blood glucose, reduce blood triglyceride, increase efflux of intracellular cholesterol, and/or increase vascular or cardiac cell survival. In some aspects an effective amount of a clusterin composition provides enhancement or promotion of cell survival and growth against cytotoxic or cytostatic factors, including but not limited to, oxysterols, oxidized lipoproteins, and proinflammatory cytokines, for examples those induced by alcoholism. In further aspects a therapeutically effective dose refers to that amount of the compound sufficient to result in any amelioration or retardation of disease symptoms or progression in a mammal with acute vascular syndromes, to prevent and treat degeneration, stenosis and calcification of cardiovasulcar tissues, comprising valve tissues. In further aspects, clusterin derived polypeptides can be used to prevent or treat male infertility by, for example, supporting sperm maturation and development, as has been described for native clusterin.

Toxicity and therapeutic efficacy of such clusterin derived compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions which exhibit large therapeutic indices are preferred. While compositions that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compositions are preferably within a range of circulating concentrations that include the $ED_{50}$ with little or no toxicity. The dosage may vary within this range depending upon the dosage form employed and the route of administration utilized. For any compositions used in the methods of the embodiments, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

When the therapeutic treatment of disease is contemplated, the appropriate dosage can also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agent (e.g., a clusterin polypeptide) may be complexed with a variety of well-established compounds or structures that, for instance, enhance the stability of the bioactive agent, or otherwise enhance its pharmacological properties (e.g., increase in vivo half-life, reduce toxicity, etc.).

Pharmaceutical compositions for use in accordance with the present embodiments can be formulated in conventional manner using one or more physiologically acceptable carriers or excipients.

The above therapeutic agents will be administered by any number of methods known to those of ordinary skill in the art including, but not limited to, administration by inhalation; by subcutaneous (sub-q), intravenous (I.V.), intraperitoneal (I.P.), intramuscular (I.M.), or intrathecal injection; or as a topically applied agent (transderm, ointments, creams, salves, eye drops, and the like). Thus, the compositions can be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration can be suitably formulated to give controlled release of the active composition.

For buccal administration the compositions can take the form of tablets or lozenges formulated in conventional manner.

For administration by inhalation, the compositions for use according to the embodiments are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions can be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions can also be formulated for rectal administration such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments

Example 1—General Methods and Results

Preparation of native and recombinant clusterin analogs. To treat stem cells with clusterin, two forms of clusterin were prepared. Native clusterin (NCBI Accession No. NM_0134921, incorporated herein by reference). Clusterin was prepared from blood plasma using affinity chromatography with anti-clusterin antibody. In addition, a plasmid was constructed in which mouse or human clusterin cDNA is fused with a His-tag and inserted under a promoter that will be activated in a mammalian (e.g., human cells) or non-mammalian (e.g., bacteria) cell. Schematic presentation of the plasmid pCluAg with a clusterin cDNA-His insert is shown in FIG. 1. pCluAg was constructed by inserting clusterin-TR/EK-His cDNA using a TOPO plasmid (Invitrogen). Recombinant clusterin produced by transfected mammalian cells (e.g., human 293 cells) or bacterial cells (E. coli) was purified. Different clusterin analog cDNAs were generated by RT-PCR and sequences predicting the encoding of different clusterin analog polypeptide sequences (FIGS. 2A-D and Table 1, below).

TABLE 1

Sequence Descriptions

| Description: | SEQ ID NO: |
|---|---|
| CluAg-a (recombinant Clusterin) | 1 |
| CluAg-b (recombinant Clusterin-ΔTMD) | 2 |
| CluAg-c (recombinant Clusterin-ΔTMD-ΔNLS) | 3 |
| CluAg-Ia (HisTR-Clusterin) | 4 |
| CluAg-Ib (HisTR-Clusterin-ΔTMD) | 5 |
| CluAg-Ic (HisTR-Clusterin-ΔTMD-ΔNLS) | 6 |
| CluAg-IIa (Clusterin-TR-His) | 7 |
| CluAg-IIb (Clusterin-TR-His-ΔTMD) | 8 |
| CluAg-IIc (Clusterin-TR-His-ΔTMD-ΔNLS) | 9 |
| CluAg-IIIa (HisEK-Clusterin) | 10 |
| CluAg-IIIb (HisEK-Clusterin-ΔTMD) | 11 |
| CluAg-IIIc (HisEK-Clusterin-ΔTMD-ΔNLS) | 12 |
| CluAg-IVa (HisEK-Clusterin) | 13 |
| CluAg-IVb (HisEK-Clusterin-ΔTMD) | 14 |
| CluAg-IVc (HisEK-Clusterin-ΔTMD-ΔNLS) | 15 |

Figure 3:
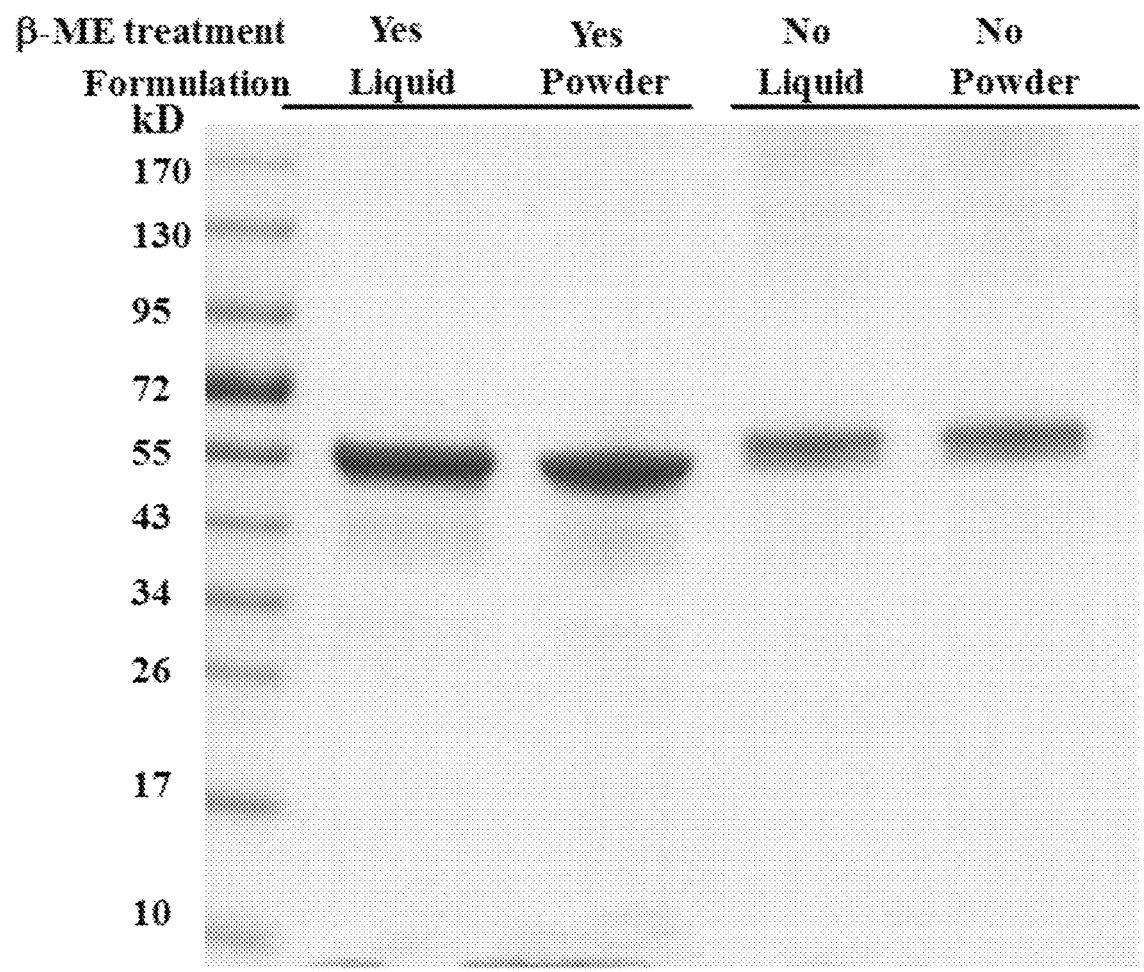
FIG. 3—Coomassie blue (G250) dye-stained polyacrylamide gel (SDS-PAGE) of recombinant human clusterin protein stored in solution and in dry powder for 3 months. The results show long term stability of the polypeptides.
Figure 4:
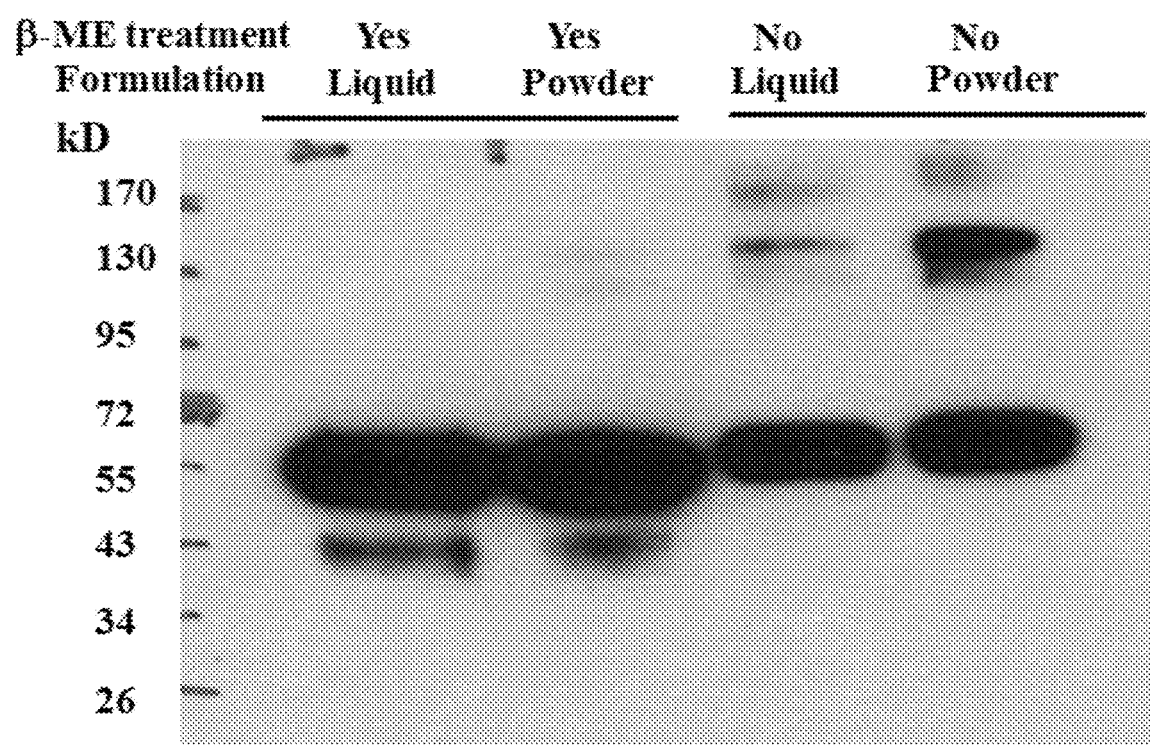
FIG. 4.—Immunoblotting analysis of the recombinant human clusterin polypeptide. Clusterin polypeptides (1 µg/lane) were loaded into SDS-PAGE (7%). After electropherosis, protein bands were transferred onto PVDF membrane, probed with rabbit anti-human clusterin antibodies (1:200), and immunostained bands were developed by chemiluminescence. The results again show long term stability of the polypeptides.
Figure 5:
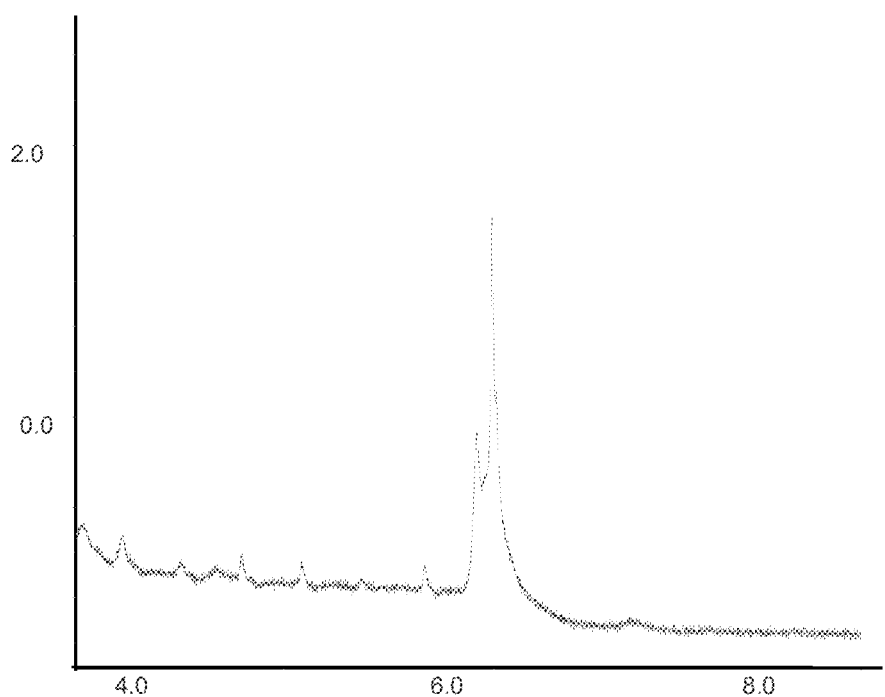
FIG. 5.—Ion exchange fast protein liquid chromatography (FPLC) of recombinant human clusterin proteins. Clusterin polypeptides were separated from other components in an aqueous solution, or buffer. The buffer flow rate was controlled by a positive-displacement pump and is normally kept constant, while the composition of the buffer can be varied by drawing fluids in different proportions from two or more external reservoirs. Ion Exchange FPLC (BioRad UnoQ12 column); Buffer A: 20 mM Tris (pH8.0) 0.5 mM EDTA; Buffer B: 20 mM Tris (pH8.0) 0.5 mM EDTA+1N NaCl; Flow rate: 2 ml/min; Injected amount: 250 ug; Result: peak eluted after 80 minutes.

Analysis of recombinant clusterin analog protein properties. The purity of recombinant clusterin analogs was examined by polyacrylamide gel electrophoresis. Clusterin analog proteins are isolated from pCluAg transfected cells, stored in solution or in dry powder, and loaded into SDS-PAGE. After electrophoresis, fractions of proteins will be electrotransferred onto a PVDF membrane, and probed with anti-clusterin antibodies. The membrane will be developed by using a chemiluminescence kit. Single bands of clusterin analog CluAg-I are visualized in SDS-PAGE stained with Commassia blue dye G250 (FIG. 3) and confirmed by immunoblotting with anti-Clu antibody (FIG. 4). Furthermore, the analogs were examined by ion exchange chromatography, showing a clear eluent of clusterin analogs (FIG. 5).

Figure 6A:
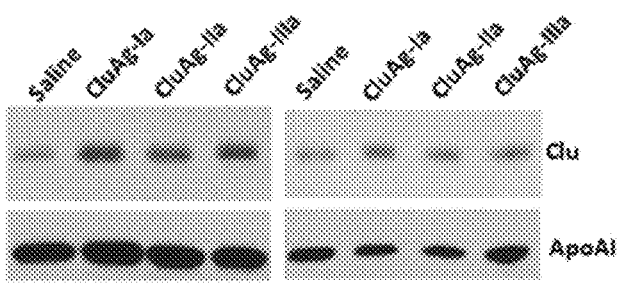
FIGS. 6A-6C—Immunoblotting analysis of levels of recombinant clusterin injected intraveneously into the blood stream of wild type and ApoE-null mice. Immunoblotting for clusterin and ApoAI proteins in the plasma of WT and ApoE-null mice with different recombinant clusterin analog (CluAg) or saline control injection (7 days) (FIG. 6A). Densitometry showed increased clusterin levels in Clu injected mice as compared to saline injected one (FIG. 6B). Co-precipitation of clusterin (Clu) in the plasma of C57BL/6 mice injected with recombinant human clusterin analogs (FIG. 6C). Apolipoprotein-A1, a known HDL component, was pulled-down with anti-ApoA1 antibody, and Western blot analysis of the ApoA1 pull-down was conducted with anti-clusterin antibodies.
Figure 6B:
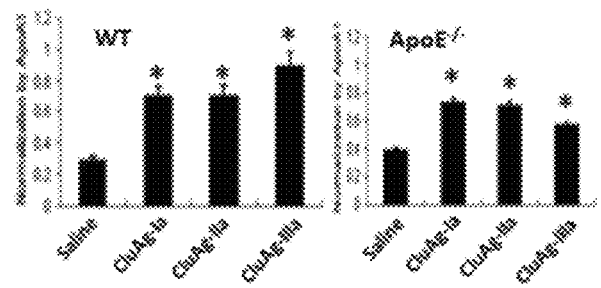
Figure 6C:
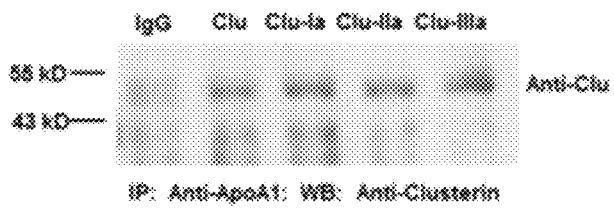
Figure 7:
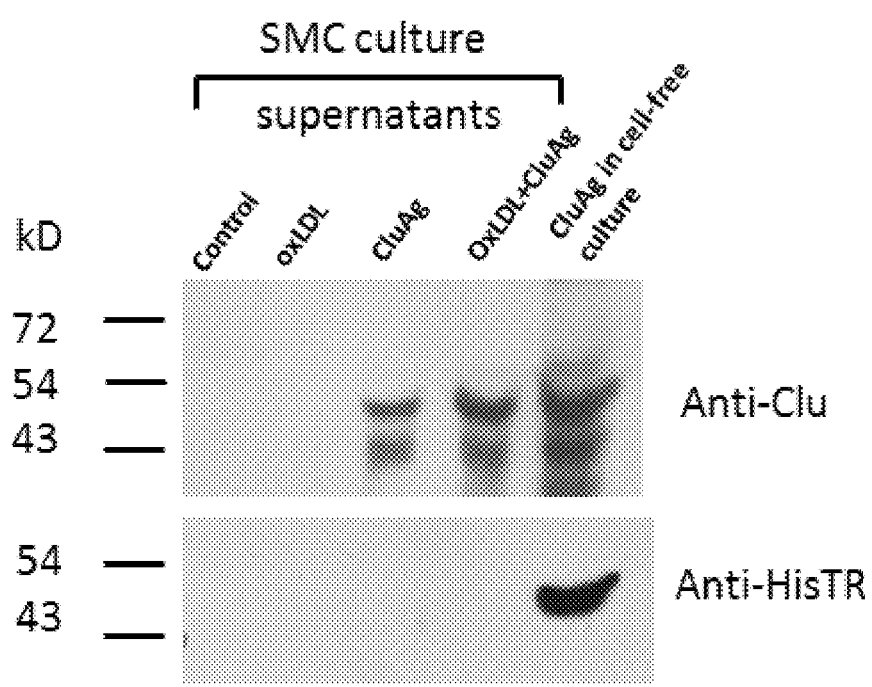
FIG. 7—Immunoblotting analysis of clusterin and HisTR tag in proteins extracted from the supernatants of human smooth muscle cell (SMC) cultures treated with oxLDL and recombinant clusterin analog (CluAg) with HisTR tag.

Clusterin analogs in the HDL fraction in mice. Apolipoprotein E deficient (ApoE$^{-/-}$) mice are widely used murine mode for atherosclerosis. To evaluate the levels of clusterin association with ApoAI in the blood, an immunoprecipitation method was developed with monoclonal antibody against apoAI and clusterin. In the plasma of blood from CluAg injected mice, ApoAI antibody co-precipitates ApoAI and CluAg, indicating that ApoAI is binding to CluAg (FIG. 6). To further confirm the presence of CluAg and compare them to native clusterin, CluAg was added to SMC culture and incubated for 2 days with 5% serum containing native clusterin in the presence of oxLDL. Supernatants of the cultures were subjected to analysis of poly-His tag in CluAg. In the culture with or without oxLDL, CluAg apparently are free of the poly-His tag while CluAg (FIG. 7) in cell free cultures contains the poly-His tag (FIG. 7).

Figure 8:
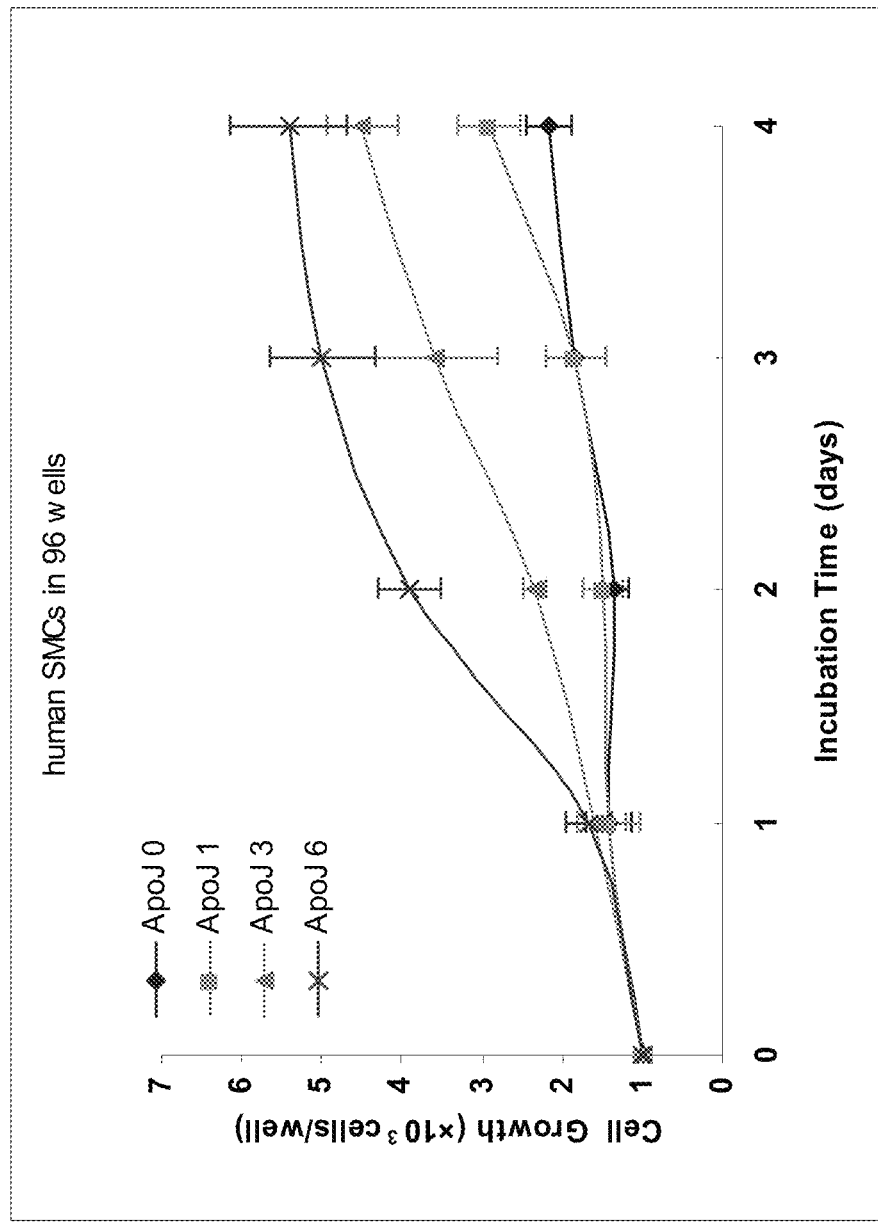
FIG. 8—Growth curves evidencing that incubation with recombinant clusterin analog stimulates proliferation of human vascular smooth muscle cells. Human smooth muscle cells (SMC) were incubated in DMEM media containing CluAg-I (1-6 µg/ml).
Figure 9:
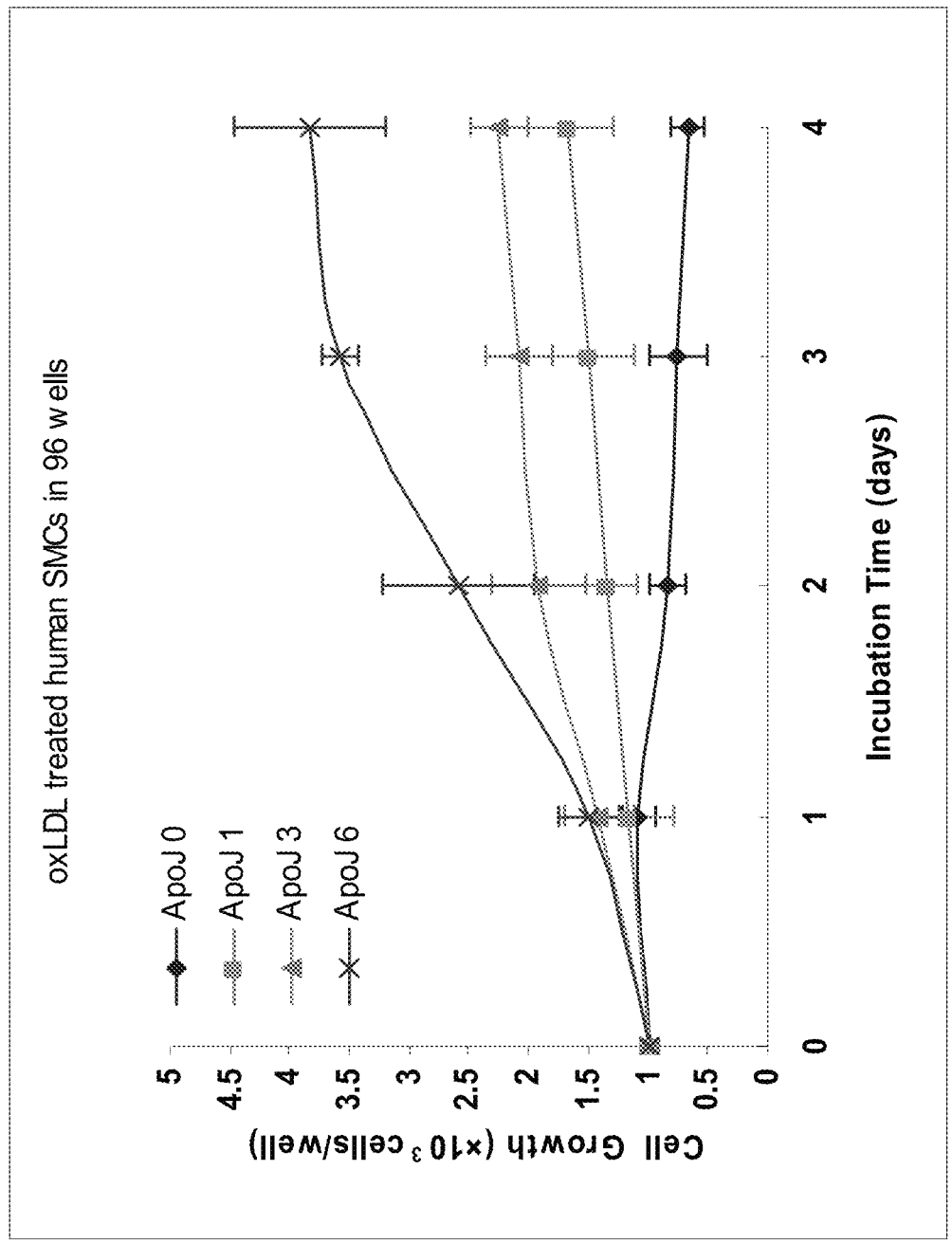
FIG. 9—Growth curves evidencing that incubation with recombinant clusterin analog blocks inhibitory effect of oxidized lipoprotein and stimulates proliferation of human vascular smooth muscle cells (SMCs). Human SMCs were incubated in DMEM media containing CluAg-I (1-6 µg/ml) in the presence of 50 µg/ml oxidized low density lipoprotein (oxLDL).

Clusterin analog regulation of vascular cell proliferation in culture. An in vitro system was first employed to examine the protective effects of clusterin analogs on survival and growth of vascular cells. Cells were treated with clusterin analogs at different concentrations in the cultures with or without oxidized LDL. After 2-4 days of stimulation, cell survival and proliferation were examined using a combination of techniques including flow cytometry, fluorescent microscopy, and radioactive isotope labeling, as described below. Control experiments were set up using other types of proteins, such as bovine albumin. FIGS. 8 and 9 show growth curves of SMCs treated with or without CluAg (1-6 μg/nl) in the presence or absence of oxLDL (50 μg/ml). Treatment with the analog increased SMC proliferation even under the condition of oxLDL exposure. CluAg dose-dependently increases SMC proliferation even in the presence of oxLDL (FIGS. 8 and 9).

Figure 10:
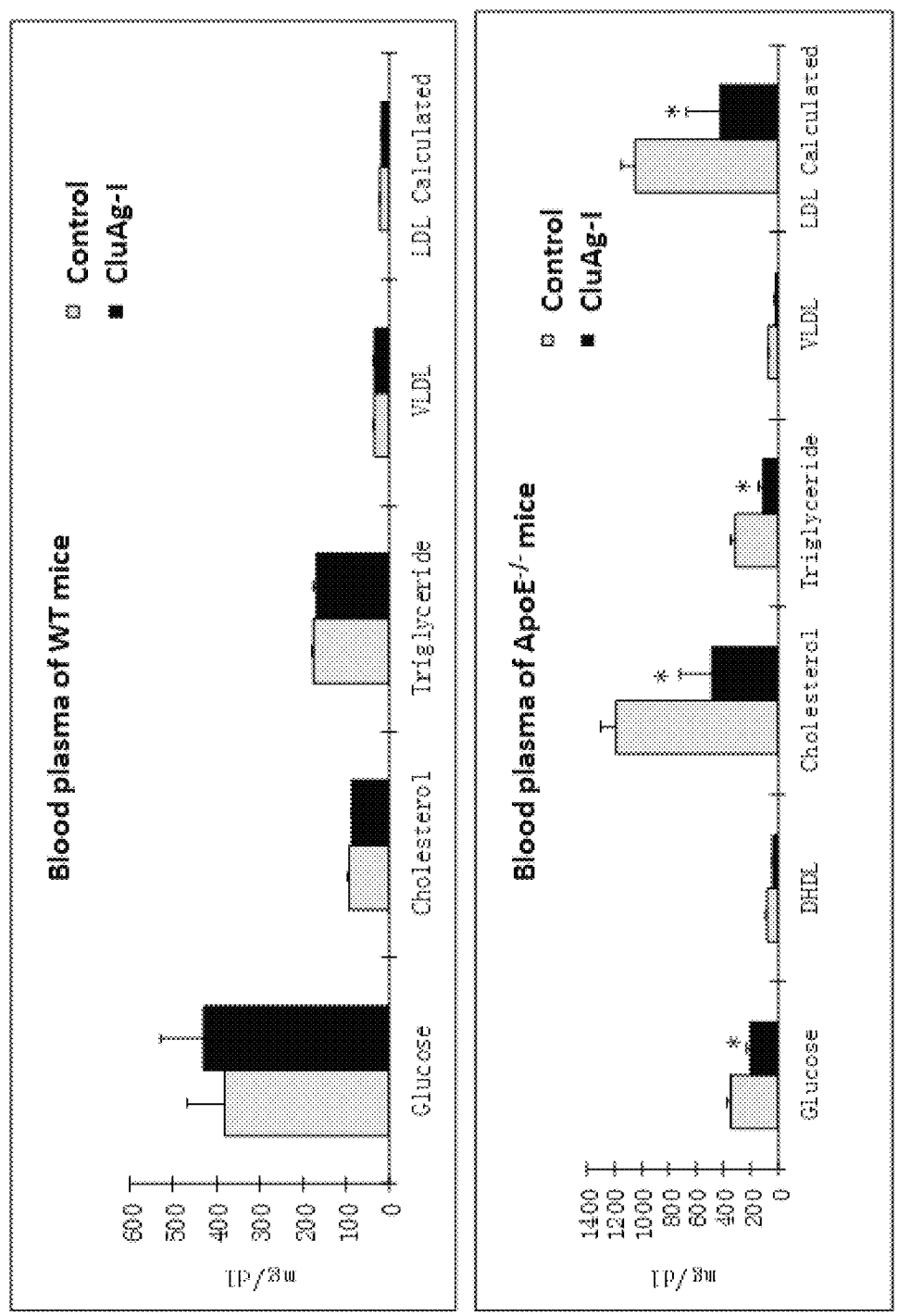
FIG. 10—Blood plasma comparison of WT mice (upper panel) and ApoE$^{-/-}$ mice (lower panel). Graphs show injection of human recombinant clusterin, CluAg-I, reducing blood levels of glucose, cholesterol, triglyceride, and LDL in ApoE$^{-/-}$ atherosclerosis-prone mice but not in age and sex-matched normal wild type (WT) control mice.

Analysis of lipid profiles, cholesterol, glucose, and triglyceride in wild type and atherosclerosis prone mice injected with clusterin. Weekly injection of CluAg (30-40 μg) for 3 months was conducted in wild type (WT) and apoE-null mice. The blood samples were collected, during tail DNA sampling, from the mice injected with CluAg. Serum was prepared from the blood samples. Cholesterol levels, lipoprotein profiles and clusterin concentrations were determined respectively. In brief, serum diluted in PBS was incubated in a 96 well plate coated with a rabbit polyclonal antibody to clusterin. After incubation and washing in PBS, bound clusterin was detected by incubating with mouse monoclonal antibody to clusterin. Goat anti-mouse IgG conjugated with peroxidase was used as the second antibody. Cholesterol and HDL was determined in the laboratory of Department of Laboratory Medicine. The ratio of clusterin vs. HDL was calculated after normalization with the lipid content. In addition to ELISA, immunoblotting assays were performed to verify the results. CluAg injection significantly reduced blood levels of total cholesterol, glucose, triglyceride, and LDL in apoE-null mice but no changes were found in WT mice (FIG. 10).

Figure 11:
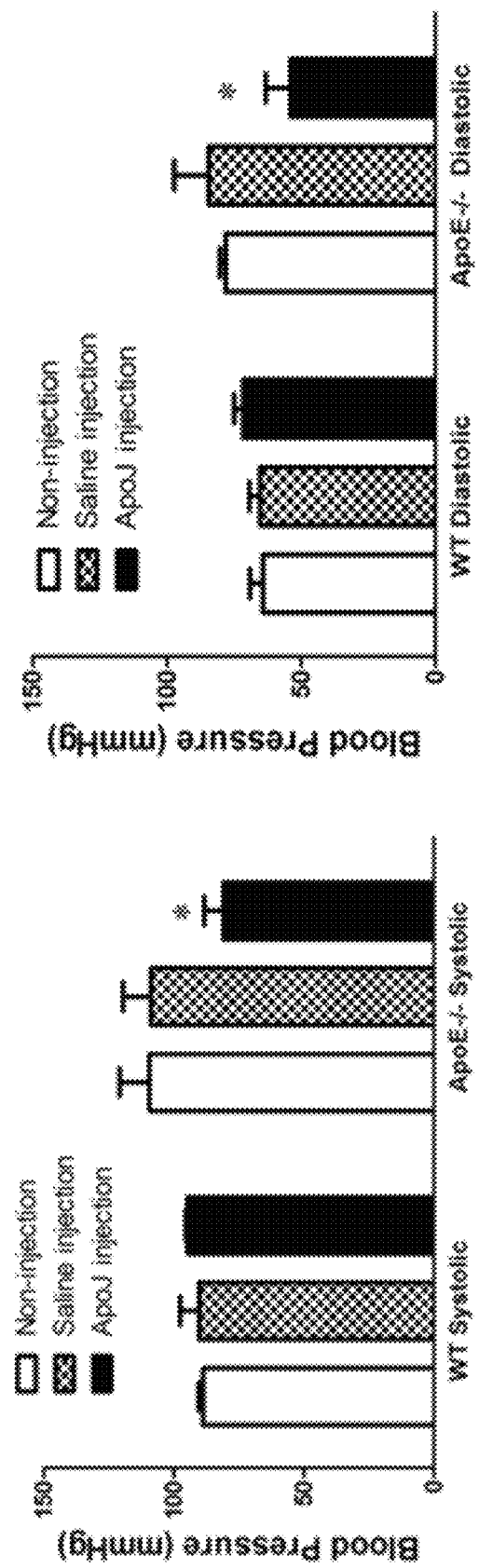
FIG. 11—Blood pressure comparison of WT mice and ApoE$^{-/-}$ mice. Graphs show intravenous injection of human recombinant clusterin analog, CluAg-I, for 3 months reducing both systolic and blood pressure in ApoE$^{-/-}$ atherosclerosis-prone mice but has no effect on that in age (6-8 months old) and sex (male)-matched normal wild type (WT) control mice.

Analysis of blood pressure. Blood pressure measurement was performed in the tail artery using a tail-cuff method. Each measurement was repeated 3 times to ensure reproducibility. Weekly injection of CluAg (30-40 μg) for 3 months led to reduction in the tail arterial blood pressure of both systolic and diastolic phases was conducted in apoE-null mice (FIG. 11, left panel) but no changes in blood pressure were found in WT mice (FIG. 11, right panel).

Figure 12:
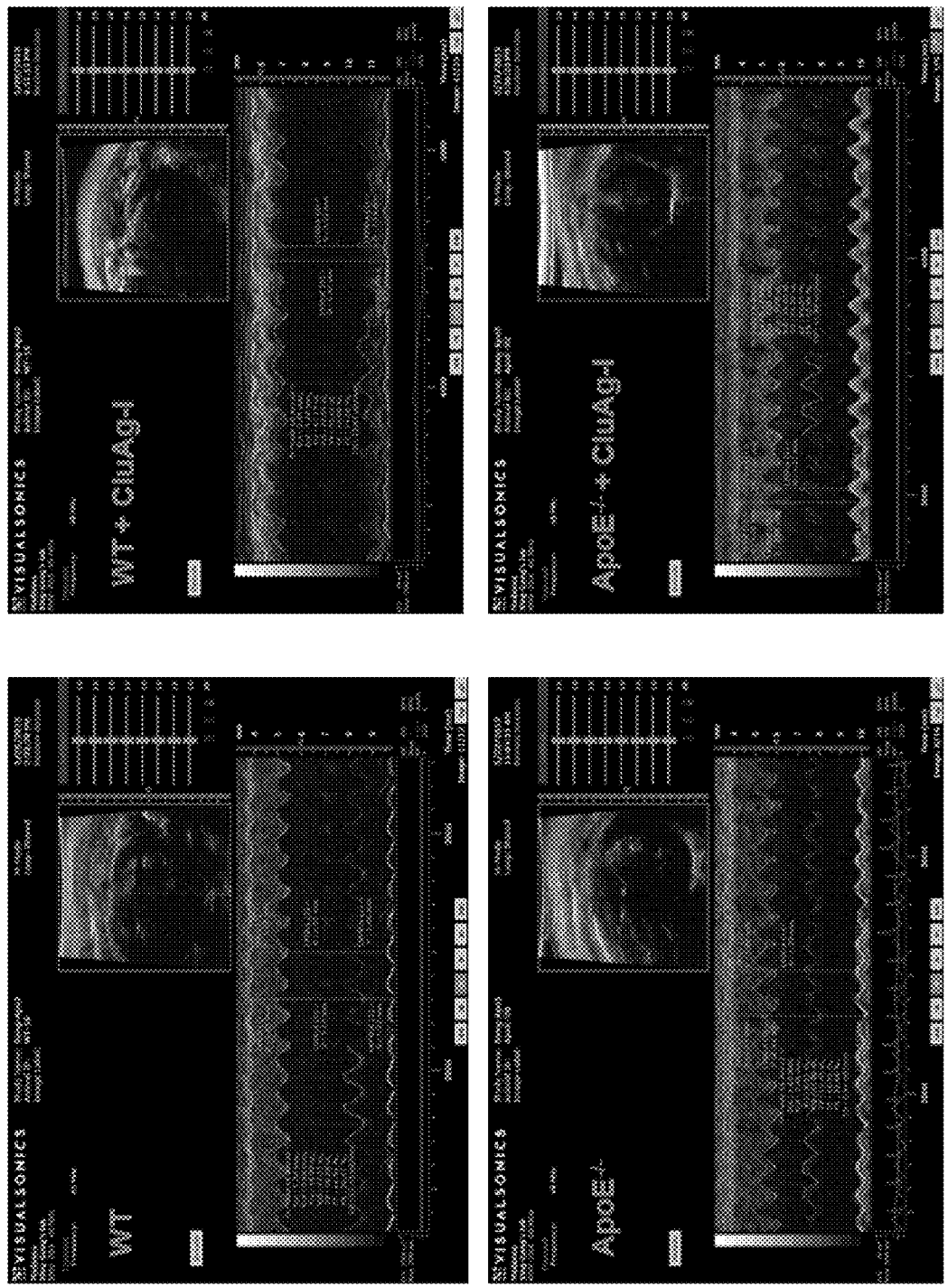
FIG. 12—Echocardiography of normal wild type (WT) and ApoE-/-mice with CluAg-I injection. WT and ApoE$^{-/-}$ mice were injected intravenously with CluAg for 3 months and then subjected to ultrasound examination using the Visualsonics™ echo device.
Figure 13:
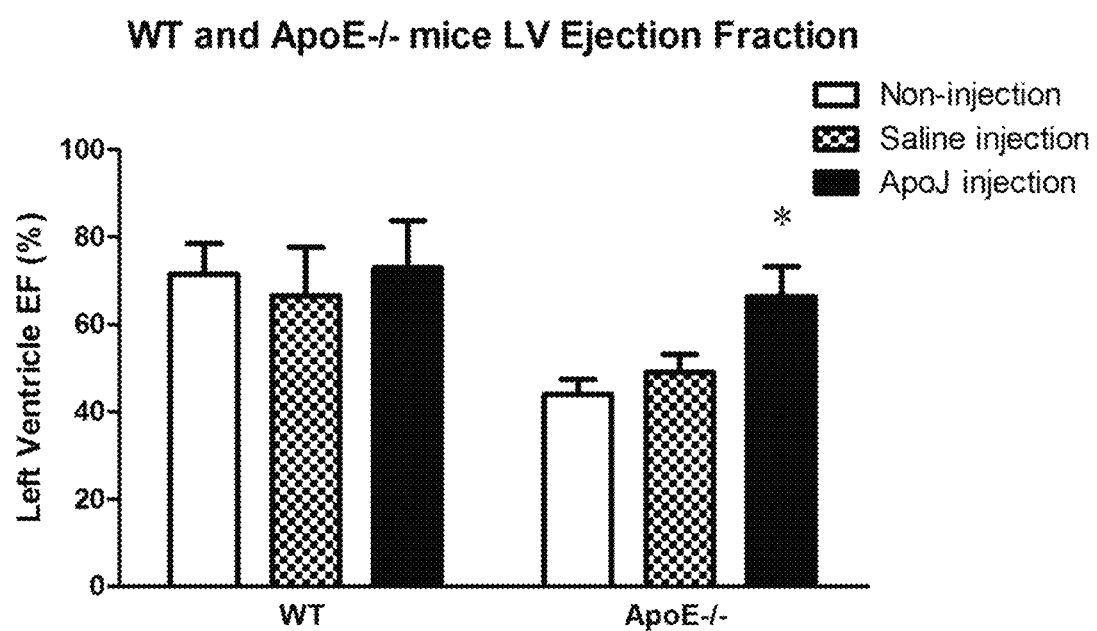
FIG. 13—Left ventricle ejection fraction comparison of WT mice and ApoE$^{-/-}$ mice. Intravenous injection of human recombinant clusterin analog, CluAg-I, for 3 months reduces blood pressure in ApoE$^{-/-}$ atherosclerosis-prone mice but not in age (6-8 months old) and sex (male)-matched normal wild type (WT) control mice.

Echocardiography of mice injected with CluAg. After weekly injection of CluAg, morphological and functional changes were monitored using echocardiography. B- and M-Mode echocardiography was performed one, 6, 10, and 18 weeks after injection. The echocardiography studies were conducted actually using ultrasonography as the murine heart is small. Mice were anesthetized with ketamine and xylazine, chests shaved and a layer of acoustic coupling gel will be applied to the thorax. A dynamically focused 9-MHz annual array transducer was applied using a warmed saline bag as a standoff. All echo studies were performed using a state of the art echo machine (HP Model Sonos 5500 HP). Area fractions were determined by planimetry of diastolic and systolic volumes in parasternal short axis. The LV end-diastolic and end-systolic dimensions were measured using the M-Mode from >3 beats by two independent investigators blinded to the research animals. LVEF (left ventricular ejection fraction) was calculated as follows: LVEF=[(LVIDd)−(LVIDs)]/(LVIDd), LVIDd: end-diastolic left ventricular internal diameter; LVIDs: end-systolic left ventricular diameter. FIG. 12 shows ultrasound images of murine hearts with or without CluAg injection in both 2D and M-mode. FIG. 13 demonstrates that weekly administration of CluAg (30-40 µg/mouse) increases ejection fraction in the hearts of ApoE−/− atherosclerosis-prone mice but no changes in wild type mice with the same dose CluAg.

Oil red O staining of aortic wall. Mice were sacrificed 3 months after CluAg treatment. Aortas were opened across the long axis and fixed in 10% buffered formalin for histological evaluation. Aortas were stained with Oil Red O solution for assessing neutral lipid contents. Little staining was detected in WT aortas. However, compared to WT aortas, the ApoE-null aortas were stained very intensively with Oil Red O, which visualizes atherosclerotic plaques. Decreased Oil Red O stains were found in ApoE-null mice injected with CluAg protein (FIG. 14).

Figure 15:
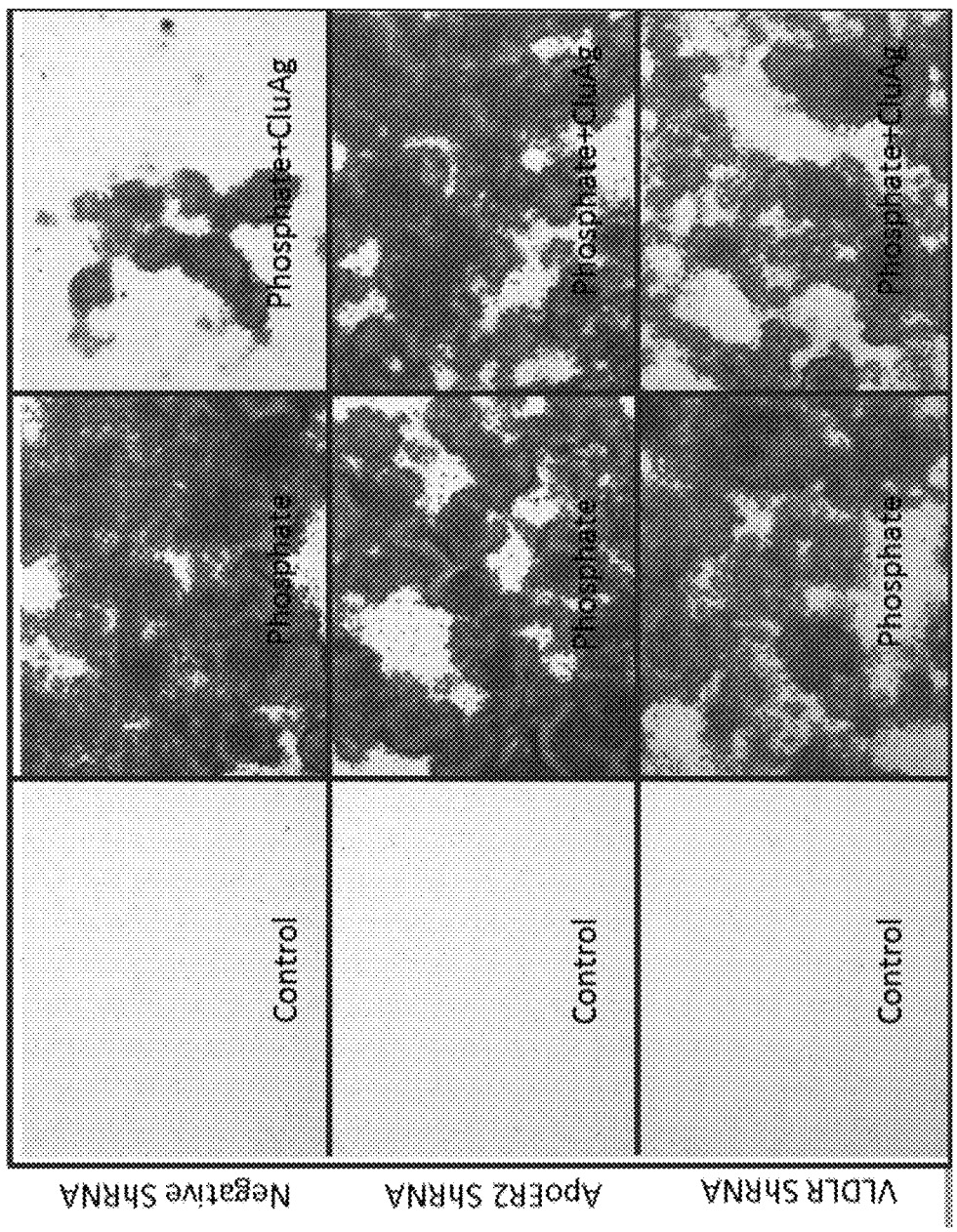
FIG. 15—Alizarin Red staining of murine vascular smooth muscle cells evidence that CluAg reduces phosphate-induced calcification of ApoE$^{-/-}$ SMCs in a matter dependent upon expression of ApoER2 and VLDLR. SMCs treated with ApoER2 or VLDLR shRNA were incubated with Pi (3.6 mmol/L)+/- CluAg in DMEM containing 5% FBS for 6 days. At the end of culture cells were washed in PBS, fixed in 10% formalin, and stained in 2% Alizarin Red at 37° C. for 10 min. Reduced Alizarin Red staining could be partly blocked by ApoER2 and VLDLR shRNA.
Figures 16A, 16B, 16C:
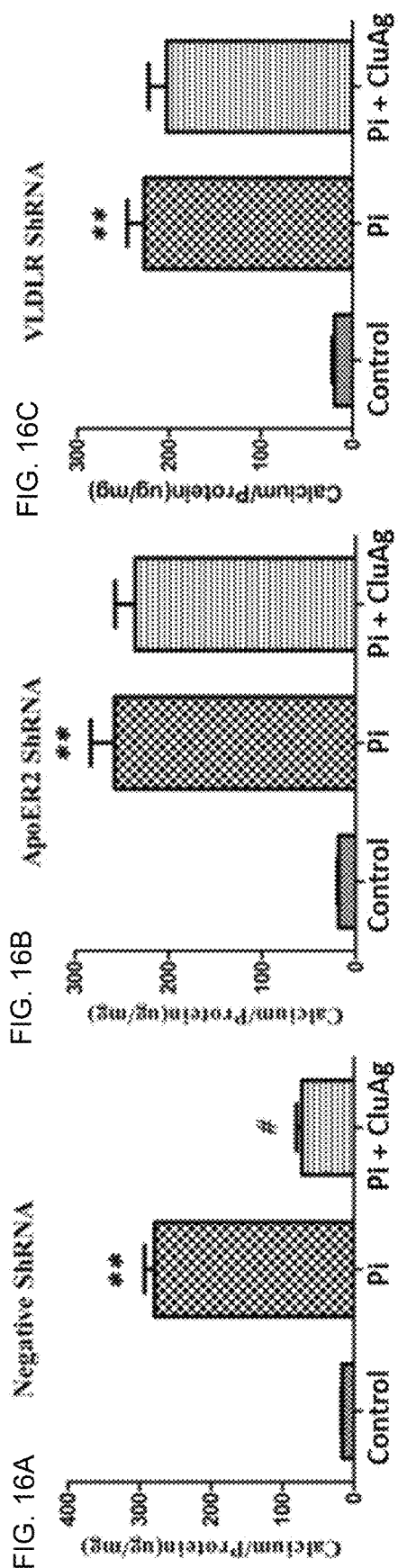
FIGS. 16A-16C—Graphs show that CluAg treatment reduces phosphate-induced (Pi) calcification in ApoE$^{-/-}$ vascular smooth muscle cells (SMCs) in a manner dependent upon expression of ApoER2 and VLDLR. SMCs treated with ApoER2 or VLDLR shRNA were incubated with Pi (3.6 mmol/L) in the presence or absence of CluAg (6 µg/ml) in DMEM containing 5% FBS for 6 days. In the end of culture cells were washed in PBS, incubated in 0.6M HCl overnight. Cell lysates were mixed with 0.1N NaOH was used to lysis cells and concentrations of proteins were measured. Supernatants were collected, and calcium contents measured using a calcium assay; were mixed with 90 µl of the Chromogenic Reagent, and 60 µl of the Calcium Assay Buffer, mix gently; Incubated the reaction for 5-10 mins at room temperature, protected from light; Measured OD at 575 nm. 16A, SMCs treated with negative control ShRNA; 16B, with ApoER2 ShRNA; and 16C, with VLDLR ShRNA. Data represent means+/-S.D., **, p<0.01 and #p<0.05.
Figures 17A, 17B, 17C, 17D:
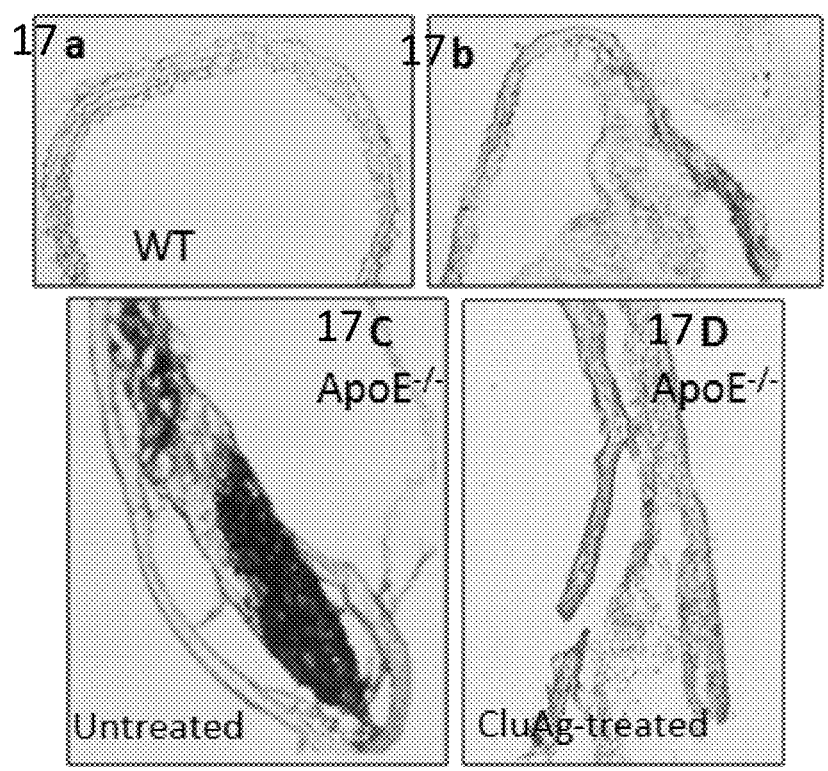
FIGS. 17A-17D—Alizarin Red staining showing that weekly intravenous injection of human recombinant clusterin analog, CluAg for 3 months inhibits atherosclerosis as well as calcification in ApoE$^{-/-}$ atherosclerosis-prone mice. 17A shows wild type (WT) control mice. Aortas were stained in 2% Alizarin Red at 37° C. for 10 min. Images were taken using ×4 objective for 17A and 17B, and ×10 objective for 17C and 17D. Reduced plaque size and Alizarin staining in ApoE-/- mice treated with CluAg was observed.
Figures 18A, 18B, 18C, 18D, 18E, 18F, 18G, 18H:
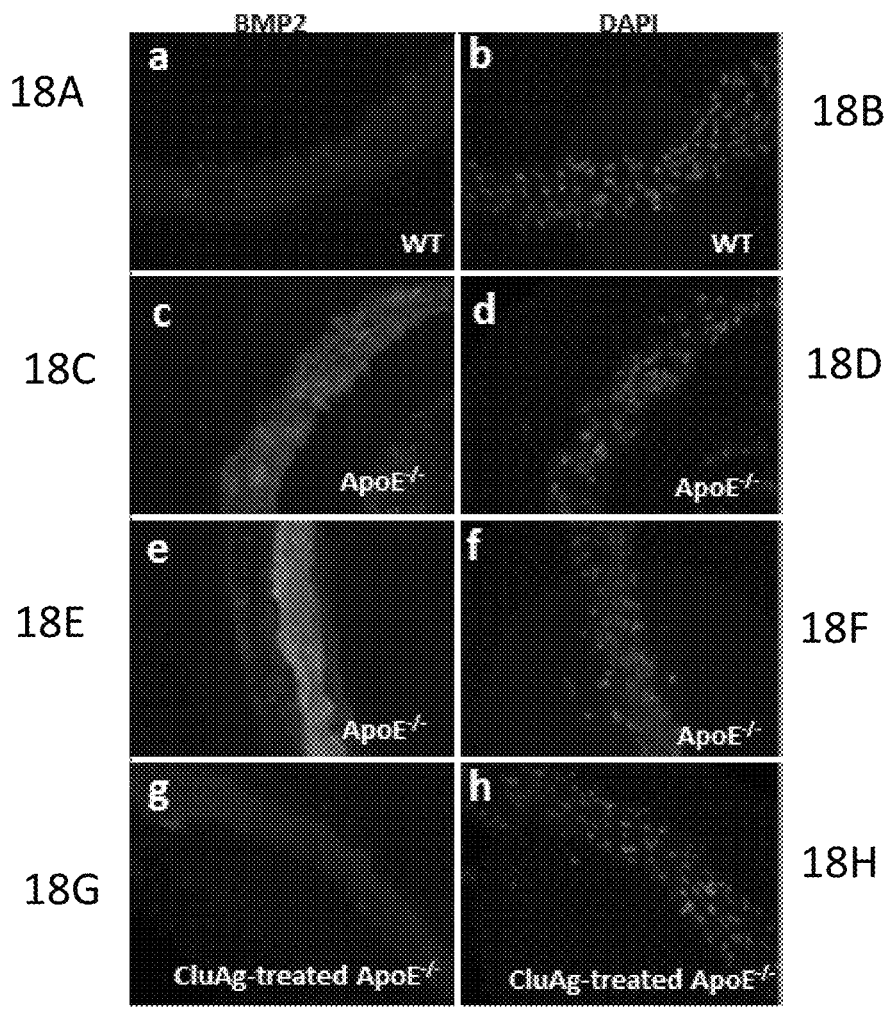
FIGS. 18A-18H—Immunofluorescence of bone morphogenic protein-2 (BMP2) in aortas of wild type (WT) mice and ApoE−/− mice treated with or without CluAg. Again, results show that CluAg treatment is able to reduce BMP2 expression in ApoE−/−mice.

Analysis of aortic tissue and cell calcification. Aortic smooth muscle cells (SMCs) were incubated with CluAg in the presence of sodium phosphate (3.6 mmol/L) for 6 days. Alizarin red S (Sigma, St. Louis, Mo., USA) staining assesses calcium deposition in a reaction in which Alizarin red S dye binds with Ca ions in cell layer matrix. Cells were fixed with 2% paraformaldehyde and stained with 1% Alizarin red S (pH 4.2). The culture plates were photographed under a light microscope and assessed for the mineralized nodules which shown as red (FIG. 15). CluAg treatment markedly reduces calcification in SMCs. To determine if clusterin receptors mediate the inhibitory effect of CluAg on phosphate induced calcification in SMCs, snRNA for ApoER2 and VLDLR, two known receptors for clusterin, was constructed and used to knock down ApoER2 and VLDLR. CluAg treatment had no inhibitory effect on calcification in SMCs with the receptor knockdown with the snRNA (FIG. 15). This result was confirmed by direct calcium assays (FIGS. 16A-C). For assessing in vivo calcification of aortic tissue, Alizarin red S staining was performed in the aortas of WT and apoE-null mice with CluAg injection. Sections of aortas from apoE-null mice but not wild type control mice show the development of atherosclerotic plaques. Calcium deposits were highly abundant in ApoE-null mice. Treatment with CluAg reduces calcification in ApoE-null mice (FIGS. 18A-H).

Immunohistochemistry of aortic tissue. In order to assess whether CluAg injection alters expression of calcification-regulatory proteins, such as bone morphogenic protein (BMP)-2, in the aortic tissue, aortic sections were stained with anti-BMP-2 antibodies. Immunofluorescence for BMP-2 was developed with rhodamine-conjugated second antibodies (Sigma, St. Louis, Mo.). The slides were mounted in the Vectashield mounting medium with 4′,6 diamidino-2-phenylindole (DAPI) (Vector, Burlingame, Calif.), and examined under an Olympus fluorescence microscope. Intensive BMP-2 immunofluorescence was found in ApoE-null aorta but CluAg injection reduced the intensity of the BMP-2 fluorescence.

Example 2—Further Analysis of Clusterin In Vivo

Methods and Materials

Cell culture. Aortic VSMCs were isolated from 5- to 6-week-old male ApoE−/− or WT mice with C57BL/6 background. The cells were maintained in Dulbecco's Modified Eagle's Medium (DMEM; Invitrogen, Carlsbad, Calif., USA) supplemented with 10% fetal bovine serum (FBS) with 100 ng/mL penicillin and streptomycin (Invitrogen) at 37° C. in a humidified atmosphere with 5% CO2. Calcification medium was made by adding $NaH_2PO^4$ (pH adjusted to 7.4) into 5% FBS medium to obtain a final concentration of 3.6 mM inorganic phosphate. VSMCs from passage 5-10 were used. Apo J Medium was replaced every 2 or 3 days for up to 9 days. Cells maintained in regular culture medium with 0.9 mM phosphate were used as controls.

Lentivirus infection and selection. To generate a stable (long-term) knockdown of ApoER2 or VLDLR gene expression in VSMCs, the VSMCs were infected with lentivirus particles containing a pLKO.1 vector with the information to express a shRNA against mouse ApoER2 or VLDLR. This plasmid also has a puromycin resistance gene, thereby allowing for the selection of cells stably expressing desired shRNA by addition of puromycin into culture medium. The optimal puromycin concentration for VSMCs before initiating the experiments (titration assay) was determined to be 1 µg/ml. To perform lentivirus infection, cells approximately 80% confluent were used. 1.5 ml of fresh culture media containing virus was added onto cells. Fresh media was changed every 3 days 48 h after infection. To select the infected cells, selection media containing puromycin was used for culture 48 h after infection. ApoER2 and VLDLR knockdown were monitored by western blot analysis and was achieved after four passages. One plate of cells infected with pLKO.1 vector with shRNA verified to contain no homology to known mammalian genes was maintained in parallel. This plate served as a negative control for following experiments.

Calcium determination. Calcium content in VSMCs was determined by colorimetric calcium detection kit (Abcam). Cells were washed with PBS and then incubated with 0.6M HCl under 37° C. overnight to be decalcified. The calcium content in the supernatants was measured using spectrometer. Then cells were lysed with 0.1 mol/LNaOH/0.1% SDS. Protein content was determined with BCA protein assay kit (Thermo Scientific) and calcium content was normalized to total protein content.

Alizarin Red S staining. Cells were fixed in 2.5% glutaraldehyde and incubated with 2% Alizarin Red S under 37° C. for 15 minutes. Then VSMCs were rinsed with PBS three times. Calcium mineralization visualized by red staining was observed under microscope.

Real-time RT-PCR. Total RNA was extracted from VSMCs using Trizol (Invitrogen). 4 µg total RNA was used for cDNA synthesis in a reaction mixture of 204, with SuperScript III First-Strand Synthesis SuperMix (Invitrogen). Real-time PCR amplification was performed with IQ™ SYBR Green Supermix (Bio-Rad) in a ICYCLERIQ™ thermocycler (Bio-Rad). The following primers sets were used:

```
ALP,
                      (sense; SEQ ID NO: 18)
5'-CACAATATCAAGGATATCGACGTGA-3'
and
```

(antisense; SEQ ID NO: 19)
5'-ACATCAGTTCTGTTCTTCGGGTACA-3';

BMP-2,
                                    (sense; SEQ ID NO: 20)
5'-TTGTATGTGGACTTCAGTGATGTG-3'
and (antisense; SEQ ID NO: 21)
5'-AGTTCAGGTGGTCAGCAAGG-3';

Osteopontin,
                                    (sense; SEQ ID NO: 22)
5'-TGGCTATAGGATCTGGGTGC-3'
and (antisense; SEQ ID NO: 23)
5'-ATTTGCTTTTGCCTGTTTGG-3';
and Runx2,
                                    (sense; SEQ ID NO: 24)
5'-TTACCTACACCCCGCCAGTC-3'
and (antisense; SEQ ID NO: 25)
5'-TGCTGGTCTGGAAGGGTCC-3'.

Western blot. Proteins were isolated from VSMCs using RIPA buffer (Pierce) containing protease and phosphatase inhibitors (Sigma-Aldrich). Proteins separated on 10% SDS-Polyacrylamide gel were transferred to polyvinylidenedifluoride (PVDF) membranes (Millipore) and Western blot was performed using the standard protocol. Membranes were blocked with 5% bovine serum albumin (BSA) in TBS containing 0.1% Tween-20 (TBST). Primary antibodies were diluted in 3% BSA [goat anti-ApoJ 1:1000 (Santa Cruz Biotechnology), rabbit anti-Runx2 1:1000 (Cell Signaling), goat anti-SM22α 1:5000 (Abcam), rabbit anti-αSMA 1:1600 (Abcam), rabbit anti-GAPDH 1:30000 (Abcam)] and were detected using HRP-conjugated secondary antibodies [donkey anti-goat 1:5000 (Santa Cruz Biotechnology), goat anti-rabbit 1:20000 (Santa Cruz Biotechnology)] diluted in 3% BSA in TB ST.

Data analysis and statistics. Western blot results were analyzed by densitometry using Scion Image (Scion Corp). Real-time polymerase chain reaction data was quantified using EXCEL® software (Microsoft Corp). Values were graphed as mean±SD of at least triplicates determinations. Statistics (t test and ANOVA) were performed using Graphpad software (Graphpad Software Inc). A value of P<0.05 was considered statistically significant.

Results

Figure 19A:
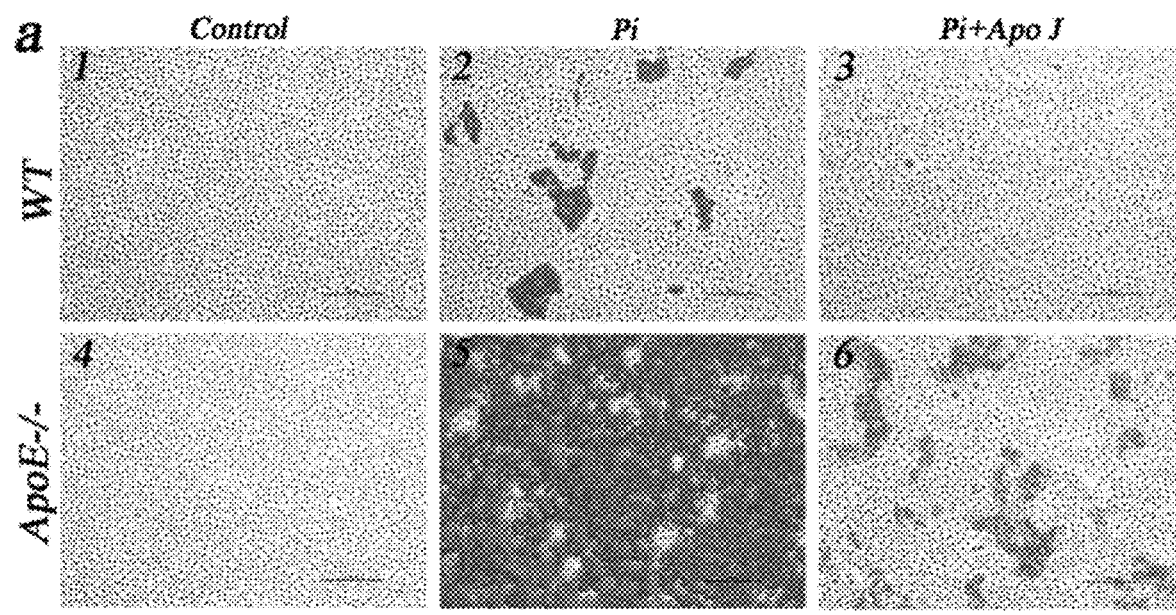
FIGS. 19A-19B—Calcium deposit in smooth muscle cells (SMC) isolated from aorta of WT and ApoE-null mice. ApoE−/− VSMCs are more prone to Pi-induced calcification. Alizarin red staining (19A) and calcium assay (19B) of VSMCs isolated from aorta of WT and ApoE-/-mice. Scale bar=200 μm.VSMCs from WT and ApoE-/-mice were treated with inorganic phosphate (Pi) with or without Apo J (6 μg/mL). Bars represent means±SD, n=5, *P<0.05 vs. control; **P<0.01 vs. control; #P<0.05 vs. Pi group; ##P<0.01 vs. Pi group.
Figure 19B:
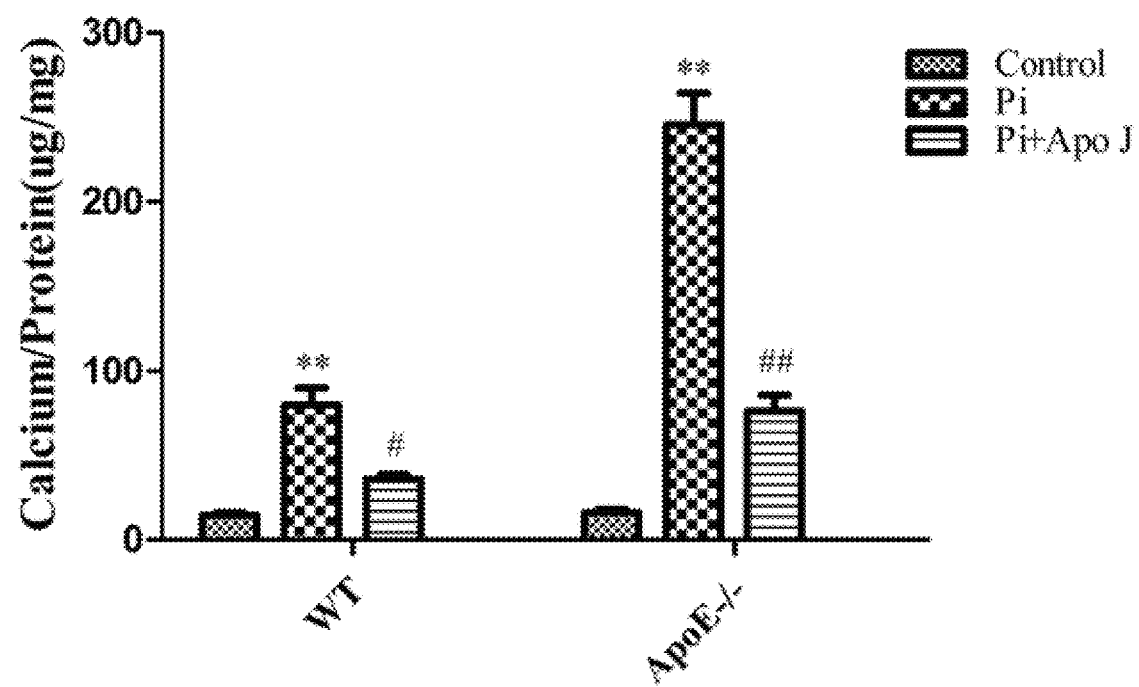
Figure 20A:
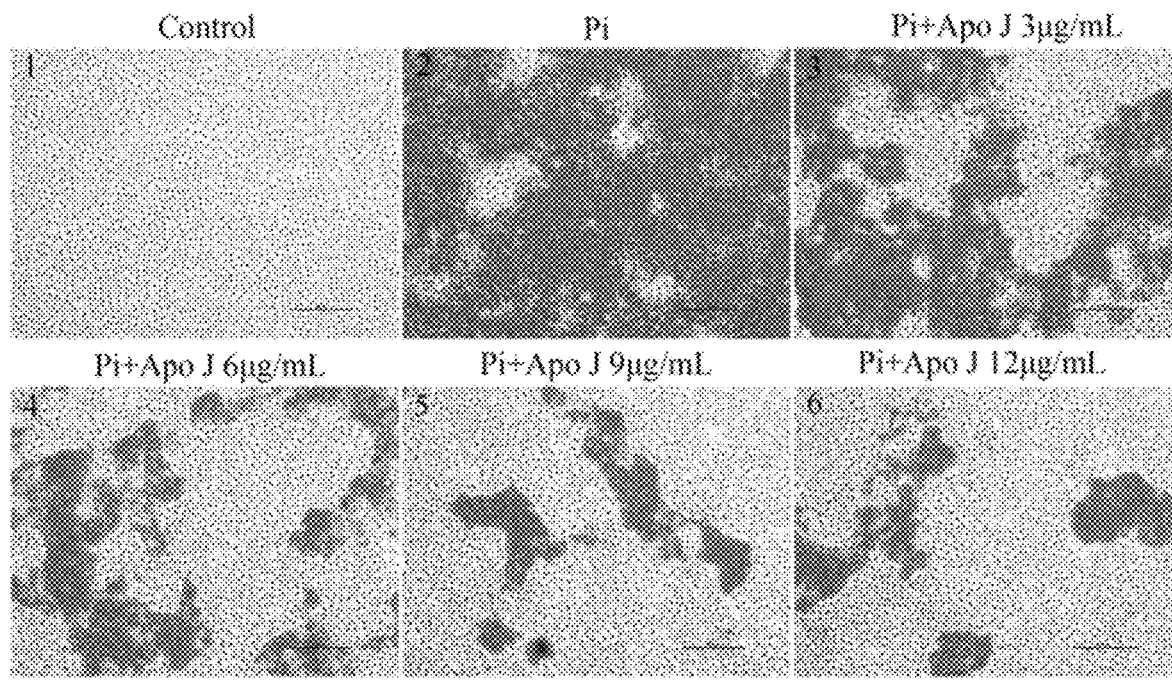
FIGS. 20A-20B—Calcium deposit in SMC treating with or without Apo J. Inhibitory effect of Apo J on calcification in ApoE−/− VSMCs is correlated to concentration of Apo J. a: Alizarin S staining of VSMCs from ApoE-/-mice. VSMCs were treated with different concentrations of Apo J (0-12 μg/mL) during calcification. Scale bar=200 μm. b: Calcium assay of ApoE−/− VSMCs treated with various concentrations of Apo J (0-12 μg/mL) and Pi. Bars represent means±SD; n=5 per group. **P<0.01 vs. control; ##P<0.01 vs. Pi group.
Figure 20B:
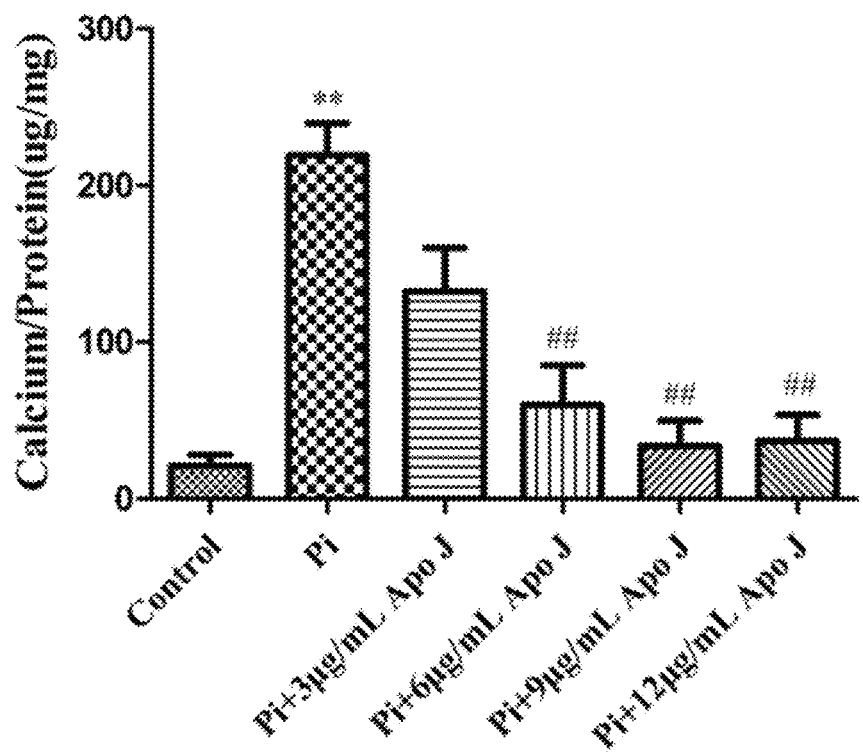

Apo J attenuates calcification in both ApoE−/− and WT smooth muscle cells. Because ApoE−/−mice are more prone to vascular calcification than WT ones, the responses of ApoE−/− and WT VSMCs to inorganic phosphate (Pi) were examined as well as the effect of Apo J on calcification of these two groups of cells. The study shows that when induced with Pi, ApoE−/− VSMCs exhibited much higher levels of calcification on day 6 of treatment than WT cells. The addition of Apo J (6 µg/mL) into culture medium reduced calcium level in both groups, with a more dramatic inhibition on calcification in ApoE−/− VSMCs, shown by both Alizarin S staining (FIGS. 19A and 20A) and calcium assay (FIGS. 19B and 20B). Therefore, additional experiments were conducted using ApoE−/− VSMCs. Various concentrations (3 µg/mL, 6 µg/mL, 9 µg/mL, and 12 µg/mL) of Apo J were then applied to test if the suppressive effect of the Apo J on vascular cell calcification is dose dependent. The data demonstrated that 6 µg/mL Apo J in culture is sufficient to significantly decrease calcium deposition level in ApoE−/− VSMCs, while 12 µg/mL is incapable to further attenuate calcification compared to 9 µg/mL group (FIG. 20B), possibly due to saturation of Apo J receptors.

Figures 21A, 21B, 21C, 21D:
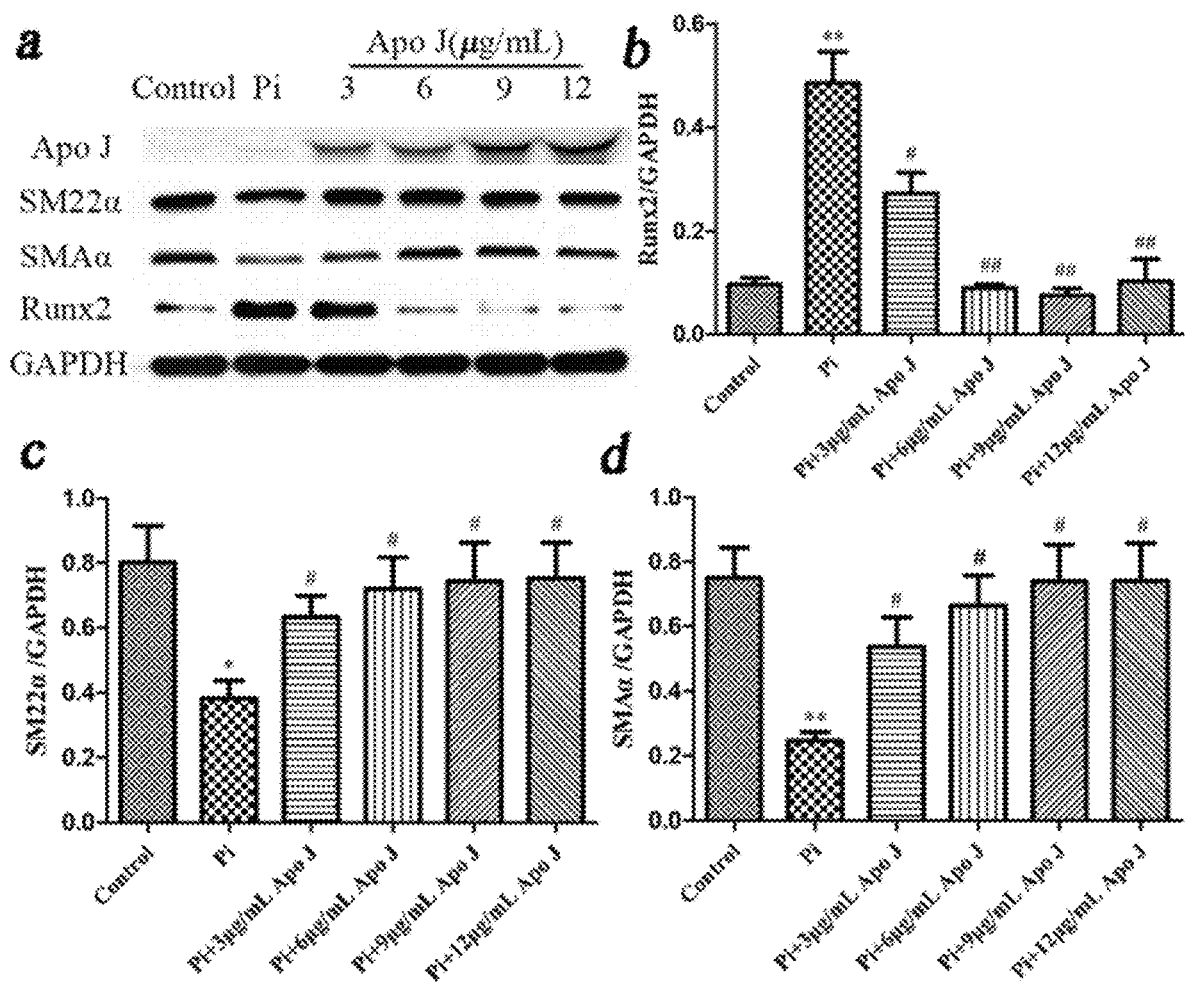
FIGS. 21A-21D—Apo J modulates the protein expression of smooth muscle lineage-specific markers and calcification-related genes. VSMCs were treated with Pi and Apo J (0-12 μg/mL). 21A: 40 μL cell culture medium was used to detect the level of Apo J in culture medium. Levels of SM22α, αSMA and Runx2 protein expressions were assessed by western blot. GAPDH was used as the loading control. 21B-21D: Densitometry analysis shows the quantification of SM22α, αSMA and Runx2. Bars represent means±SD; n=5 per group. *P<0.05 vs. control; **P<0.01 vs. control; #P<0.05 vs. Pi group; ##P<0.01 vs. Pi group.
Figures 22A, 22B:
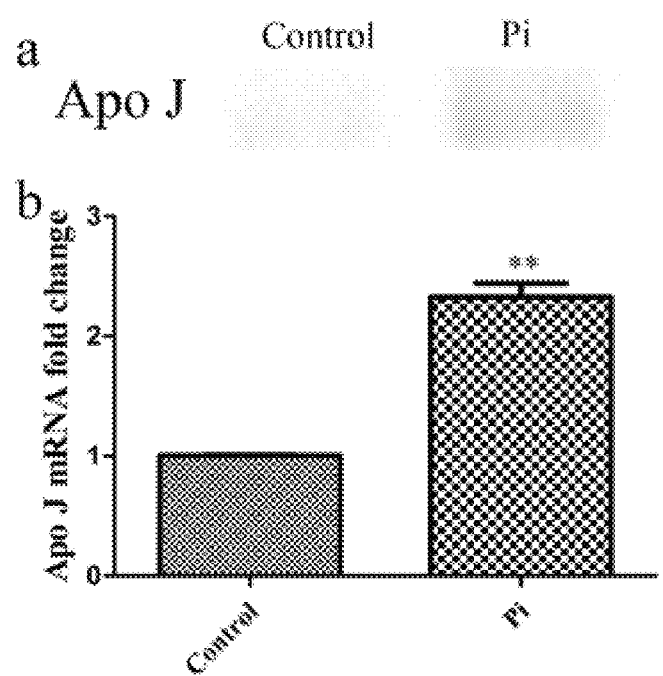
FIGS. 22A-22B—Expression of Apo J during calcification. 22A: 40 μl cell culture medium was used to detect the expression of Apo J by Western blot. 22B: Apo J mRNA expression was detected by qRT-PCR. GAPDH was used as an internal control. Bars represent means±SD; n=3 per group. *P<0.05 vs. control; **P<0.01 vs. control.
Figures 23A, 23B, 23C, 23D:
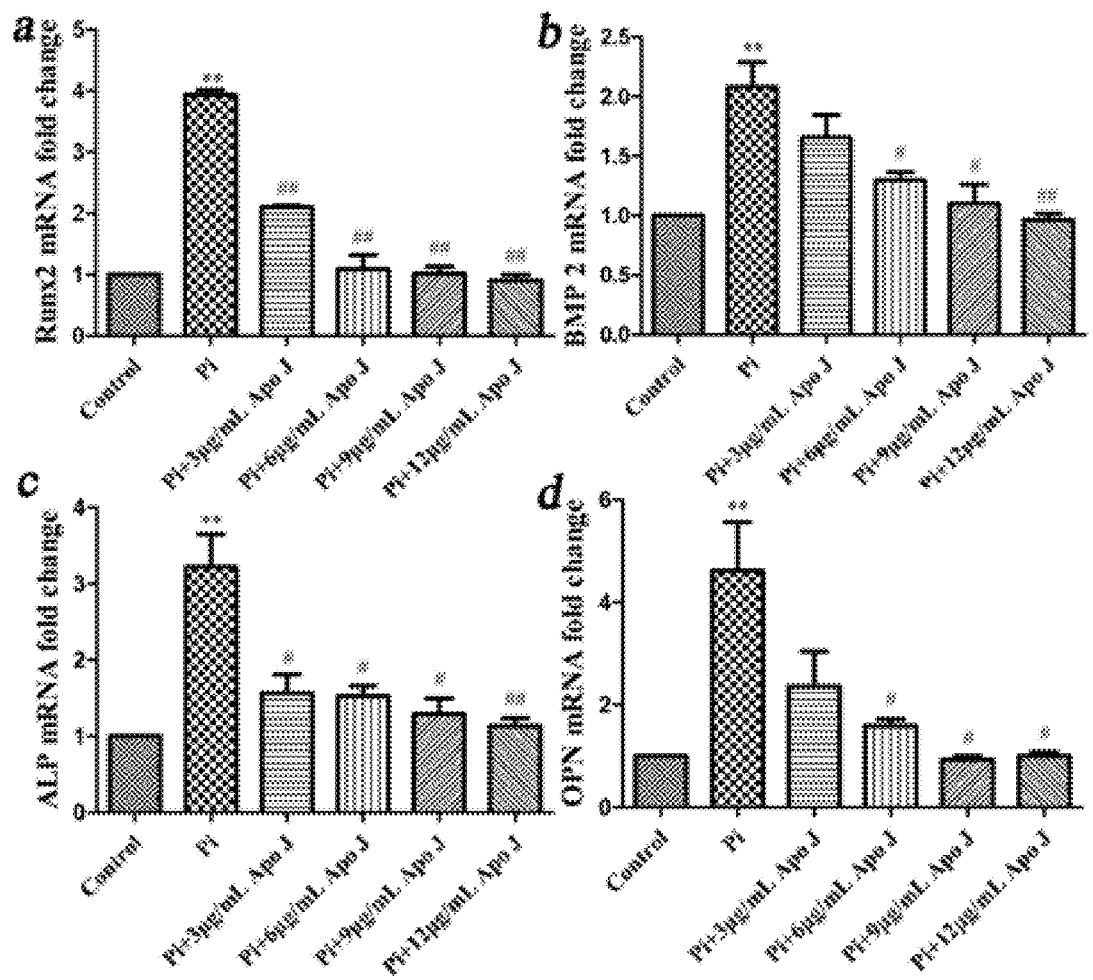
FIGS. 23A-23D—Apo J affects osteogenetic markers on mRNA levels during calcification. VSMCs were treated with Pi in combination with Apo J (0-12 μg/mL). Runx2 (23A), BMP-2 (23B), ALP (23C), and OPN (23D) mRNA expressions were quantified by qRT-PCR and normalized to GAPDH as an internal control. Bars represent means±SD; n=5 per group. **P<0.01 vs. control; #P<0.05 vs. Pi group; ##P<0.01 vs. Pi group.
Figures 24A, 24B, 24C, 24D, 24E, 24F:
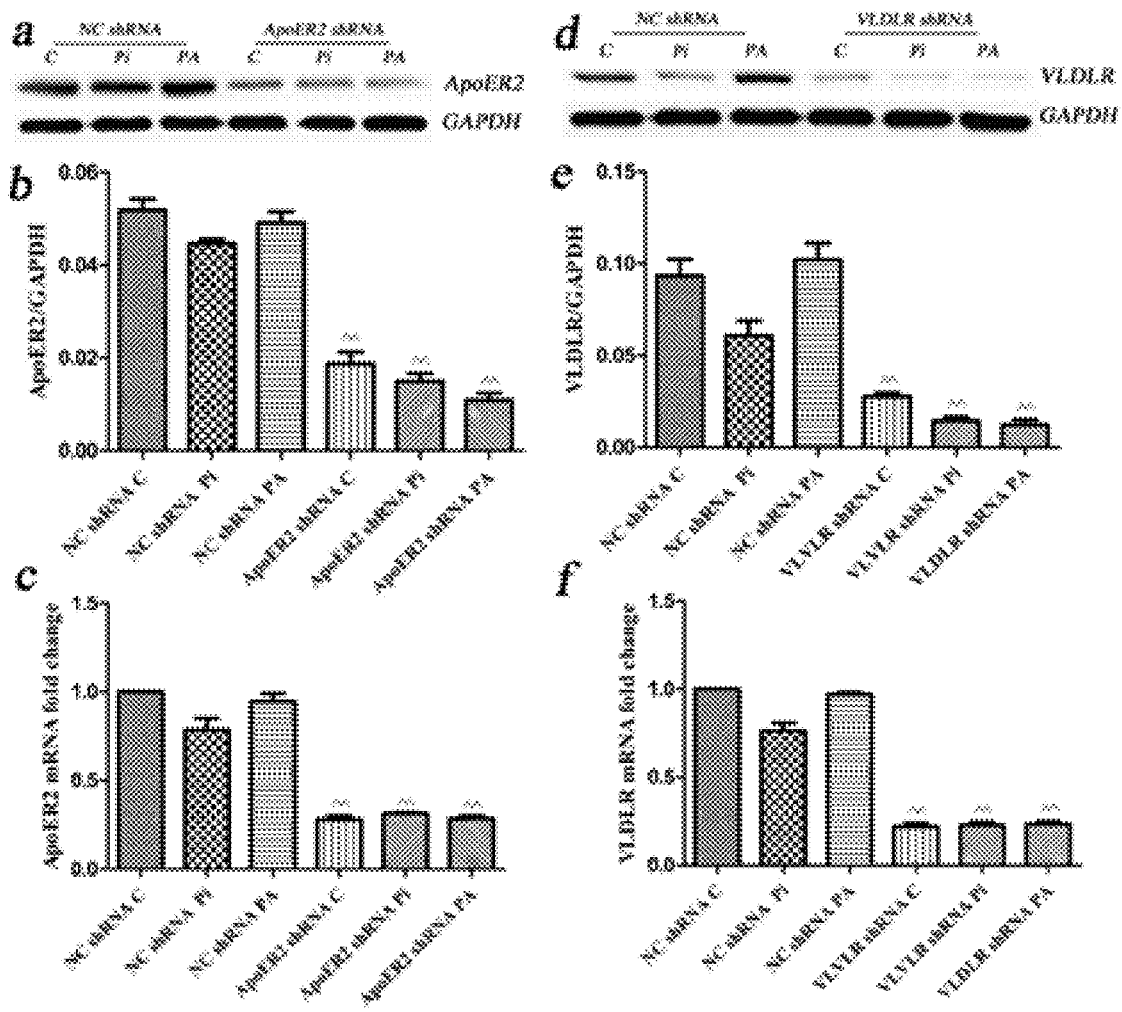
FIGS. 24A-24F—Lentiviral shRNA knockdown of ApoER2 and VLDLR receptors. 24A-24B: ApoE−/− cells were transfected with ApoER2 shRNA, VLDLR shRNA or negative control shRNA to collect whole-cell lysates for western blot analysis of ApoER2 or VLDLR. 24C-24D: Densitometry analysis shows the quantification of ApoER2 or VLDLR expression. 24E-24F: Bar graph illustrating real-time PCR data demonstrating that ApoER2 or VLDLR was successfully knocked down on mRNA level. Relative mRNA expressions were normalized to GAPDH as an internal control. Bars represent means±SD; n=3 per group. *P<0.05 vs. control, **P<0.01 vs. control; #P<0.05 vs. Pi group, ##P<0.01 vs. Pi group.

Apo J modulates osteogenesis-related genes during calcification in ApoE−/− VSMCs. To confirm the effect of Apo J on calcification, the change of osteogenesis regulator Runx2 was assessed, as well as the smooth muscle lineage markers SM22α and αSMA, with or without added Apo J during calcification of ApoE−/− VSMCs, which were treated with Pi for 6 days. Concentrations from 3 µg/mL to 12 µg/mL of Apo J were used. Equal volumes (40 µL) of culture medium were immunoblotted with Apo J antibody at the endpoint of the experiment to verify the existence of Apo J protein in medium. The data suggested that both the mRNA level and the native secreted form of Apo J increased in calcifying cells (FIGS. 21A and 22A-B); addition of Apo J resulted in a much stronger signal detected by Apo J antibody, indicating Apo J in medium was sustained on a potent level compared to control group and not subject to bulk degradation through the period of experiment. It was found Runx2 was increased in response to Pi and this increase was attenuated in all Apo J treated groups, with 6 µg/mL Apo J sufficient to keep Runx2 protein expression down to approximately the same level in uncalcified cells. No significant differences of Runx2 levels were observed between 6 µg/mL, 9 µg/mL, and 12 µg/mL groups (FIGS. 21A-21B). SM22α and αSMA protein expressions were downregulated by Pi compared to control group; Apo J rescued the decreased level of SM22α and αSMA at a concentration as small as 3 µg/mL (FIGS. 21A, 21C and 21D). mRNA expressions of osteogenic genes including Runx2, BMP-2, OPN and ALP were increased during calcification while Apo J weakened this effect (FIGS. 23A-23D).

Knockdown of apolipoprotein-E receptor 2 (ApoER2 or very low density lipoprotein receptor (VLDLR) abolishes the inhibitory effect of Apo J on calcification. Because 6 µg/mL of Apo J has been shown to inhibit calcium mineralization as well as activation of calcification-associated genes, this same concentration of Apo J was used to treat VSMCs in remaining experiments. Apo J receptors ApoER2 and VLDLR were knocked down in ApoE−/− VSMCs by lentiviral shRNA. Knockdown effect was confirmed by western blots and qRT-PCR. The data demonstrated that the knockdown of VLDLR or ApoER2 itself didn't change calcification level under the influence of Pi. The negative control shRNA didn't alter the sensitivity of VSMCs to Apo J in calcification and calcium amount still decreased in Apo J treated negative control group. In contrast, VLDLR or ApoER2 shRNA mediated knockdown of these receptors eliminated the remissive impact of Apo J on calcification, shown by Alizarin S and quantitative calcium assay (FIGS. 24A-24F), indicating Apo J functions through ApoER2 and VLDLR to regulate calcification process.

Figure 25A:
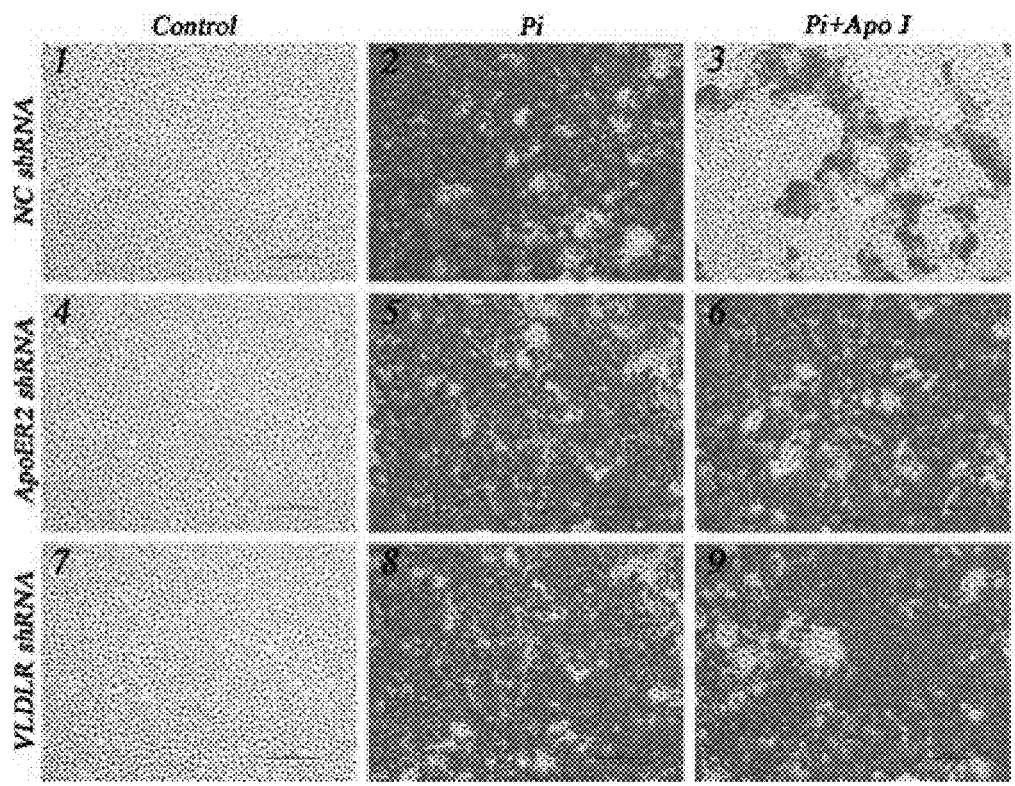
FIGS. 25A-25B—Knockdown of ApoER2 or VLDLR gene abolishes the inhibitory effect of Apo J on calcification. Alizarin red staining (25A) and calcium assay (25B) of receptor knockdown VSMCs under the treatment of Pi with or without Apo J (6 μg/mL). Scale bar=200 μm. Bars represent means±SD; n=3 per group. **P<0.01 vs. control; ##P<0.01 vs. Pi group.
Figure 25B:
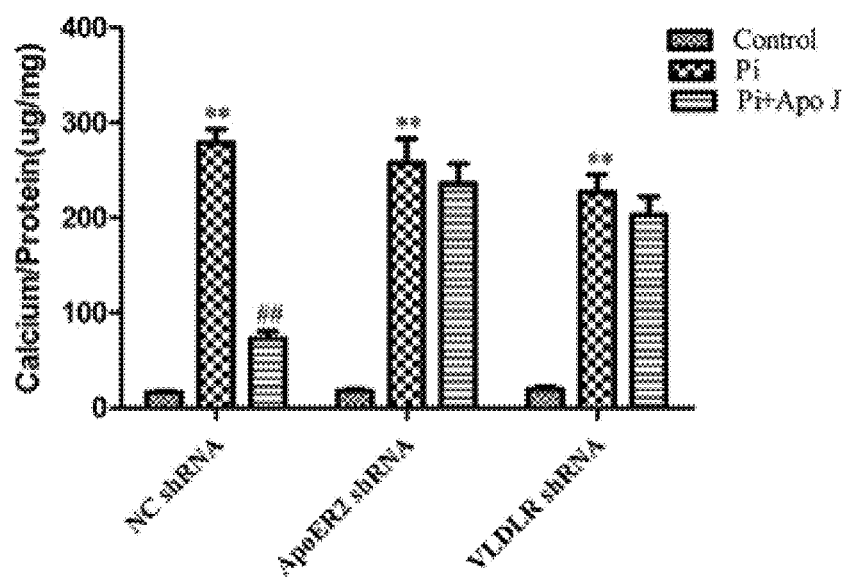
Figures 26A, 26B, 26C, 26D, 26E, 26F, 26G:
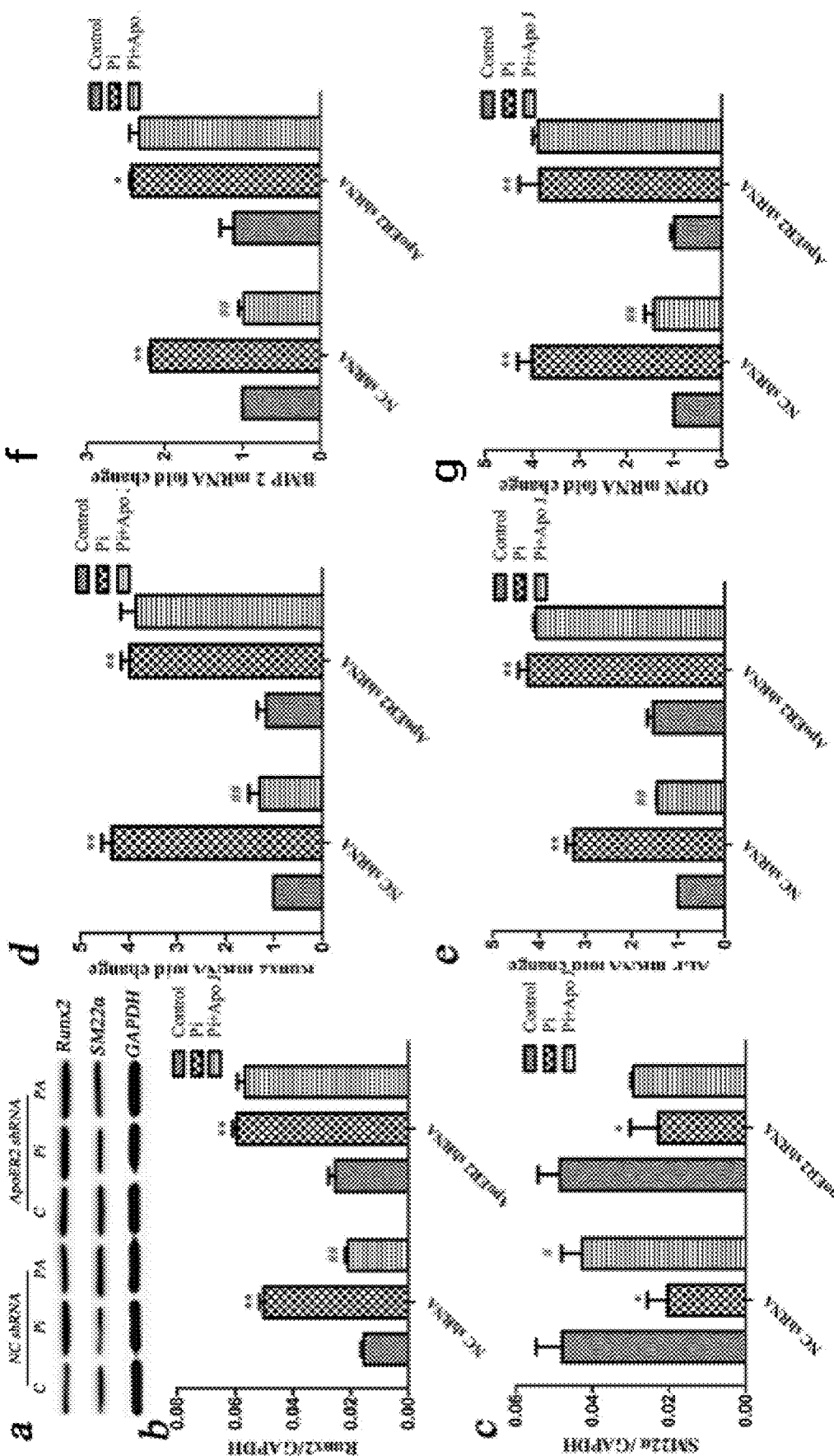
FIGS. 26A-26G—Knockdown of ApoER2 gene abolishes the effect of Apo J on calcification markers and smooth muscle lineage-specific markers. ApoE−/− VSMCs were treated with Pi and Apo J (6 μg/mL). 26A: SM22α and Runx2 protein expressions in ApoER2 knockdown cells were detected by western blot. GAPDH was used as the loading control. 26A-C: Densitometry analysis shows the quantification of SM22α and Runx2 in ApoER2 knockdown cells. 26D-G: Bar graph illustrating real-time PCR data showing the mRNA expression of Runx2, BMP-2, ALP and OPN. Relative mRNA expressions were normalized to GAPDH as an internal control. Bars represent means±SD; n=3 per group. +P<0.05 means negative control shRNA infected cells vs. ApoER2 shRNA infected cells, ++P<0.01; *P<0.05 vs. control, **P<0.01 vs. control; #P<0.05 vs. Pi group, ##P<0.01 vs. Pi group.
Figures 27A, 27B, 27C, 27D, 27E, 27F, 27G:
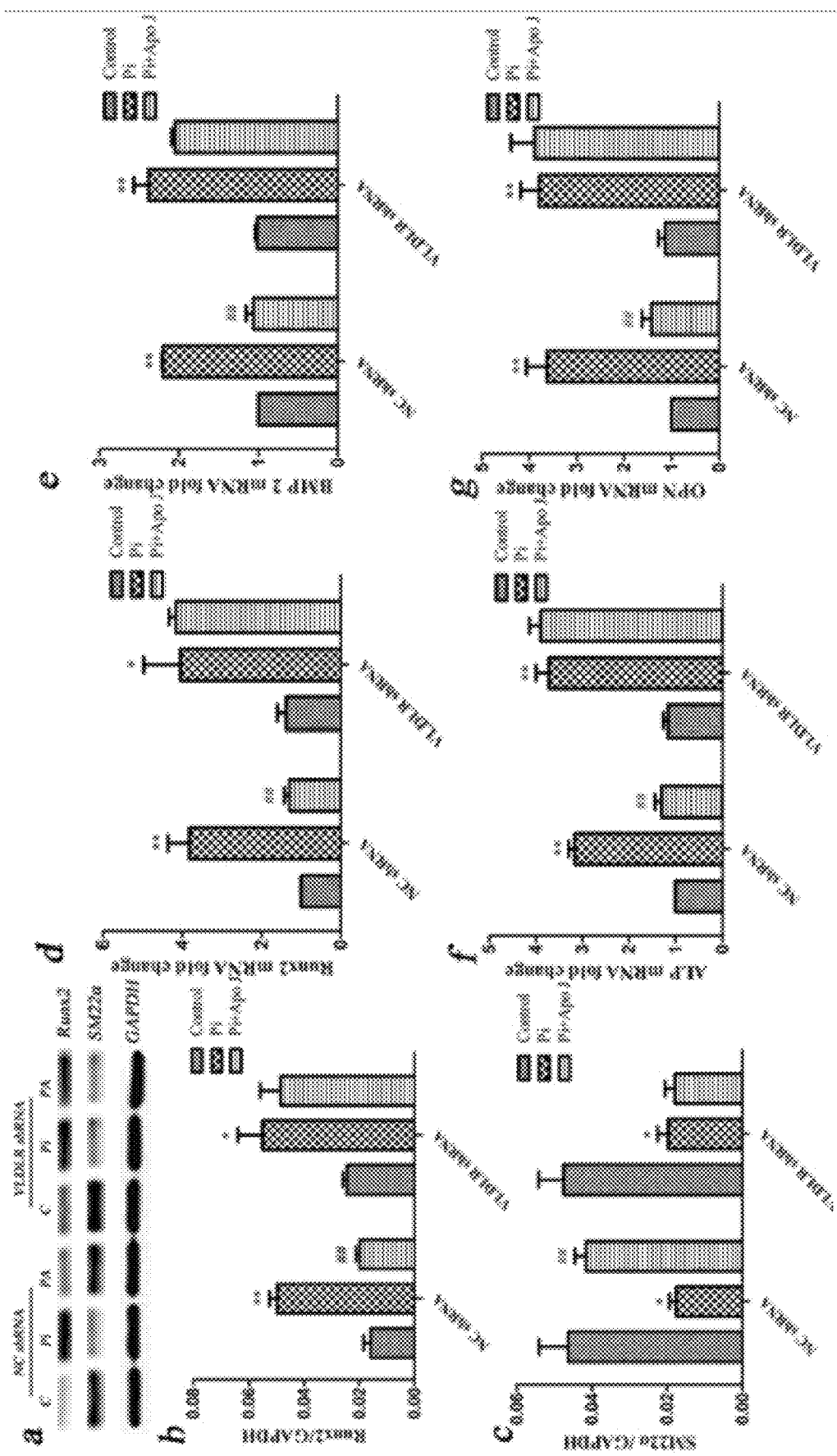
FIGS. 27A-27G—Knockdown of VLDLR gene abolishes the effect of Apo J on calcification markers and smooth muscle lineage-specific markers. ApoE−/− VSMCs were treated with Pi and Apo J (6 μg/mL). 27A: SM22α and Runx2 protein expressions in VLDLR knockdown cells were detected by western blot. GAPDH was used as the loading control. 27B-C: Densitometry analysis shows the quantification of SM22α and Runx2 in VLDLR knockdown cells. 27D-G: Bar graph illustrating real-time PCR data showing the mRNA expression of Runx2, BMP-2, ALP and OPN. Bars represent means±SD; n=3 per group. +P<0.05 means negative control shRNA infected cells vs. VLDLR shRNA infected cells, ++P<0.01; *P<0.05 vs. control, **P<0.01 vs. control; #P<0.05 vs. Pi group, ##P<0.01 vs. Pi group.
Figures 28A, 28B, 28C, 28D:
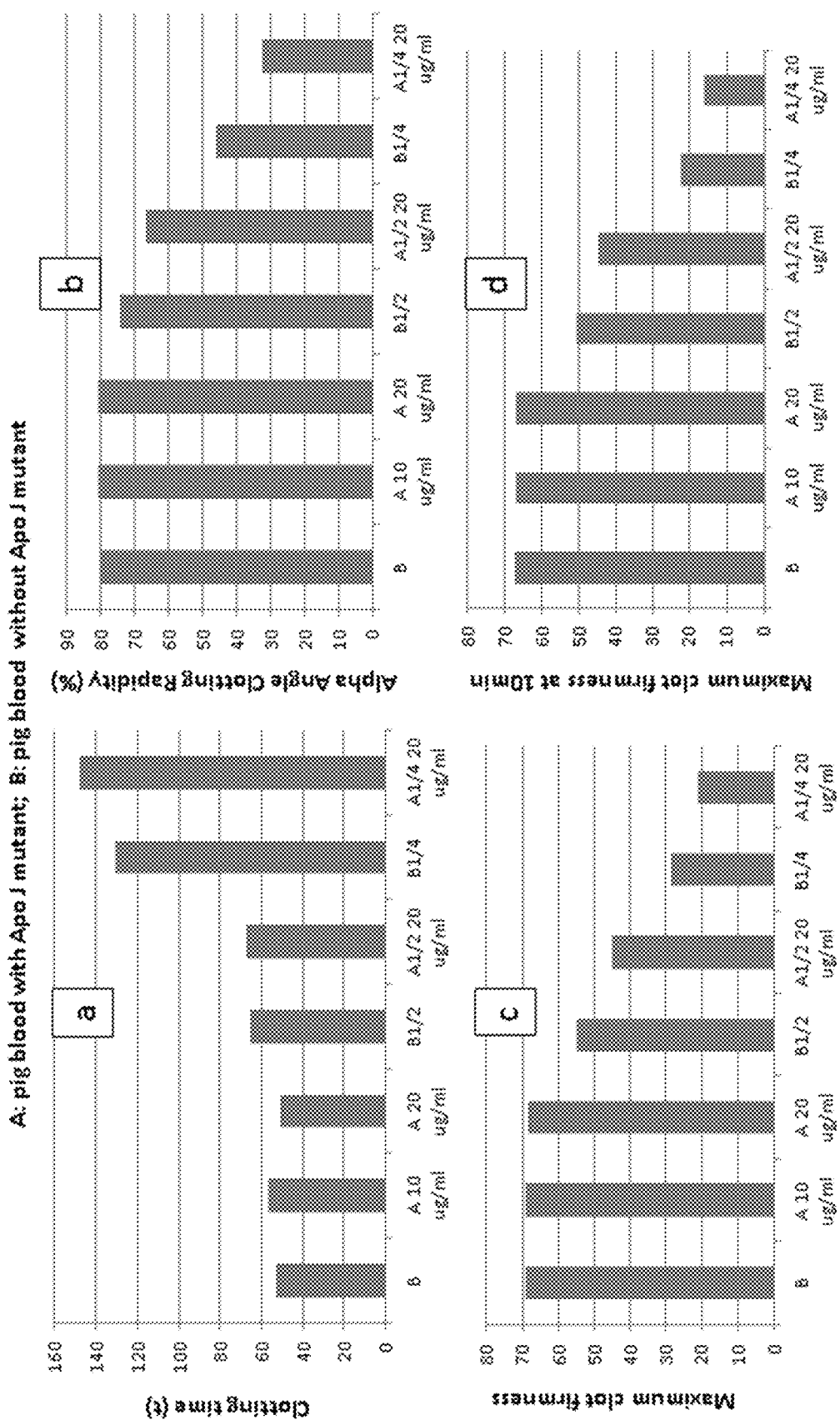
FIGS. 28a-28d—ApoJ mutants with a peptide comprising a thrombin-specific cleavage site exert an anti-coagulational effect by competitively inhibiting the conversion of fibrinogen into time of pig blood with (A) or without (B) ApoJ mutant. Fresh blood (0.3 ml) from adult pig at different dilutions (0, ½, and ¼ in PBS) was mixed with recombinant ApoJ mutant at 10 or 10 mg/ml), incubated at 37° C., and then subjected to rotational thromboelastometry (ROTEM™). a, clotting time; b, Alpha Angle clotting rapidity; c, maximum clot firmness; and d, maximum clot firmness at 10 minutes. Data represented from average of two separate experiments with the ApoJ mutant, Clusterin-ΔTMD-TRHis (SEQ ID NO: 8).

Knockdown of ApoER2 or VLDLR partially abolishes the effect of Apo J on osteogenesis related genes in calcification. Knockdown of ApoER2 or VLDLR weakened the negative regulation of Apo J on the enhanced expression of Runx2 in calcifying ApoE−/− VSMCs on protein level (FIGS. 25A and 26C and mRNA level (FIG. 27C). SM22α protein expression decreased in Pi treated cells with ApoER2 or VLDLR knockdown despite the presence of Apo J in culture medium (FIGS. 25B and 26D). Osteogenic markers alkaline phosphatase (ALP), bone morphogenic protein (BMP)-2, and Osteopontin (OPN) remained upregulated compared to uncalcified control group in ApoER2 or VLDLR knockdown cells; no significant differences were found in mRNA expressions of these markers between Apo J treated group and group without Apo J (FIGS. 27D-27F). This implies that knockdown of ApoER2 or VLDLR partially abolished the effect of Apo J on osteogenesis related genes in calcification in ApoE−/− VSMCs.

Studies were undertaken to assess the effect recombinant Clusterin on blood coagulation. ApoJ mutants with a peptide comprising a thrombin-specific cleavage site (e.g., Clusterin-TRHis, Clusterin-ΔTMD-TRHis, Clusterin-ΔTMD-ΔNLS-TRHis, HisTR-Clusterin-ΔTMD-ΔNLS, or HisTR-Clusterin-ΔTMD) exert an anti-coagulational effect by competitively inhibiting the conversion of fibrinogen into time of pig blood with (A) or without (B) ApoJ mutant. Fresh blood (0.3 ml) from adult pig at different dilutions (0, ½, and ¼ in PBS) was mixed with recombinant ApoJ mutant at 10 or 10 mg/ml), incubated at 37° C., and then subjected to rotational thromboelastometry (ROTEMTM). a, clotting time; b, Alpha Angle clotting rapidity; c, maximum clot firmness; and d, maximum clot firmness at 10 minutes. Data represented from average of two separate experiments with the ApoJ mutant, Clusterin-ΔTMD-TRHis (SEQ ID NO: 8). Thus, these data indicate that recombinant Clusterin with thrombin-cleavable peptide target, such as Clusterin-TRHis, Clusterin-ΔTMD-TRHis, Clusterin-ΔTMD-ΔNLS-TRHis, HisTR-Clusterin-ΔTMD-ΔNLS, or HisTR-Clusterin-ΔTMD can exert an anti-coagulation effect by competitively inhibiting the conversion of fibrinogen into fibrin and thus decreasing clot firmness and increasing the clotting time of blood. Thus, recombinant Clusterin may serve as a multi-functional agent for the treatment of patients who suffer from a heart disease, such as heart disease complicated by hypercholesterolemia, hypertension, hyperglycemia and thrombogenesis.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,215,051
Ahn H J, Bae J, Lee S, Ko J E, Yoon S, Kim S J, et al. Differential expression of clusterin according to histological type of endometrial carcinoma. Gynecol Oncol. 2008; 110(2):222-9.
Ansell B J, Navab M, Watson K E, Fonarow G C, Fogelman A M. Anti-inflammatory properties of HDL. Rev Endocr Metab Disord. 2004; 5(4):351-8.
Araki S, Israel S, Leskov K S, Criswell T L, Beman M, Klokov D Y, et al. Clusterin proteins: stress-inducible polypeptides with proposed functions in multiple organ dysfunction. BJR Suppl. 2005; 27:106-13.
Bitter, 1987, "Heterologous Gene Expression in Yeast", Methods in Enzymology, Eds. Berger & Kimmel, Acad. Press, N.Y., Vol. 152, pp. 673-684;
Brisson et al., 1984, Nature, 310:511-514.
Broglie et al., 1984, Science 224:838-843.
Choi-Miura N H, Takahashi Y, Nakano Y, Tobe T, Tomita M. Identification of the disulfide bonds in human plasma protein SP-40,40 (apolipoprotein-J). J Biochem (Tokyo). 1992; 112(4):557-61.
Colberre-Garapin, et al., 1981, J. Mol. Biol. 150:1.
Correa-Rotter R, Hostetter T H, Nath K A, Manivel J C, Rosenberg M E. Interaction of complement and clusterin in renal injury. J Am Soc Nephrol. 1992; 3(5):1172-9.
Coruzzi et al., 1984, EMBO J. 3:1671-1680.
Creighton, 1983, Proteins: Structures and Molecular Principles, W. H. Freeman & Co., N Y.
Current Protocols in Molecular Biology, Vol. 2, 1988, Ed. Ausubel et al., Greene Publish. Assoc. & Wiley Interscience, Ch. 13.
Dietzsch E, Murphy B F, Kirszbaum L, Walker I D, Garson O M. Regional localization of the gene for clusterin (SP-40,40; gene symbol CLI) to human chromosome 8p12-->p21. Cytogenet Cell Genet. 1992; 61(3):178-9.
Fink T M, Zimmer M, Tschopp J, Etienne J, Jenne D E, Lichter P. Human clusterin (CLI) maps to 8p21 in proximity to the lipoprotein lipase (LPL) gene. Genomics. 1993; 16(2):526-8.
Gelissen I C, Hochgrebe T, Wilson M R, Easterbrook-Smith S B, Jessup W, Dean R T, et al. Apolipoprotein J (clusterin) induces cholesterol export from macrophage-foam cells: a potential anti-atherogenic function? Biochem J. 1998; 331 (Pt 1):231-7.
Glover, 1986, DNA Cloning, Vol. II, IRL Press, Wash., D.C., Ch. 3.
Grant, et al., 1987, "Expression and Secretion Vectors for Yeast", Methods in Enzymology, Eds. Wu & Grossman, 1987, Acad. Press, N.Y., Vol. 153, pp. 516-544.
Grierson & Corey, 1988, Plant Molecular Biology, 2d Ed., Blackie, London, Ch. 7-9.
Gurley et al., 1986, Mol. Cell. Biol. 6:559-565.
Hoofnagle A N, Vaisar T, Mitra P, Chait A. HDL lipids and insulin resistance. Curr Diab Rep. 2010; 10(1):78-86.
Hoofnagle A N, Wu M, Gosmanova A K, Becker J O, Wijsman E M, Brunzell J D, et al. Low clusterin levels in high-density lipoprotein associate with insulin resistance, obesity, and dyslipoproteinemia. Arterioscler Thromb Vasc Biol. 2010; 30(12):2528-34. PMCID: 2988100.
Inouye & Inouye, 1985, Nucleic Acids Res. 13:3101-3109.
Ishikawa Y, Ishii T, Akasaka Y, Masuda T, Strong J P, Zieske A W, et al. Immunolocalization of apolipoproteins in aortic atherosclerosis in American youths and young adults: findings from the PDAY study. Atherosclerosis. 2001; 158(1):215-25.
Ishikawa Y, Akasaka Y, Ishii T, Komiyama K, Masuda S, Asuwa N, et al. Distribution and synthesis of apolipoprotein J in the atherosclerotic aorta. Arterioscler Thromb Vasc Biol. 1998; 18(4):665-72.
Jordan-Starck T C, Lund S D, Witte D P, Aronow B J, Ley C A, Stuart W D, et al. Mouse apolipoprotein J: characterization of a gene implicated in atherosclerosis. J Lipid Res. 1994; 35(2): 194-210.
Karlsson H, Leanderson P, Tagesson C, Lindahl M. Lipoproteomics I: mapping of proteins in low-density lipoprotein using two-dimensional gel electrophoresis and mass spectrometry. Proteomics. 2005; 5(2):551-65.

Kastelein J J, van Leuven S I, Burgess L, Evans G W, Kuivenhoven J A, Barter P J, et al. Effect of torcetrapib on carotid atherosclerosis in familial hypercholesterolemia. N Engl J Med. 2007; 356(16): 1620-30.

Klokov D, Criswell T, Leskov K S, Araki S, Mayo L, Boothman D A. I R-inducible clusterin gene expression: a protein with potential roles in ionizing radiation-induced adaptive responses, genomic instability, and bystander effects. Mutat Res. 2004; 568(1):97-110.

Koch-Brandt C, Morgans C. Clusterin: a role in cell survival in the face of apoptosis? Prog Mol Subcell Biol. 1996; 16:130-49.

Lee K B, Jeon J H, Choi I, Kwon O Y, Yu K, You K H. Clusterin, a novel modulator of TGF-beta signaling, is involved in Smad2/3 stability. Biochem Biophys Res Commun. 2008; 366(4):905-9.

Leskov K S, Klokov D Y, Li J, Kinsella T J, Boothman D A. Synthesis and functional analyses of nuclear clusterin, a cell death protein. J Biol Chem. 2003; 278(13):11590-600.

Li Y, Sagar M B, Wassler M, Shelat H, Geng Y J. Apolipoprotein-J prevention of fetal cardiac myoblast apoptosis induced by ethanol. Biochem Biophys Res Commun. 2007; 357(1): 157-61.

Li Y, Qu J, Shelat H, Gao S, Wassler M, Geng Y J. Clusterin induces CXCR4 expression and migration of cardiac progenitor cells. Exp Cell Res. 2010; 316(20):3435-42.

Logan & Shenk, 1984, Proc. Natl. Acad. Sci. USA 81:3655-3659.

Lowy, et al., 1980, Cell 22:817.

Mackness B, Hunt R, Durrington P N, Mackness M I. Increased immunolocalization of paraoxonase, clusterin, and apolipoprotein A-I in the human artery wall with the progression of atherosclerosis. Arterioscler Thromb Vasc Biol. 1997; 17(7):1233-8.

McMahon M, Grossman J, Skaggs B, Fitzgerald J, Sahakian L, Ragavendra N, et al. Dysfunctional proinflammatory high-density lipoproteins confer increased risk of atherosclerosis in women with systemic lupus erythematosus. Arthritis Rheum. 2009; 60(8):2428-37. PMCID: 2753974.

Mulligan & Berg, 1981, Proc. Natl. Acad. Sci. USA 78:2072.

Navab M, Hama-Levy S, Van Lenten B J, Fonarow G C, Cardinez C J, Castellani L W, et al. Mildly oxidized LDL induces an increased apolipoprotein J/paraoxonase ratio. J Clin Invest. 1997; 99(8):2005-19.

Navab M, Anantharamaiah G M, Reddy S T, Van Lenten B J, Wagner A C, Hama S, et al. An oral apoJ peptide renders HDL antiinflammatory in mice and monkeys and dramatically reduces atherosclerosis in apolipoprotein E-null mice. Arterioscler Thromb Vasc Biol. 2005; 25(9): 1932-7.

Nicholls S J, Rye K A, Barter P J. High-density lipoproteins as therapeutic targets. Curr Opin Lipidol. 2005; 16(3): 345-9.

Nissen S E, Tardif J C, Nicholls S J, Revkin J H, Shear C L, Duggan W T, et al. Effect of torcetrapib on the progression of coronary atherosclerosis. N Engl J Med. 2007; 356 (13):1304-16.

O'Bryan M K, Baker H W, Saunders J R, Kirszbaum L, Walker I D, Hudson P, et al. Human seminal clusterin (SP-40,40). Isolation and characterization. J Clin Invest. 1990; 85(5):1477-86. PMCID: 296595.

O'Hare, et al., 1981, Proc. Natl. Acad. Sci. USA 78:1527.

Oligonucleotide Synthesis, 1984, Gait, M. J., ed., IRL Press, Oxford.

Pajak B, Orzechowski A. Ethylenediaminetetraacetic acid affects subcellular expression of clusterin protein in human colon adenocarcinoma COLO 205 cell line. Anticancer Drugs. 2007; 18(1):55-63.

Ruther et al., 1983, EMBO J. 2:1791.

Sambrook et al., 1989.

Santerre, et al., 1984, Gene 30:147.

Shin J K, Han K A, Kang M Y, Kim Y S, Park J K, Choi W J, et al. Expression of clusterin in normal and preeclamptic placentas. J Obstet Gynaecol Res. 2008; 34(4):473-9.

Smith et al., 1983, J. Virol. 46: 584.

Smith J D. Dysfunctional HDL as a diagnostic and therapeutic target. Arterioscler Thromb Vasc Biol. 2010; 30(2): 151-5. PMCID: 2809786.

Stuart W D, Krol B, Jenkins S H, Harmony J A. Structure and stability of apolipoprotein J-containing high-density lipoproteins. Biochemistry. 1992; 31(36):8552-9.

Szybalska & Szybalski, 1962, Proc. Natl. Acad. Sci. USA 48:2026.

Takamatsu et al., 1987, EMBO J. 6:307-311.

The Molecular Biology of the Yeast *Saccharomyces*, 1982, Eds. Strathern, et al., Cold Spring Harbor Press, Vols. I and II.

Van Dijk A, Vermond R A, Krijnen P A, Juffermans L J, Hahn N E, Makker S P, et al. Intravenous clusterin administration reduces myocardial infarct size in rats. Eur J Clin Invest. 2010; 40(10):893-902.

Van Heeke & Schuster, 1989, J. Biol. Chem. 264:5503-5509.

Volkmann E R, Grossman J M, Sahakian L J, Skaggs B J, FitzGerald J, Ragavendra N, et al. Low physical activity is associated with proinflammatory high-density lipoprotein and increased subclinical atherosclerosis in women with systemic lupus erythematosus. Arthritis Care Res (Hoboken). 2010; 62(2):258-65. PMCID: 2853476.

von Eckardstein A, Hersberger M, Rohrer L. Current understanding of the metabolism and biological actions of HDL. Curr Opin Clin Nutr Metab Care. 2005; 8(2):147-52.

Weissbach & Weissbach, 1988, Methods for Plant Molecular Biology 1988, Academic Press, N Y, Section VIII, pp. 421-463.

Wilson M R, Easterbrook-Smith S B. Clusterin is a secreted mammalian chaperone. Trends Biochem Sci. 2000; 25(3): 95-8.

Wigler, et al., 1977, Cell 11:223.

Wigler, et al., 1980, Natl. Acad. Sci. USA 77:3567;

Yang C R, Leskov K, Hosley-Eberlein K, Criswell T, Pink J J, Kinsella T J, et al. Nuclear clusterin/XIP8, an x-ray-induced Ku70-binding protein that signals cell death. Proc Natl Acad Sci USA. 2000; 97(11):5907-12. PMCID: 18532.

What is claimed is:

1. A method of treating or preventing a cardiovascular disease in a subject comprising administering an effective amount of a composition comprising a polypeptide comprising a Clusterin coding sequence, said coding sequence having at least 95% sequence identity to SEQ ID NO: 3, said sequence not including Clusterin nuclear localization signal sequence (LEEAKKK; SEQ ID NO: 27) and not including the Clusterin transmembrane domain sequence (LLLFVGLLL; SEQ ID NO: 28).

2. The method of claim 1, wherein the Clusterin polypeptide is fused to a heterologous polypeptide sequence.

3. The method of claim 2, wherein the heterologous polypeptide sequence comprises a protease cleavage site.

4. The method of claim 3, wherein the protease cleavage site is a thrombin cleavage site.

5. The method of claim 1, wherein the Clusterin coding sequence has at least 98% sequence identity to SEQ ID NO: 3.

6. The method of claim 1, wherein the subject has heart disease.

7. The method of claim 6, wherein the subject further has hypercholesterolemia, hypertension, hyperglycemia and/or thrombogenesis.

8. The method of claim 1, wherein the cardiovascular disease is hypertension, hyperlipidemia, hypercholesterolemia, hyperglycemia, hypertension, atherosclerosis and atherosclerosis-associated ischemic heart failure, stenosis, calcification of cardiovascular tissues or stroke.

9. The method of claim 8, wherein the cardiovascular disease is hyperlipidemia or hypercholesterolemia.

10. The method of claim 8, wherein the cardiovascular disease is atherosclerosis, vascular calcification, valve tissue calcification or stenosis.

11. The method of claim 1, wherein the cardiovascular disease is myocardial infarction and cerebral infarction.

12. The method of claim 1, wherein the cardiovascular disease is diabetes, a diabetic vascular complication, vascular inflammation, vascular cell death or destruction of vascular wall.

13. The method of claim 1, wherein the effective amount is an amount effective to reduce blood cholesterol, blood glucose, blood triglyceride, increase efflux of intracellular cholesterol and/or increase vascular or cardiac cell survival.

14. The method of claim 1, wherein the composition is administered by intravenous injection, intratissue injection and/or catheter delivery.

15. The method of claim 1, wherein the polypeptide is aglycosylated.

16. The method of claim 1, wherein the polypeptide comprises a tag sequence.

17. The method of claim 16, wherein the tag sequence is a polyhistidine tag.

18. The method of claim 16, wherein the tag sequence is positioned N-terminally relative to the Clusterin coding sequence.

19. The method of claim 16, wherein the tag sequence is positioned C-terminally relative to the Clusterin coding sequence.

20. The method of claim 16, further comprising a protease cleavage site positioned between the tag sequence and the Clusterin coding sequence.

21. The method of claim 20, wherein the protease cleavage site it a thrombin or enteropeptidase cleavage site.

* * * * *

UNITED STATES PATENT AND TRADEMARK OFFICE
CERTIFICATE OF CORRECTION

| | |
|---|---|
| PATENT NO. | : 11,104,719 B2 |
| APPLICATION NO. | : 16/597400 |
| DATED | : August 31, 2021 |
| INVENTOR(S) | : Yong-Jian Geng |

It is certified that error appears in the above-identified patent and that said Letters Patent is hereby corrected as shown below:

In the Specification

In Column 1, Line 10, insert:
--STATEMENT REGARDING FEDERALLY SPONSORED RESEARCH OR DEVELOPMENT
This invention was made with government support under W81XWH-10-2-0125 awarded by the Department of Defense. The government has certain rights in the invention.--.

Signed and Sealed this
Thirtieth Day of May, 2023

Katherine Kelly Vidal
*Director of the United States Patent and Trademark Office*